US012390631B2

(12) United States Patent
Schwammenthal et al.

(10) Patent No.: US 12,390,631 B2
(45) Date of Patent: *Aug. 19, 2025

(54) BLOOD PUMP

(71) Applicant: Magenta Medical Ltd., Kadima (IL)

(72) Inventors: Ehud Schwammenthal, Ra'anana (IL); Yosi Tuval, Even Yehuda (IL); Daniel Glozman, Kfar Yona (IL); Tom Shtendel, Hod Hasharon (IL); Gad Lubinsky, Holon (IL)

(73) Assignee: Magenta Medical Ltd., Kadima (IL)

( * ) Notice: Subject to any disclaimer, the term of this patent is extended or adjusted under 35 U.S.C. 154(b) by 150 days.

This patent is subject to a terminal disclaimer.

(21) Appl. No.: 18/130,205

(22) Filed: Apr. 3, 2023

(65) Prior Publication Data

US 2023/0233837 A1    Jul. 27, 2023

Related U.S. Application Data

(63) Continuation of application No. 16/859,100, filed on Apr. 27, 2020, now Pat. No. 11,648,387, which is a
(Continued)

(51) Int. Cl.
*A61M 60/585* (2021.01)
*A61M 60/13* (2021.01)
(Continued)

(52) U.S. Cl.
CPC .......... *A61M 60/414* (2021.01); *A61M 60/13* (2021.01); *A61M 60/148* (2021.01);
(Continued)

(58) Field of Classification Search
CPC .. A61M 1/101; A61M 1/1012; A61M 1/1024; A61M 1/1029; A61M 1/122;
(Continued)

(56) References Cited

U.S. PATENT DOCUMENTS

| 4,822,345 A | 4/1989 | Danforth |
| 4,886,506 A | 12/1989 | Lovgren et al. |

(Continued)

FOREIGN PATENT DOCUMENTS

| AU | 2013205145 A1 | 5/2013 |
| AU | 2013257469 B2 | 3/2016 |

(Continued)

OTHER PUBLICATIONS

Advisory Action for U.S. Appl. No. 15/888,771 mailed May 4, 2022.
(Continued)

*Primary Examiner* — Ankit D Tejani
*Assistant Examiner* — Joshua Brendon Solomon
(74) *Attorney, Agent, or Firm* — Ballard Spahr LLP

(57) ABSTRACT

Apparatus and methods are described including a blood pump that includes at least one motor configured to be disposed outside a body of a subject, a catheter, a proximal impeller disposed on the catheter and configured to pump blood by rotating, and a distal impeller disposed on the catheter. The distal impeller is configured to pump blood by rotating and is disposed on the catheter distally to the proximal impeller such that longitudinal centers of the proximal and distal impellers are separated from each other by at least 3 cm. Other applications are also described.

26 Claims, 28 Drawing Sheets

Related U.S. Application Data continuation of application No. 15/574,948, filed as application No. PCT/IL2016/050525 on May 18, 2016, now Pat. No. 11,291,824.

(60) Provisional application No. 62/162,881, filed on May 18, 2015.

(51) Int. Cl.
- *A61M 60/148* (2021.01)
- *A61M 60/237* (2021.01)
- *A61M 60/414* (2021.01)
- *A61M 60/515* (2021.01)
- *A61M 60/523* (2021.01)
- *A61M 60/531* (2021.01)
- *A61M 60/808* (2021.01)
- *A61M 60/833* (2021.01)
- *A61M 60/865* (2021.01)

(52) U.S. Cl.
CPC ........ *A61M 60/237* (2021.01); *A61M 60/515* (2021.01); *A61M 60/523* (2021.01); *A61M 60/531* (2021.01); *A61M 60/585* (2021.01); *A61M 60/808* (2021.01); *A61M 60/833* (2021.01); *A61M 60/865* (2021.01)

(58) Field of Classification Search
CPC .............. A61M 1/1086; A61M 1/1013; A61M 1/1018; A61M 1/1034; A61M 1/125; A61M 60/205; A61M 60/216; A61M 60/221; A61M 60/226; A61M 60/414; A61M 60/13; A61M 60/148; A61M 60/237; A61M 60/515; A61M 60/523; A61M 60/531; A61M 60/585; A61M 60/808; A61M 60/833; A61M 60/865; A61M 60/33; A61M 60/804; A61M 60/861

See application file for complete search history.

(56) References Cited

U.S. PATENT DOCUMENTS

| | | |
|---|---|---|
| 4,919,647 A | 4/1990 | Nash |
| 4,954,055 A | 9/1990 | Raible et al. |
| 5,040,944 A * | 8/1991 | Cook ............ F04D 29/047 415/72 |
| 5,300,112 A * | 4/1994 | Barr .............. A61M 60/88 623/3.15 |
| 5,613,935 A | 3/1997 | Jarvik |
| 5,713,730 A | 2/1998 | Nose et al. |
| 5,749,855 A | 5/1998 | Reitan |
| 5,772,693 A | 6/1998 | Brownlee |
| 5,876,385 A | 3/1999 | Ikari et al. |
| 5,964,694 A | 10/1999 | Siess et al. |
| 6,086,527 A | 7/2000 | Talpade |
| 6,135,729 A | 10/2000 | Aber |
| 6,136,025 A | 10/2000 | Barbut et al. |
| 6,176,848 B1 | 1/2001 | Rau et al. |
| 6,183,220 B1 | 2/2001 | Ohara et al. |
| 6,247,892 B1 | 6/2001 | Kazatchkov et al. |
| 6,482,228 B1 | 11/2002 | Norred |
| 6,533,716 B1 | 3/2003 | Schmutz-Rode et al. |
| 6,592,567 B1 | 7/2003 | Levin et al. |
| 6,616,624 B1 | 9/2003 | Kieval |
| 6,884,210 B2 | 4/2005 | Nose et al. |
| 7,004,925 B2 | 2/2006 | Navia et al. |
| 7,011,620 B1 | 3/2006 | Siess |
| 7,070,555 B2 | 7/2006 | Siess |
| 7,144,364 B2 | 12/2006 | Barbut et al. |
| 7,159,593 B2 | 1/2007 | McCarthy et al. |
| 7,201,772 B2 | 4/2007 | Schwammenthal et al. |
| 7,335,192 B2 | 2/2008 | Keren et al. |
| 7,341,570 B2 | 3/2008 | Keren et al. |
| 7,485,104 B2 | 2/2009 | Kieval |
| 7,717,952 B2 | 5/2010 | Case et al. |
| 7,744,642 B2 | 6/2010 | Rittgers et al. |
| 7,762,941 B2 | 7/2010 | Jarvik |
| 7,766,853 B2 | 8/2010 | Lane |
| 7,766,892 B2 | 8/2010 | Keren et al. |
| 7,766,961 B2 | 8/2010 | Patel et al. |
| 7,780,628 B1 | 8/2010 | Keren et al. |
| 7,811,221 B2 | 10/2010 | Gross |
| 7,841,976 B2 | 11/2010 | McBride et al. |
| 7,914,503 B2 | 3/2011 | Goodson et al. |
| 7,927,068 B2 | 4/2011 | McBride et al. |
| 8,007,254 B2 | 8/2011 | Larose et al. |
| 8,012,121 B2 | 9/2011 | Goodson et al. |
| 8,079,948 B2 | 12/2011 | Shifflette |
| 8,221,492 B2 | 7/2012 | Case et al. |
| 8,235,933 B2 | 8/2012 | Keren et al. |
| 8,277,470 B2 * | 10/2012 | Demarais .......... A61M 25/0023 606/159 |
| 8,376,707 B2 | 2/2013 | Mcbride et al. |
| 8,449,443 B2 | 5/2013 | Rodefeld et al. |
| 8,512,262 B2 | 8/2013 | Gertner |
| 8,538,535 B2 | 9/2013 | Ariav et al. |
| 8,579,858 B2 | 11/2013 | Reitan et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,508 B2 | 5/2014 | Hastings et al. |
| 8,777,832 B1 | 7/2014 | Wang et al. |
| 8,849,398 B2 | 9/2014 | Evans |
| 8,992,163 B2 | 3/2015 | Mcbride et al. |
| 9,028,216 B2 | 5/2015 | Schumacher et al. |
| 9,067,006 B2 | 6/2015 | Toellner |
| 9,089,634 B2 | 7/2015 | Schumacher et al. |
| 9,138,518 B2 | 9/2015 | Campbell et al. |
| 9,162,017 B2 | 10/2015 | Evans et al. |
| 9,217,442 B2 | 12/2015 | Wiessler et al. |
| 9,314,558 B2 | 4/2016 | Er |
| 9,327,067 B2 | 5/2016 | Zeng et al. |
| 9,339,596 B2 | 5/2016 | Roehn |
| 9,358,329 B2 | 6/2016 | Fitzgerald et al. |
| 9,393,384 B1 | 7/2016 | Kapur et al. |
| 9,402,942 B2 | 8/2016 | Hastie et al. |
| 9,416,783 B2 | 8/2016 | Schumacher et al. |
| 9,572,915 B2 | 2/2017 | Heuring et al. |
| 9,597,205 B2 | 3/2017 | Tuval |
| 9,675,740 B2 | 6/2017 | Zeng et al. |
| 9,750,860 B2 | 9/2017 | Schumacher |
| 9,750,861 B2 | 9/2017 | Hastie et al. |
| 9,764,113 B2 | 9/2017 | Tuval et al. |
| 9,771,801 B2 | 9/2017 | Schumacher et al. |
| 9,895,475 B2 | 2/2018 | Toellner et al. |
| 9,903,384 B2 | 2/2018 | Roehn |
| 9,907,891 B2 | 3/2018 | Wiessler et al. |
| 9,913,937 B2 | 3/2018 | Schwammenthal et al. |
| 9,964,115 B2 | 5/2018 | Scheckel |
| 10,039,874 B2 | 8/2018 | Schwammenthal et al. |
| 10,052,419 B2 | 8/2018 | Er |
| 10,107,299 B2 | 10/2018 | Scheckel |
| 10,172,985 B2 | 1/2019 | Simon et al. |
| 10,179,197 B2 | 1/2019 | Kaiser et al. |
| 10,196,899 B2 | 2/2019 | Toellner et al. |
| 10,207,037 B2 | 2/2019 | Corbett et al. |
| 10,208,763 B2 | 2/2019 | Schumacher et al. |
| 10,215,187 B2 | 2/2019 | Mcbride et al. |
| 10,231,838 B2 | 3/2019 | Chin et al. |
| 10,245,363 B1 | 4/2019 | Rowe |
| 10,299,701 B2 | 5/2019 | Blanton et al. |
| 10,299,918 B2 | 5/2019 | Tuval |
| 10,342,904 B2 | 7/2019 | Schumacher |
| 10,342,906 B2 | 7/2019 | D'Ambrosio et al. |
| 10,363,350 B2 | 7/2019 | Schwammenthal et al. |
| 10,413,646 B2 | 9/2019 | Wiessler et al. |
| 10,478,538 B2 | 11/2019 | Scheckel et al. |

(56) References Cited

U.S. PATENT DOCUMENTS

| | | | |
|---|---|---|---|
| 10,478,539 B2 | 11/2019 | Pfeffer et al. | |
| 10,495,101 B2 | 12/2019 | Scheckel | |
| 10,557,475 B2 | 2/2020 | Roehn | |
| 10,583,231 B2 | 3/2020 | Schwammenthal et al. | |
| 10,584,589 B2 | 3/2020 | Schumacher et al. | |
| 10,589,012 B2 | 3/2020 | Toellner et al. | |
| 10,617,808 B2 | 4/2020 | Hastie et al. | |
| 10,662,967 B2 | 5/2020 | Scheckel | |
| 10,669,855 B2 | 6/2020 | Toellner et al. | |
| 10,765,789 B2 | 9/2020 | Zeng et al. | |
| 10,792,406 B2 | 10/2020 | Roehn et al. | |
| 10,799,624 B2 | 10/2020 | Pfeffer et al. | |
| 10,799,626 B2 | 10/2020 | Siess et al. | |
| 10,801,511 B2 | 10/2020 | Siess et al. | |
| 10,806,838 B2 | 10/2020 | Er | |
| 10,835,653 B2 | 11/2020 | Liebing | |
| 10,857,272 B2 | 12/2020 | Liebing | |
| 10,864,309 B2 | 12/2020 | Mcbride et al. | |
| 10,864,310 B2 | 12/2020 | Schwammenthal et al. | |
| 10,865,801 B2 | 12/2020 | Mcbride et al. | |
| 10,874,783 B2 | 12/2020 | Pfeffer et al. | |
| 10,881,845 B2 | 1/2021 | Siess et al. | |
| 10,894,115 B2 | 1/2021 | Pfeffer et al. | |
| 10,898,629 B2 | 1/2021 | Siess et al. | |
| 10,905,808 B2 * | 2/2021 | Tuval | A61M 60/419 |
| 10,907,646 B2 | 2/2021 | Bredenbreuker et al. | |
| 10,920,596 B2 | 2/2021 | Toellner et al. | |
| 10,926,013 B2 | 2/2021 | Schumacher et al. | |
| 10,935,038 B2 | 3/2021 | Siess | |
| 10,980,927 B2 | 4/2021 | Pfeffer et al. | |
| 11,007,350 B2 | 5/2021 | Tao et al. | |
| 11,020,584 B2 | 6/2021 | Siess et al. | |
| 11,027,114 B2 | 6/2021 | D'Ambrosio et al. | |
| 11,033,727 B2 | 6/2021 | Tuval et al. | |
| 11,033,729 B2 | 6/2021 | Scheckel et al. | |
| 11,040,187 B2 | 6/2021 | Wiessler et al. | |
| RE48,649 E | 7/2021 | Siess | |
| 11,116,960 B2 | 9/2021 | Simon et al. | |
| 11,123,539 B2 | 9/2021 | Pfeffer et al. | |
| 11,129,978 B2 | 9/2021 | Pfeffer et al. | |
| 11,167,124 B2 | 11/2021 | Pfeffer et al. | |
| 11,168,705 B2 | 11/2021 | Liebing | |
| 11,197,690 B2 | 12/2021 | Fantuzzi et al. | |
| 11,219,755 B2 | 1/2022 | Siess et al. | |
| 11,229,786 B2 | 1/2022 | Zeng et al. | |
| 11,253,692 B2 | 2/2022 | Schumacher | |
| 11,253,693 B2 | 2/2022 | Pfeffer et al. | |
| 11,260,215 B2 | 3/2022 | Scheckel et al. | |
| 11,266,824 B2 | 3/2022 | Er | |
| 11,268,521 B2 | 3/2022 | Toellner | |
| 11,273,301 B2 | 3/2022 | Pfeffer et al. | |
| 11,278,711 B2 | 3/2022 | Liebing | |
| 11,280,345 B2 | 3/2022 | Bredenbreuker et al. | |
| 11,291,824 B2 | 4/2022 | Schwammenthal et al. | |
| 11,298,525 B2 | 4/2022 | Jahangir | |
| 11,305,105 B2 | 4/2022 | Corbett et al. | |
| 11,313,228 B2 | 4/2022 | Schumacher et al. | |
| 11,338,124 B2 | 5/2022 | Pfeffer et al. | |
| 11,351,358 B2 | 6/2022 | Nix et al. | |
| 11,364,373 B2 | 6/2022 | Corbett et al. | |
| 11,421,701 B2 | 8/2022 | Schumacher et al. | |
| 11,434,922 B2 | 9/2022 | Roehn | |
| 11,484,701 B2 | 11/2022 | Schwammenthal et al. | |
| 11,648,387 B2 * | 5/2023 | Schwammenthal | A61M 60/515 600/16 |
| 11,648,391 B2 * | 5/2023 | Schwammenthal | A61M 60/135 600/16 |
| 11,648,392 B2 * | 5/2023 | Tuval | A61M 60/237 600/16 |
| 11,806,117 B2 * | 11/2023 | Tuval | A61M 60/135 |
| 2002/0107536 A1 | 8/2002 | Hussein | |
| 2003/0055486 A1 | 3/2003 | Adams et al. | |
| 2003/0149473 A1 | 8/2003 | Chouinard et al. | |
| 2003/0208097 A1 | 11/2003 | Aboul-Hosn et al. | |
| 2004/0064090 A1 | 4/2004 | Keren et al. | |
| 2004/0064091 A1 | 4/2004 | Keren et al. | |
| 2004/0111006 A1 | 6/2004 | Alferness et al. | |
| 2004/0116769 A1 | 6/2004 | Jassawalla et al. | |
| 2004/0167415 A1 | 8/2004 | Gelfand et al. | |
| 2004/0210236 A1 | 10/2004 | Allers et al. | |
| 2004/0219028 A1 | 11/2004 | Demarais et al. | |
| 2004/0260389 A1 | 12/2004 | Case et al. | |
| 2005/0033406 A1 | 2/2005 | Barnhart et al. | |
| 2005/0049692 A1 | 3/2005 | Numamoto et al. | |
| 2005/0055082 A1 | 3/2005 | Ben et al. | |
| 2005/0079274 A1 | 4/2005 | Palasis et al. | |
| 2005/0119682 A1 | 6/2005 | Nguyen et al. | |
| 2005/0137680 A1 | 6/2005 | Ortiz et al. | |
| 2006/0062672 A1 | 3/2006 | McBride et al. | |
| 2006/0064059 A1 | 3/2006 | Gelfand et al. | |
| 2006/0106449 A1 | 5/2006 | Ben | |
| 2006/0135961 A1 | 6/2006 | Rosenman et al. | |
| 2006/0245959 A1 | 11/2006 | Larose et al. | |
| 2007/0100435 A1 | 5/2007 | Case et al. | |
| 2007/0162103 A1 | 7/2007 | Case et al. | |
| 2007/0208291 A1 | 9/2007 | Patel | |
| 2007/0260327 A1 | 11/2007 | Case et al. | |
| 2007/0293808 A1 | 12/2007 | Williams et al. | |
| 2008/0103591 A1 | 5/2008 | Siess | |
| 2008/0114339 A1 | 5/2008 | McBride et al. | |
| 2008/0132748 A1 | 6/2008 | Shifflette | |
| 2008/0154236 A1 | 6/2008 | Elkins et al. | |
| 2008/0183280 A1 | 7/2008 | Agnew et al. | |
| 2009/0024195 A1 | 1/2009 | Rezai et al. | |
| 2009/0062597 A1 | 3/2009 | Shifflette | |
| 2009/0093796 A1 | 4/2009 | Pfeffer et al. | |
| 2009/0131785 A1 | 5/2009 | Lee et al. | |
| 2009/0264991 A1 | 10/2009 | Paul et al. | |
| 2009/0287299 A1 | 11/2009 | Tabor et al. | |
| 2009/0318857 A1 | 12/2009 | Goodson et al. | |
| 2010/0030259 A1 | 2/2010 | Pavcnik et al. | |
| 2010/0130810 A1 | 5/2010 | Mohl | |
| 2011/0004046 A1 | 1/2011 | Campbell et al. | |
| 2011/0106244 A1 | 5/2011 | Ferrari et al. | |
| 2011/0152999 A1 | 6/2011 | Hastings et al. | |
| 2011/0190874 A1 | 8/2011 | Celermajer et al. | |
| 2011/0213408 A1 | 9/2011 | Gross et al. | |
| 2011/0230949 A1 | 9/2011 | Haverkost et al. | |
| 2011/0257462 A1 | 10/2011 | Rodefeld et al. | |
| 2011/0264075 A1 | 10/2011 | Leung et al. | |
| 2011/0282128 A1 | 11/2011 | Reitan et al. | |
| 2011/0282274 A1 | 11/2011 | Fulton | |
| 2011/0301662 A1 | 12/2011 | Bar-Yoseph et al. | |
| 2011/0319906 A1 | 12/2011 | Rudakov et al. | |
| 2012/0022579 A1 | 1/2012 | Fulton | |
| 2012/0059460 A1 | 3/2012 | Reitan | |
| 2012/0089047 A1 | 4/2012 | Ryba et al. | |
| 2012/0116382 A1 | 5/2012 | Ku et al. | |
| 2012/0130469 A1 | 5/2012 | Cragg et al. | |
| 2012/0172654 A1 | 7/2012 | Bates | |
| 2012/0224970 A1 | 9/2012 | Schumacher et al. | |
| 2012/0232457 A1 | 9/2012 | Kandarpa | |
| 2012/0237357 A1 | 9/2012 | Schumacher et al. | |
| 2012/0301318 A1 | 11/2012 | Er | |
| 2012/0328460 A1 | 12/2012 | Horvath et al. | |
| 2013/0053623 A1 | 2/2013 | Evans et al. | |
| 2013/0053732 A1 | 2/2013 | Heuser | |
| 2013/0079874 A1 | 3/2013 | Doss et al. | |
| 2013/0177409 A1 | 7/2013 | Schumacher et al. | |
| 2013/0177432 A1 | 7/2013 | Toellner et al. | |
| 2013/0237744 A1 | 9/2013 | Pfeffer et al. | |
| 2014/0018840 A1 | 1/2014 | Morgan et al. | |
| 2014/0025041 A1 | 1/2014 | Fukuoka et al. | |
| 2014/0051908 A1 | 2/2014 | Khanal et al. | |
| 2014/0128659 A1 | 5/2014 | Heuring et al. | |
| 2014/0275722 A1 | 9/2014 | Zimmermann et al. | |
| 2014/0275726 A1 * | 9/2014 | Zeng | A61M 1/3659 600/16 |
| 2014/0350658 A1 | 11/2014 | Benary et al. | |
| 2015/0018597 A1 | 1/2015 | Fierens et al. | |
| 2015/0119633 A1 | 4/2015 | Haselby et al. | |

(56) References Cited

U.S. PATENT DOCUMENTS

| | | |
|---|---|---|
| 2015/0141739 A1 | 5/2015 | Hsu et al. |
| 2015/0157777 A1 | 6/2015 | Tuval et al. |
| 2015/0164662 A1 | 6/2015 | Tuval |
| 2015/0176582 A1 | 6/2015 | Liebing |
| 2015/0343136 A1 | 12/2015 | Nitzan et al. |
| 2015/0343186 A1 | 12/2015 | Nitzan et al. |
| 2016/0022890 A1 | 1/2016 | Schwammenthal et al. |
| 2016/0051741 A1 | 2/2016 | Schwammenthal et al. |
| 2016/0053768 A1 | 2/2016 | Schumacher et al. |
| 2016/0136343 A1 | 5/2016 | Anagnostopoulos |
| 2016/0184500 A1 | 6/2016 | Zeng |
| 2016/0279310 A1 | 9/2016 | Scheckel et al. |
| 2017/0049946 A1 | 2/2017 | Kapur et al. |
| 2017/0071769 A1 | 3/2017 | Mangiardi |
| 2017/0100527 A1 | 4/2017 | Schwammenthal et al. |
| 2017/0197021 A1 | 7/2017 | Nitzan et al. |
| 2018/0078615 A1 | 3/2018 | Lockwood et al. |
| 2018/0096531 A1 | 4/2018 | Greenhalgh et al. |
| 2018/0126130 A1 | 5/2018 | Nitzan et al. |
| 2018/0149165 A1 | 5/2018 | Siess et al. |
| 2018/0169313 A1 | 6/2018 | Schwammenthal et al. |
| 2018/0303993 A1 | 10/2018 | Schwammenthal et al. |
| 2019/0046702 A1 | 2/2019 | Siess et al. |
| 2019/0138350 A1 | 5/2019 | Kaneko et al. |
| 2019/0175340 A1 | 6/2019 | Tuval |
| 2019/0175806 A1 | 6/2019 | Tuval et al. |
| 2019/0209758 A1 | 7/2019 | Tuval et al. |
| 2019/0239998 A1 | 8/2019 | Tuval et al. |
| 2019/0269840 A1 | 9/2019 | Tuval et al. |
| 2020/0069857 A1 | 3/2020 | Schwammenthal et al. |
| 2020/0254162 A1 | 8/2020 | Schwammenthal et al. |
| 2020/0288988 A1 | 9/2020 | Goldvasser |
| 2021/0236797 A1 | 8/2021 | D'Ambrosio et al. |
| 2021/0268261 A1 | 9/2021 | Tuval et al. |
| 2022/0218976 A1 | 7/2022 | Friedland et al. |
| 2023/0233837 A1 | 7/2023 | Schwammenthal et al. |
| 2023/0233841 A1 | 7/2023 | Tuval et al. |

FOREIGN PATENT DOCUMENTS

| | | |
|---|---|---|
| CA | 2701809 A1 | 4/2009 |
| CN | 1219136 A | 6/1999 |
| DE | 1033690 B | 7/1958 |
| DE | 10336902 B3 | 8/2004 |
| EP | 1339443 A1 | 9/2003 |
| EP | 1651290 A1 | 5/2006 |
| EP | 1827531 A1 | 9/2007 |
| EP | 1871441 A2 | 1/2008 |
| EP | 2047872 A1 | 4/2009 |
| EP | 2047873 A1 | 4/2009 |
| EP | 2217300 A1 | 8/2010 |
| EP | 2218469 A1 | 8/2010 |
| EP | 2234658 A2 | 10/2010 |
| EP | 2282070 A1 | 2/2011 |
| EP | 2298374 A1 | 3/2011 |
| EP | 2299119 A1 | 3/2011 |
| EP | 2301598 A1 | 3/2011 |
| EP | 2308524 A1 | 4/2011 |
| EP | 2314331 A1 | 4/2011 |
| EP | 2345440 A1 | 7/2011 |
| EP | 2366412 A2 | 9/2011 |
| EP | 2376788 A1 | 10/2011 |
| EP | 2408489 A1 | 1/2012 |
| EP | 2424587 A1 | 3/2012 |
| EP | 2475415 A1 | 7/2012 |
| EP | 2607712 A1 | 6/2013 |
| EP | 2040639 B1 | 2/2014 |
| EP | 2662099 B1 | 9/2014 |
| EP | 2427230 B1 | 12/2014 |
| EP | 2396050 B1 | 1/2015 |
| EP | 2835141 A1 | 2/2015 |
| EP | 2840954 A1 | 3/2015 |
| EP | 2841122 A1 | 3/2015 |
| EP | 2841124 A1 | 3/2015 |
| EP | 2860849 A1 | 4/2015 |
| EP | 2868331 A2 | 5/2015 |
| EP | 2868332 A1 | 5/2015 |
| EP | 2999496 A2 | 3/2016 |
| EP | 3000492 A1 | 3/2016 |
| EP | 3000493 A1 | 3/2016 |
| EP | 3055922 A1 | 8/2016 |
| EP | 3062730 A1 | 9/2016 |
| EP | 3108909 A1 | 12/2016 |
| EP | 3127562 A1 | 2/2017 |
| EP | 3216467 A1 | 9/2017 |
| EP | 3222302 A1 | 9/2017 |
| EP | 3287154 A1 | 2/2018 |
| EP | 3287155 A1 | 2/2018 |
| EP | 3326567 A1 | 5/2018 |
| EP | 3329951 A1 | 6/2018 |
| EP | 3338825 A1 | 6/2018 |
| EP | 3205360 B1 | 8/2018 |
| EP | 3359214 A1 | 8/2018 |
| EP | 3359215 A1 | 8/2018 |
| EP | 3398624 A1 | 11/2018 |
| EP | 3398625 A1 | 11/2018 |
| EP | 3407930 A1 | 12/2018 |
| EP | 3446729 A1 | 2/2019 |
| EP | 3446730 A1 | 2/2019 |
| EP | 3606575 A1 | 2/2020 |
| EP | 3737436 A1 | 11/2020 |
| EP | 3897814 A1 | 10/2021 |
| JP | 2012505038 A | 3/2012 |
| JP | 2016509950 A | 4/2016 |
| WO | 90/13321 | 11/1990 |
| WO | 1994/01148 A1 | 1/1994 |
| WO | 9744071 A1 | 11/1997 |
| WO | 99/34847 | 7/1999 |
| WO | 9934847 A2 | 7/1999 |
| WO | 2001/083016 A2 | 5/2000 |
| WO | 0107787 A1 | 2/2001 |
| WO | 2002/070039 A2 | 3/2001 |
| WO | 0183016 A2 | 11/2001 |
| WO | 2002/038085 | 5/2002 |
| WO | 2002/38085 A1 | 5/2002 |
| WO | 03/006096 | 1/2003 |
| WO | 03/103745 A2 | 12/2003 |
| WO | 2004073796 A2 | 9/2004 |
| WO | 2005020848 A2 | 3/2005 |
| WO | 2007112033 A2 | 10/2007 |
| WO | 2007127477 A2 | 11/2007 |
| WO | 2008005747 A2 | 1/2008 |
| WO | 2008055301 A1 | 5/2008 |
| WO | 2009010963 A2 | 1/2009 |
| WO | 2009091965 A1 | 7/2009 |
| WO | 2009129481 A1 | 10/2009 |
| WO | 2010133567 A1 | 11/2010 |
| WO | 2010150208 A2 | 12/2010 |
| WO | 2011035926 A1 | 3/2011 |
| WO | 2011047884 A1 | 4/2011 |
| WO | 2011076441 A1 | 6/2011 |
| WO | 2012007141 A1 | 1/2012 |
| WO | 2013032849 A1 | 3/2013 |
| WO | 2013148697 A1 | 10/2013 |
| WO | 2013183060 A2 | 12/2013 |
| WO | 2014141284 A2 | 9/2014 |
| WO | 2015063277 A2 | 5/2015 |
| WO | 2015177793 A2 | 11/2015 |
| WO | 2016185473 A1 | 11/2016 |
| WO | 2017053361 A1 | 3/2017 |
| WO | 2017081561 A1 | 5/2017 |
| WO | 2018033920 A1 | 2/2018 |
| WO | 2018061001 A2 | 4/2018 |
| WO | 2018061002 A1 | 4/2018 |
| WO | 2018078615 A1 | 5/2018 |
| WO | 2018096531 A1 | 5/2018 |
| WO | 2018158636 A1 | 9/2018 |
| WO | 2018172848 A2 | 9/2018 |
| WO | 2018220589 A1 | 12/2018 |
| WO | 2019079342 A1 | 4/2019 |
| WO | 2019125899 A1 | 6/2019 |
| WO | 2019138350 A2 | 7/2019 |

(56) References Cited

FOREIGN PATENT DOCUMENTS

| WO | 2019158996 A1 | 8/2019 |
|---|---|---|
| WO | 2020234785 A1 | 11/2020 |
| WO | 2021159147 A1 | 8/2021 |

OTHER PUBLICATIONS

Communication for European Application No. 15753493.4 mailed Jul. 17, 2019.
Communication Pursuant to Article 94(3) EPC for European Patent Application No. 19216488.7 mailed Oct. 19, 2021.
Communication Pursuant to Article 94(3) for European Patent Application No. 20179137.3 mailed Nov. 9, 2021.
Corrected Notice of Allowance for U.S. Appl. No. 15/312,034 mailed Feb. 12, 2020.
Corrected Notice of Allowance for U.S. Appl. No. 15/423,368 mailed Apr. 17, 2019.
European Search Report for European Application No. 13800935 mailed Jan. 12, 2016.
European Search Report for European Application No. 14762232.8 mailed Sep. 28, 2016.
Examination Report for Canadian Application No. 2,948,121 mailed Dec. 15, 2021.
Examination Report for Canadian Application No. 2,948,121 mailed Jul. 8, 2021.
Examination Report for European Application No. 20179137.3 mailed Jan. 5, 2023.
Examination Report for Indian Application No. 201917018650 mailed Dec. 9, 2021.
Extended European Search Report for European Application No. 19212211.7 mailed Mar. 31, 2020.
Extended European Search Report for European Application No. 19215724.6 mailed Apr. 1, 2020.
Extended European Search Report for European Application No. 19216488.7 mailed Apr. 1, 2020.
Extended European Search Report for European Application No. 19216593.4 mailed Apr. 6, 2020.
Extended European Search Report for European Application No. 20179137.3 mailed Oct. 9, 2020.
Final Office Action for U.S. Appl. No. 14/931,363 mailed Jun. 1, 2017.
Final Office Action for U.S. Appl. No. 15/312,034 mailed Jan. 17, 2019.
Final Office Action for U.S. Appl. No. 15/574,948 mailed Aug. 26, 2020.
Final Office Action for U.S. Appl. No. 15/888,771 mailed Apr. 28, 2020.
Final Office Action for U.S. Appl. No. 15/888,771 mailed Dec. 9, 2021.
Final Office Action for U.S. Appl. No. 16/273,898 mailed Nov. 5, 2020.
Final Office Action for U.S. Appl. No. 16/278,323 mailed May 22, 2020.
Final Office Action for U.S. Appl. No. 16/859,100 mailed Jul. 13, 2022.
International Search Report and Written Opinion from International Application No. PCT/IB2020/054759 mailed Nov. 13, 2020.
International Search Report and Written Opinion from International Application No. PCT/IL2015/050532 mailed Jan. 27, 2016.
International Search Report and Written Opinion from International Application No. PCT/IL2016/050525 mailed Oct. 14, 2016.
International Search Report and Written Opinion from International Application No. PCT/IL2017/051092 mailed Jan. 16, 2018.
International Search Report and Written Opinion from International Application No. PCT/IL2017/051273 mailed Apr. 17, 2018.
International Search Report and Written Opinion from International Application No. PCT/IL2019/050334 mailed Jun. 17, 2019.
International Search Report and Written Opinion from International Application No. PCT/IL2013/050495 mailed Nov. 22, 2013.
International Search Report and Written Opinion from International Application No. PCT/IL2014/050289 mailed Sep. 11, 2014.
Invitation to Pay Additional Fees for International Application No. PCT/IB2020/054759 mailed Jul. 30, 2020.
Invitation to Pay Additional Fees for International Application No. PCT/IL2015/050532 mailed Nov. 17, 2015.
Issue Notification for U.S. Appl. No. 14/931,363 mailed Feb. 21, 2018.
Issue Notification for U.S. Appl. No. 15/312,034 mailed Feb. 19, 2020.
Issue Notification for U.S. Appl. No. 15/423,368 mailed May 8, 2019.
Issue Notification for U.S. Appl. No. 15/574,948 mailed Mar. 16, 2022.
Issue Notification for U.S. Appl. No. 15/888,771 mailed Oct. 12, 2022.
Issue Notification for U.S. Appl. No. 16/022,445 mailed Jul. 10, 2019.
Issue Notification for U.S. Appl. No. 16/035,871 mailed Dec. 29, 2020.
Issue Notification for U.S. Appl. No. 16/273,898 mailed Oct. 13, 2021.
Issue Notification for U.S. Appl. No. 16/278,323 mailed Nov. 24, 2020.
Issue Notification for U.S. Appl. No. 16/281,385 mailed Jun. 16, 2021.
Issue Notification for U.S. Appl. No. 16/335,786 mailed Jun. 2, 2021.
Issue Notification for U.S. Appl. No. 16/345,389 mailed May 26, 2021.
Issue Notification for U.S. Appl. No. 16/682,016 mailed Mar. 23, 2022.
Issue Notification for U.S. Appl. No. 16/682,269 mailed Mar. 23, 2022.
Non-Final Office Action for U.S. Appl. No. 14/405,144 mailed Feb. 22, 2016.
Non-Final Office Action for U.S. Appl. No. 14/405,144 mailed Jul. 14, 2016.
Non-Final Office Action for U.S. Appl. No. 14/567,439 mailed Nov. 16, 2016.
Non-Final Office Action for U.S. Appl. No. 14/774,081 mailed May 24, 2017.
Non-Final Office Action for U.S. Appl. No. 14/774,081 mailed Oct. 12, 2017.
Non-Final Office Action for U.S. Appl. No. 14/931,363 mailed Feb. 15, 2017.
Non-Final Office Action for U.S. Appl. No. 14/931,363 mailed Oct. 3, 2016.
Non-Final Office Action for U.S. Appl. No. 15/423,368 mailed Jun. 6, 2018.
Non-Final Office Action for U.S. Appl. No. 15/574,948 mailed Jan. 13, 2020.
Non-Final Office Action for U.S. Appl. No. 15/888,771 mailed Jun. 1, 2021.
Non-Final Office Action for U.S. Appl. No. 15/888,771 mailed May 25, 2022.
Non-Final Office Action for U.S. Appl. No. 15/888,771 mailed Oct. 4, 2019.
Non-Final Office Action for U.S. Appl. No. 16/022,445 mailed Aug. 9, 2018.
Non-Final Office Action for U.S. Appl. No. 16/035,871 mailed Jan. 22, 2020.
Non-Final Office Action for U.S. Appl. No. 16/242,797 mailed Nov. 16, 2021.
Non-Final Office Action for U.S. Appl. No. 16/273,898 mailed Feb. 17, 2021.
Non-Final Office Action for U.S. Appl. No. 16/273,898 mailed Jun. 18, 2020.
Non-Final Office Action for U.S. Appl. No. 16/278,323 mailed May 22, 2020.
Non-Final Office Action for U.S. Appl. No. 16/281,385 mailed Oct. 14, 2020.

(56) References Cited

OTHER PUBLICATIONS

Non-Final Office Action for U.S. Appl. No. 16/335,786 mailed Sep. 17, 2020.
Non-Final Office Action for U.S. Appl. No. 16/345,389 mailed Oct. 26, 2020.
Non-Final Office Action for U.S. Appl. No. 16/677,893 mailed Dec. 28, 2022.
Non-Final Office Action for U.S. Appl. No. 16/677,893 mailed Jan. 11, 2022.
Non-Final Office Action for U.S. Appl. No. 16/677,893 mailed Jul. 1, 2022.
Non-Final Office Action for U.S. Appl. No. 16/682,016 mailed Sep. 20, 2021.
Non-Final Office Action for U.S. Appl. No. 16/682,269 mailed Sep. 20, 2021.
Non-Final Office Action for U.S. Appl. No. 16/859,100 mailed Apr. 29, 2022.
Non-Final Office Action for U.S. Appl. No. 16/859,492 mailed Oct. 14, 2022.
Non-Final Office Action for U.S. Appl. No. 17/320,742 mailed Dec. 7, 2022.
Non-Final Office Action for U.S. Appl. No. 17/487,145 mailed Mar. 1, 2023.
Notice of Allowance for U.S. Appl. No. 14/567,439 mailed Jun. 2, 2017.
Notice of Allowance for U.S. Appl. No. 14/774,081 mailed Apr. 11, 2018.
Notice of Allowance for U.S. Appl. No. 14/931,363 mailed Dec. 12, 2017.
Notice of Allowance for U.S. Appl. No. 14/931,363 mailed Oct. 12, 2017.
Notice of Allowance for U.S. Appl. No. 15/312,034 mailed Jan. 15, 2020.
Notice of Allowance for U.S. Appl. No. 15/312,034 mailed Jun. 27, 2019.
Notice of Allowance for U.S. Appl. No. 15/423,368 mailed Apr. 4, 2019.
Notice of Allowance for U.S. Appl. No. 15/423,368 mailed Nov. 13, 2018.
Notice of Allowance for U.S. Appl. No. 15/574,948 mailed Jan. 27, 2022.
Notice of Allowance for U.S. Appl. No. 15/574,948 mailed Nov. 18, 2021.
Notice of Allowance for U.S. Appl. No. 15/888,771 mailed Jun. 28, 2022.
Notice of Allowance for U.S. Appl. No. 16/022,445 mailed Mar. 18, 2019.
Notice of Allowance for U.S. Appl. No. 16/035,871 mailed Aug. 28, 2020.
Notice of Allowance for U.S. Appl. No. 16/035,871 mailed Dec. 4, 2020.
Notice of Allowance for U.S. Appl. No. 16/273,898 mailed Jun. 30, 2021.
Notice of Allowance for U.S. Appl. No. 16/278,323 mailed Oct. 29, 2020.
Notice of Allowance for U.S. Appl. No. 16/281,385 mailed Mar. 8, 2021.
Notice of Allowance for U.S. Appl. No. 16/335,786 mailed Feb. 22, 2021.
Notice of Allowance for U.S. Appl. No. 16/345,389 mailed Feb. 16, 2021.
Notice of Allowance for U.S. Appl. No. 16/682,016 mailed Feb. 23, 2022.
Notice of Allowance for U.S. Appl. No. 16/682,269 mailed Feb. 23, 2022.
Notice of Allowance for U.S. Appl. No. 16/859,100 mailed Mar. 7, 2023.
Notice of Allowance for U.S. Appl. No. 16/859,492 mailed Mar. 15, 2023.
Notice of Allowance for U.S. Appl. No. 17/320,742 mailed Mar. 22, 2023.
Office Action for Australian Application No. 2015262870 mailed Apr. 29, 2019.
Office Action for Australian Application No. 2019202647 mailed Jun. 26, 2019.
Office Action for Australian Application No. 2020201055 mailed Sep. 15, 2020.
Office Action for Chinese Application No. 201380037335.4 mailed Mar. 22, 2017.
Office Action for Chinese Application No. 201380037335.4 mailed Oct. 17, 2016.
Office Action for Chinese Application No. 201380037335.4 mailed Sep. 20, 2017.
Office Action for Chinese Application No. 201780072633.5 mailed May 26, 2021.
Office Action for Chinese Application No. 201810418034.0 mailed Aug. 4, 2020.
Office Action for Chinese Application No. 201810418034.0 mailed Dec. 24, 2020.
Office Action for Chinese Application No. 201810418034.0 mailed Nov. 1, 2019.
Office Action for Chinese Application No. 201811196500.1 mailed Aug. 28, 2020.
Office Action for Chinese Application No. 201910109564.1 mailed Feb. 1, 2021.
Office Action for European Application No. 13800935 mailed Sep. 30, 2016.
Office Action for Japanese Application No. 2015/562562 mailed Jan. 29, 2019.
Office Action for Japanese Application No. 2015-562562 mailed Jun. 13, 2018.
Office Action for Japanese Application No. 2015562562 mailed Oct. 27, 2017.
Office Action for Japanese Application No. 2016/568548 mailed Mar. 18, 2019.
Office Action for Japanese Application No. 2019-520097 mailed Oct. 26, 2021.
Office Action for Japanese Application No. 2020-009045 mailed Feb. 1, 2021.
Office Action for Japanese Application No. 2020-93277 mailed Jun. 23, 2021.
Office Action for Japanese Application No. 2022-31553 mailed Dec. 23, 2022.
Restriction Requirement for U.S. Appl. No. 14/567,439 mailed Aug. 23, 2016.
Restriction Requirement for U.S. Appl. No. 14/774,081 mailed Mar. 9, 2017.
Restriction Requirement for U.S. Appl. No. 14/931,363 mailed Jul. 22, 2016.
Restriction Requirement for U.S. Appl. No. 15/888,771 mailed Apr. 15, 2019.
Restriction Requirement for U.S. Appl. No. 16/035,871, mailed Sep. 27, 2019.
Restriction Requirement for U.S. Appl. No. 16/677,893 mailed Sep. 22, 2021.
Restriction Requirement for U.S. Appl. No. 16/859,492 mailed Jul. 28, 2022.
U.S. Appl. No. 14/405,144, filed Dec. 2, 2014.
U.S. Appl. No. 14/567,439, filed Dec. 11, 2014.
U.S. Appl. No. 14/774,081, filed Sep. 9, 2015.
U.S. Appl. No. 15/423,368, filed Feb. 2, 2017.
U.S. Appl. No. 15/574,948, filed Nov. 17, 2017.
U.S. Appl. No. 16/022,445, filed Jun. 28, 2018.
U.S. Appl. No. 16/273,898, filed Feb. 12, 2019.
U.S. Appl. No. 16/275,559, filed Feb. 14, 2019.
U.S. Appl. No. 16/276,965, filed Feb. 15, 2019.
U.S. Appl. No. 16/277,411, filed Feb. 15, 2019.
U.S. Appl. No. 16/278,323, filed Feb. 18, 2019.
U.S. Appl. No. 16/281,264, filed Feb. 21, 2019.
U.S. Appl. No. 16/281,385, filed Feb. 21, 2019.
U.S. Appl. No. 16/345,389, filed Apr. 26, 2019.
U.S. Appl. No. 16/677,893, filed Nov. 8, 2019.

(56) References Cited

OTHER PUBLICATIONS

U.S. Appl. No. 16/682,016, filed Nov. 13, 2019.
U.S. Appl. No. 16/859,100, filed Apr. 27, 2020.
U.S. Appl. No. 16/859,492, filed Apr. 27, 2020.
U.S. Appl. No. 17/487,145, filed Sep. 28, 2021.
U.S. Appl. No. 61/656,244, filed Jun. 6, 2012.
U.S. Appl. No. 61/656,244, filed Jun. 6, 2013.
U.S. Appl. No. 61/779,803, filed Mar. 13, 2013.
U.S. Appl. No. 61/914,470, filed Dec. 11, 2013.
U.S. Appl. No. 61/914,475, filed Dec. 11, 2013.
U.S. Appl. No. 62/000,192, filed May 19, 2014.
U.S. Appl. No. 62/162,881, filed May 18, 2015.
U.S. Appl. No. 62/401,403, filed Sep. 29, 2016.
U.S. Appl. No. 62/412,631, filed Oct. 25, 2016.
U.S. Appl. No. 62/425,814, filed Nov. 23, 2016.
U.S. Appl. No. 62/543,540, filed Aug. 10, 2017.
U.S. Appl. No. 62/615,538, filed Jan. 10, 2018.
U.S. Appl. No. 62/665,715, filed May 2, 2018.
U.S. Appl. No. 62/681,868, filed Jun. 7, 2018.
U.S. Appl. No. 62/727,605, filed Sep. 6, 2021.
"Compendium of Technical and Scientific Information for the Hemopump Temporary Cardiac Assist System", Johnson & Johnson Interventional Systems, 1988, pp. 1-15.
Achour, et al., "Mechanical Left Ventricular Unloading Prior to Reperfusion Reduces Infarct Size in a Canine Infarction Model", Catheterization and Cardiovascular Interventions 64, 2005, pp. 182-192.
Agarwal, et al., "Newer-generation ventricular assist devices.", Best Practice & Research Clinical Anesthesiology, 2012, pp. 117-130.
Alba, et al., "The future is here: ventricular assist devices for the failing heart", Expert review of cardiovascular therapy, 2009, pp. 1067-1077.
Burnett, et al., "Renal Interstitial Pressure and Sodium Excretion During Renal Vein Constriction", American Physiological Society, 1980, pp. F279-F282.
Butler, et al., "The Hemopump—A New Cardiac Prothesis Device", Reprinted from IEEE Transactions on Biomedical Engineering, vol. 37, No. 2, Feb. 1990, pp. 192-195.
Chan, et al., "Rapid manufacturing techniques in the development of an axial blood pump impeller", Proc. Instn Mech. Engrs vol. 217 Part H: J. Engineering in Medicine, 2003, pp. 469-475.
Coxworth, "Artificial Vein Valve Could Replace Drugs for Treating Common Circulatory Problem", Published on Gizmag website (http://www.gizmag.com/artificial-venous-valve-cvi/21785/), Mar. 9, 2012.
Damman, et al., "Decreased Cardiac Output, Venous Congestion and the Association With Renal Impairment in Patients With Cardiac Dysfunction", European Journal of Heart Failure, 2007, pp. 872-878.
Damman, et al., "Increased Central Venous Pressure Is Associated With Impaired Renal Function and Mortality in a Broad Spectrum of Patients With Cardiovascular Disease", Journal of American College of Cardiology, 2009, pp. 582-588.
Dekker, et al., "Efficacy of a New Intraaortic Propeller Pump vs the Intraaortic Balloon Pump", Chest, vol. 123, Issue 6, Jun. 2003, pp. 2089-2095.
Doty, et al., "Effect of increased renal venous pressure on renal function", The Journal of Trauma: Injury, Infection, and Critical Care, Issue, Dec. 1999, p. 1000.
Doty, et al., "The Effect of Increased Renal Venous Pressure on Renal Function", The Journal of Trauma,, Dec. 1999, pp. 1000-1003.
Felker, et al., "Anemia as a Risk Factor and Therapeutic Target in Heart Failure", Journal of the American College of Cardiology, 2004, pp. 959-966.
Firth, et al., "Raised venous pressure: a direct cause of sodium retention in oedema?", Lancet, 1988, pp. 1033-1035.
Flameng, "Temporary Cardiac Assist with an Axial Pump System", Steinkopff Verlag Darmstadt, 1991, 79 pages.
Forman, et al., "Incidence, Predictors at Admission, and Impact of Worsening Renal Function Among Patients Hospitalized With Heart Failure", Journal of American College of Cardiology, 2004, pp. 61-67.
Fraser, et al., "The use of computational fluid dynamics in the development of ventricular assist devices", Medical engineering & physics, 2011, pp. 263-280.
Frazier, et al., "First Human Use of the Hemopump, a Catheter-Mounted Ventricular Assist Device", Annual of Thoracic Surgeons, vol. 49, 1990, pp. 299-304.
Frazier, et al., "Treatment of Cardiac Allograft Failure by use of an IntraAortic Axial Flow Pump", Journal of Heart Transplantation, St. Louis, vol. 9, No. 4, pp. 408-414, Jul. 1990.
Gomes, et al., "Heterologous valve implantation in the infra-renal vena cava for treatment of the iliac venous valve regurgitation disease", experimental study; Rev Bras Cir Cardiovasc, 2002, pp. 367-369.
Gunther, et al., "Experimentelle Radiologie", Life Sciences, Berichte Aus Der Rheinischwestfälischen Technischen Hochschule Aachen Ausgabe Feb. 2002, 9 pages.
Haddy, et al., "Effect of Elevation of Intraluminal Pressure on Renal Vascular Resistance", Circulation Research Journal of the American Heart Association, 1956, pp. 659-663.
Heywood, et al., "High prevalence of renal dysfunction and its impact on outcome in 118,465 patients hospitalized with acute decompensated heart failure", a report from the ADHERE database. J Cardiac Fail, 2007, pp. 422-430.
Hillege, et al., "Renal Function as a Predictor of Outcome in a Broad Spectrum of Patients With Heart Failure", Circulation Journal of the American Heart Association, 2006, pp. 671-678.
Hillege, et al., "Renal Function, Neurohormonal Activation, and Survival in Patients With Chronic Heart Failure", Circulation Journal of the American Heart Association, 2000, pp. 203-210.
Hsu, et al., "Review of recent patents on foldable ventricular assist devices", Recent Patents on Biomedical Engineering, 2012, pp. 208-222.
Ikari, "The Physics of Guiding Catheter; The IKARI Guiding Catheter in TRI", available at httu:i /www.docstoc.com/docs/148136553/The-[KARI-catheter---anovel-guide-for-TRI--.
Kafagy, et al., "Design of axial blood pumps for patients with dysfunctional fontan physiology: computational studies and performance testing", Artificial organs, 2015, pp. 34-42.
Kang, et al., "Fluid dynamics aspects of miniaturized axial-flow blood pump", Bio-medical materials and engineering, 2014, pp. 723-729.
Koochaki, et al., "A new design and computational fluid dynamics study of an implantable axial blood pump", Australasian Physical & Engineering Sciences in Medicine, 2013, pp. 417-422.
Lauten, et al., "Heterotopic Transcatheter Tricuspid Valve Implantation: First-In-Man Application of a Novel Approach to Tricuspid Regurgitation", European Heart Journal, Feb. 15, 2011, pp. 1207-1213.
Ledoux, et al., "Left Ventricular Unloading With Intra-aortic Counter Pulsation Prior to Reperfusion Reduces Myocardial Release of Endothelin-1 and Decreases Infarction Size in a Porcine Ischemia-Reperfusion Model", Catheterization and Cardiovascular Interventions 72, 2008, pp. 513-521.
McAlister, et al., "Renal Insufficiency and Heart Failure: Prognostic and Therapeutic Implications From a Prospective Cohort Study", Circulation Journal of the American Heart Association, 2004, pp. 1004-1009.
Merhige, et al., "Effect of the Hemopump Left Ventricular Assist Device on Regional Myocardial Perfusion and Function", Reduction of Ischemia during Coronary Occlusion, Johnson & Johnson Interventional Systems Supplement 3, Circulation vol. 80, No. 5, Nov. 1989, pp. III-159-III-166.
Mullens, et al., "Elevated Intra-Abdominal Pressure in Acute Decompensated Heart Failure. A Potential Contributor to Worsening Renal Function", Journal of the American College of Cardiology, 2008, pp. 300-306.
Mullens, et al., "Importance of Venous Congestion for Worsening of Renal Function in Advanced Decompensated Heart Failure", Journal of American College of Cardiology, 2009, pp. 589-596.

(56) References Cited

OTHER PUBLICATIONS

Mullens, et al., "Prompt Reduction in Intra-Abdominal Pressure Following Large-Volume Mechanical Fluid Removal Improves Renal Insufficiency in Refractory Decompensated Heart Failure", Journal of Cardiac Failure, 2008, pp. 508-514.
Notarius, et al., "Central Venous Pressure During Exercise: Role of Muscle Pump", Canadian Journal of Physiology and Pharmacology, 1996, pp. 647-651.
Park, et al., "Nutcracker Syndrome: Intravascular Stenting Approach", Nephrol Dial Transplant, 2000, pp. 99-101.
Reul, et al., "Blood pumps for circulatory support", Perfusion-Sevenoaks, 2000, pp. 295-312.
Roundtree, et al., "The Hemopump Cardiac Assist System: Nursing Care of the Patient", Reprinted from Critical Care Nurse, Apr. 1991.
Schmitz-Rode, et al., "An Expandable Percutaneous Catheter Pump for Left Ventricular Support", Journal of the American College of Cardiology, vol. 45, No. 11, 2005, pp. 1856-1861.
Scholz, et al., "Mechanical left Ventricular Unloading During High Risk Coronary Angioplasty: First Use of a New Percutaneous Transvalvular Left Ventricular Assist Device", Catheterization and Cardiovascular Diagnosis 31, 1994, pp. 61-69.
Semple, et al., "Effect of Increased Renal Venous Pressure on Circulatory "Autoregulation" of Isolated Dog Kidneys", Circulation Research Journal of the American Heart Association, 1959, pp. 643-648.
Siess, "System Analysis and Development of Intravascular Rotation Pumps for Cardiac Assist", Helmholtz-Institute—Chapter 3, Jun. 1998, 17 pages.
Smalling, et al., "Improved Regional Myocardial Blood Flow, Left Ventricular Unloading, and Infarct Salvage Using an Axial-Flow, Transvalvular Left Ventricular Assist Device", A Comparison With Intra-Aortic Balloon Counterpulsation and Reperfusion Alone in a Canine Infarction Model, Presented in part at the American College of Cardiology 38th Annual Scientific Session, Mar. 1990, pp. 1152-1160.
Smalling, et al., "The Hemopump: A transvalvular, axial flow, left ventricular assist device", Coronary Artery Disease, Circulatory support devices in clinical cardiology, vol. 2 No. 6, pp. 666-671, Aug. 1991.
Smalling, et al., "Transvalvular Left Ventricular Assistance in Cardiogenic Shock Secondary to Acute Myocardial Infarction", Evidence for Recovery From Near Fatal Myocardial Stunning, JACC vol. 23, No. 3, pp. 637-644, Mar. 1, 1994.
Song, et al., "Axial flow blood pumps", ASAIO journal, 2003, pp. 355-364.
Tamareille, et al., "Left ventricular unloading before reperfusion reduces endothelin-1 release and calcium overload in porcine myocardial infarction", Cardiopulmonary Support and Physiology, The Journal of Thoracic and Cardiovascular Surgery, vol. 136, No. 2, 2008, pp. 343-351.
Tang, et al., "Anemia in Chronic Heart Failure: Prevalence, Etiology, Clinical Correlates, and Treatment Options", Circulation Journal of the American Heart Association, 2006, pp. 2454-2461.
Throckmorton, et al., "Design of a protective cage for an intra vascular axial flow blood pump to mechanically assist the failing Fontan", Artificial organs, 2009, pp. 611-621.
Thunberg, et al., "Ventricular assist devices today and tomorrow", Journal of cardiothoracic and vascular anesthesia, 2010, pp. 656-680.
Timms, "A review of clinical ventricular assist devices", Medical engineering & physics, 2011, pp. 1041-1047.
Uthoff, et al., "Central venous pressure at emergency room presentation predicts cardiac rehospitalization in patients with decompensated heart failure", European Journal of Heart Failure, 2010, pp. 469-476.
Wampler, "Newspaper Articles", Captain Hemo, 1988, 6 pages.
Wampler, "Newsweek", Captain Hemo, May 16, 1988, 3 pages.
Wampler, "THI Today", Captain Hemo, Summer 1988, 2 pages.
Wampler, "Time Magazine", Captain Hemo, May 1988, 2 pages.
Wampler, et al., "Treatment of Cardiogenic Shock With the Hemopump Left Ventricular Assist Device", Annual of Thoracic Surgery, vol. 52, pp. 560-513, 1991.
Wampler, "U.S. News & World Report", Captain Hemo, pp. 1-2, May 16, 1988.
Wencker, "Acute Cardio-Renal Syndrome: Progression From Congestive Heart Failure to Congestive Kidney Failure", Current Heart Failure Reports, 2007, pp. 134-138.
Winton, "The Control of Glomerular Pressure by Vascular Changes Within the Mammalian Kidney, Demonstrated by the Actions of Adrenaline", Journal of Physiology, Nov. 1931, pp. 151-162.
Winton, "The Influence of Venous Pressure on the Isolated Mammalian Kidney", Journal of Physiology, Jun. 6, 1931, pp. 49-61.
Wood, "The Mechanism of the Increased Venous Pressure With Exercise in Congestive Heart Failure", Journal of Clinical Investigation, 1962, pp. 2020-2024.
Wu, et al., "Design and simulation of axial flow maglev blood pump", International Journal of Information Engineering and Electronic Business, 2011, p. 42.
Yancy, et al., "Clinical Presentation, Management, and In-Hospital Outcomes of Patients Admitted With Acute Decompensated Heart Failure With Preserved Systolic Function. A Report From the Acute Decompensated Heart Failure National Registry (ADHERE) Database", Journal of the American College of Cardiology, 2006, pp. 76-84.
Examination Report for Australian Application No. 2021225141 mailed Oct. 10, 2022.
Extended European Search Report for European Patent Application No. 23174906.0 mailed Aug. 21, 2023.
Issue Notification for U.S. Appl. No. 16/859,100 mailed Apr. 26, 2023.
Issue Notification for U.S. Appl. No. 16/859,492 mailed Apr. 26, 2023.
Issue Notification for U.S. Appl. No. 17/320,742 mailed Apr. 26, 2023.
Non-Final Office Action for U.S. Appl. No. 16/677,893 mailed May 9, 2023.
Notice of Acceptance for Australian Application No. 2017364359 mailed Nov. 17, 2022.
Notice of Allowance for U.S. Appl. No. 17/487,145 mailed Aug. 15, 2023.
Office Action for Canadian Application No. 3,039,302 mailed Mar. 21, 2023.
Office Action for Canadian Application No. 3,080,800 mailed Mar. 21, 2023.
Office Action for Canadian Application No. 3,126,978 mailed May 1, 2023.
Office Action for Canadian Application No. 3,126,978 mailed Nov. 1, 2022.
Office Action for Canadian Application No. 3,137,274 mailed Mar. 29, 2023.
U.S. Appl. No. 15/312,034, filed Nov. 17, 2016.
U.S. Appl. No. 15/888,771, filed Feb. 5, 2018.
U.S. Appl. No. 18/130,534, filed Apr. 4, 2023.
U.S. Appl. No. 18/130,698, filed Apr. 4, 2023.
U.S. Appl. No. 62/727,605, filed Sep. 6, 2018.
U.S. Appl. No. 18/422,309, filed Jan. 25, 2024.
Corrected Notice of Allowance for U.S. Appl. No. 18/130,534 mailed Nov. 24, 2023.
Issue Notification for U.S. Appl. No. 16/677,893 mailed Jan. 10, 2024.
Issue Notification for U.S. Appl. No. 17/487,145 mailed Nov. 22, 2023.
Issue Notification for U.S. Appl. No. 18/130,534 mailed Dec. 6, 2023.
Non-Final Office Action for U.S. Appl. No. 18/130,698 mailed Dec. 15, 2023.
Notice of Allowance for U.S. Appl. No. 16/677,893 mailed Oct. 19, 2023.
Notice of Allowance for U.S. Appl. No. 18/130,534 mailed Oct. 30, 2023.
Office Action for Chinese Application No. 202080038424.0 mailed Dec. 18, 2023.

(56) References Cited

OTHER PUBLICATIONS

Supplemental Notice of Allowance for U.S. Appl. No. 17/487,145 mailed Nov. 3, 2023.
U.S. Appl. No. 18/388,383, filed Nov. 9, 2023.
U.S. Appl. No. 18/510,983, filed Nov. 16, 2023.
Examination Report for European Application No. 19716995.6 mailed Mar. 1, 2024.
Issue Notification for U.S. Appl. No. 17/608,312 mailed Oct. 9, 2024.
Non-Final Office Action for U.S. Appl. No. 18/510,983 mailed Jun. 5, 2024.
Notice of Allowance for U.S. Appl. No. 18/130,698 mailed Aug. 21, 2024.
Notice of Allowance for U.S. Appl. No. 17/608,312 mailed Jun. 21, 2024.
Notice of Allowance for U.S. Appl. No. 17/608,312 mailed Sep. 3, 2024.
Notice of Allowance for U.S. Appl. No. 18/130,698 mailed Apr. 11, 2024.
Office Action for Canadian Application No. 3,137,274 mailed Jan. 15, 2024.
Office Action for Chinese Application No. 202110905794.6 mailed Feb. 1, 2024.
Office Action for Japanese Application No. 2021-563728 mailed Feb. 27, 2024.
Office Action for Japanese Application No. 2021-563728 mailed Jul. 10, 2024.
U.S. Appl. No. 16/750,354, filed Jan. 23, 2020.
U.S. Appl. No. 17/320,742, filed May 14, 2021.
U.S. Appl. No. 17/608,312, filed Nov. 2, 2021.
U.S. Appl. No. 62/851,769, filed May 23, 2019.
U.S. Appl. No. 62/870,822, filed Jul. 5, 2019.
U.S. Appl. No. 62/890,177, filed Aug. 22, 2019.
U.S. Appl. No. 62/983,786, filed Mar. 2, 2020.
U.S. Appl. No. 18/888,529, filed Sep. 18, 2024.

* cited by examiner

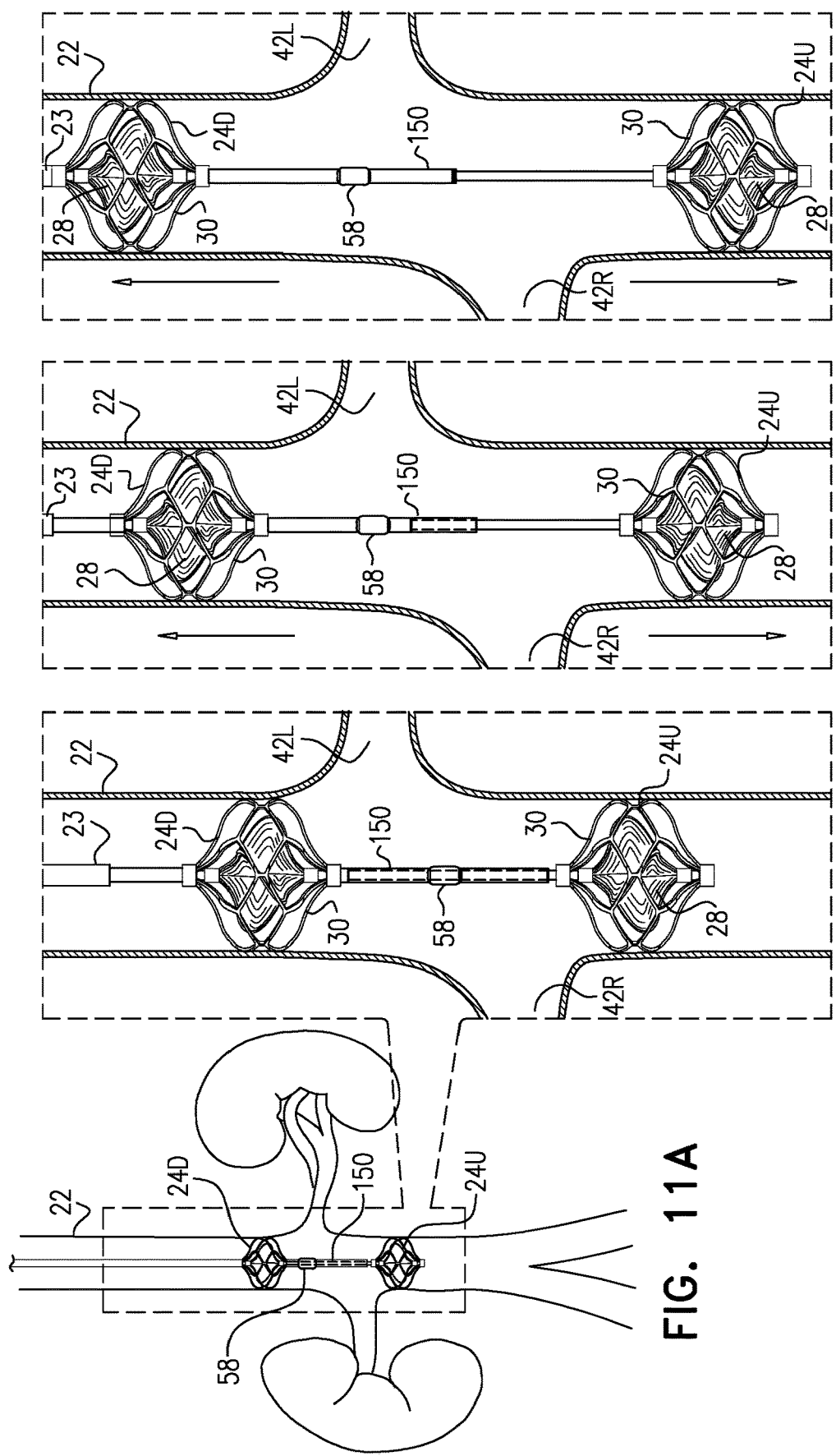

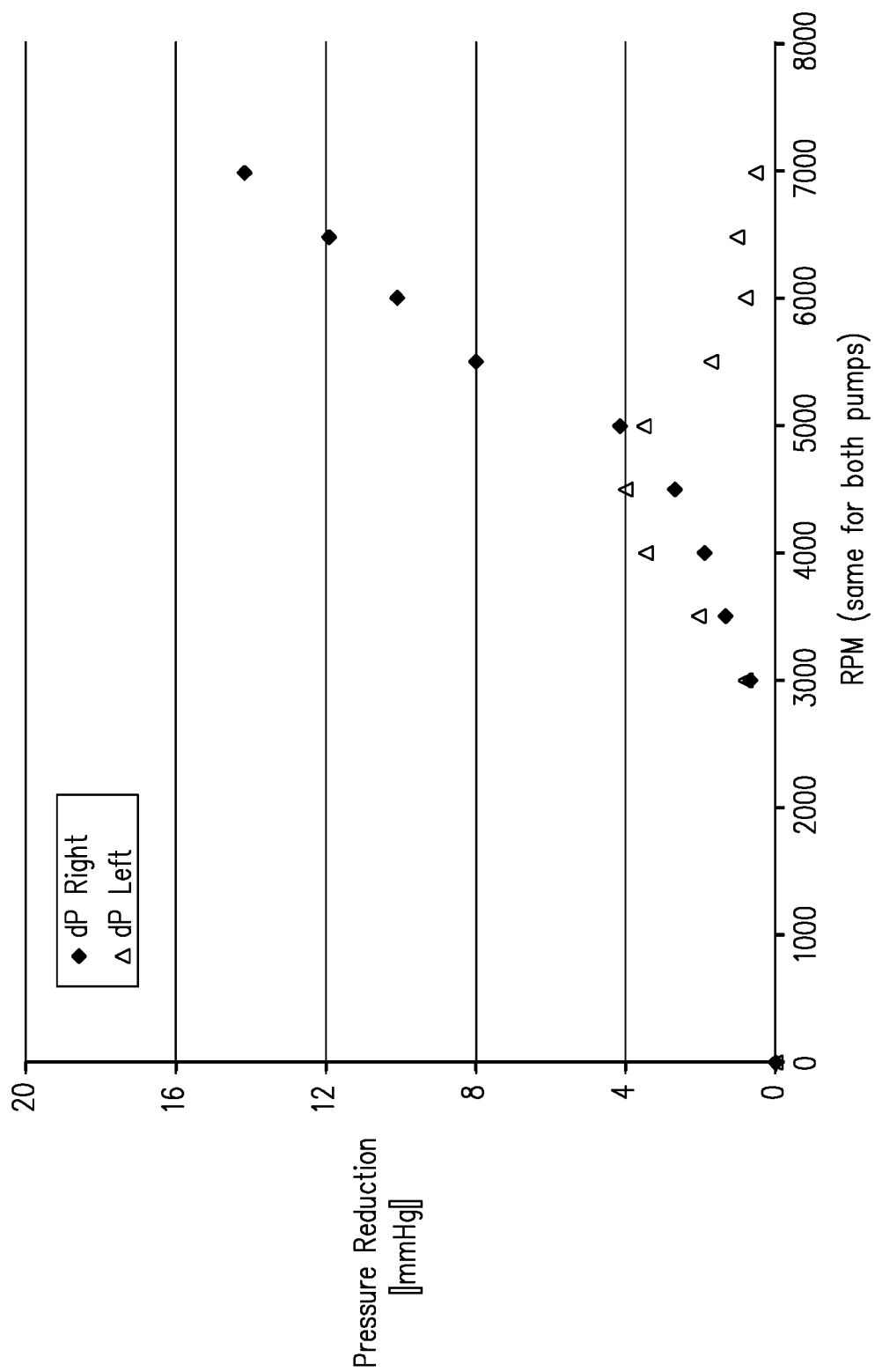

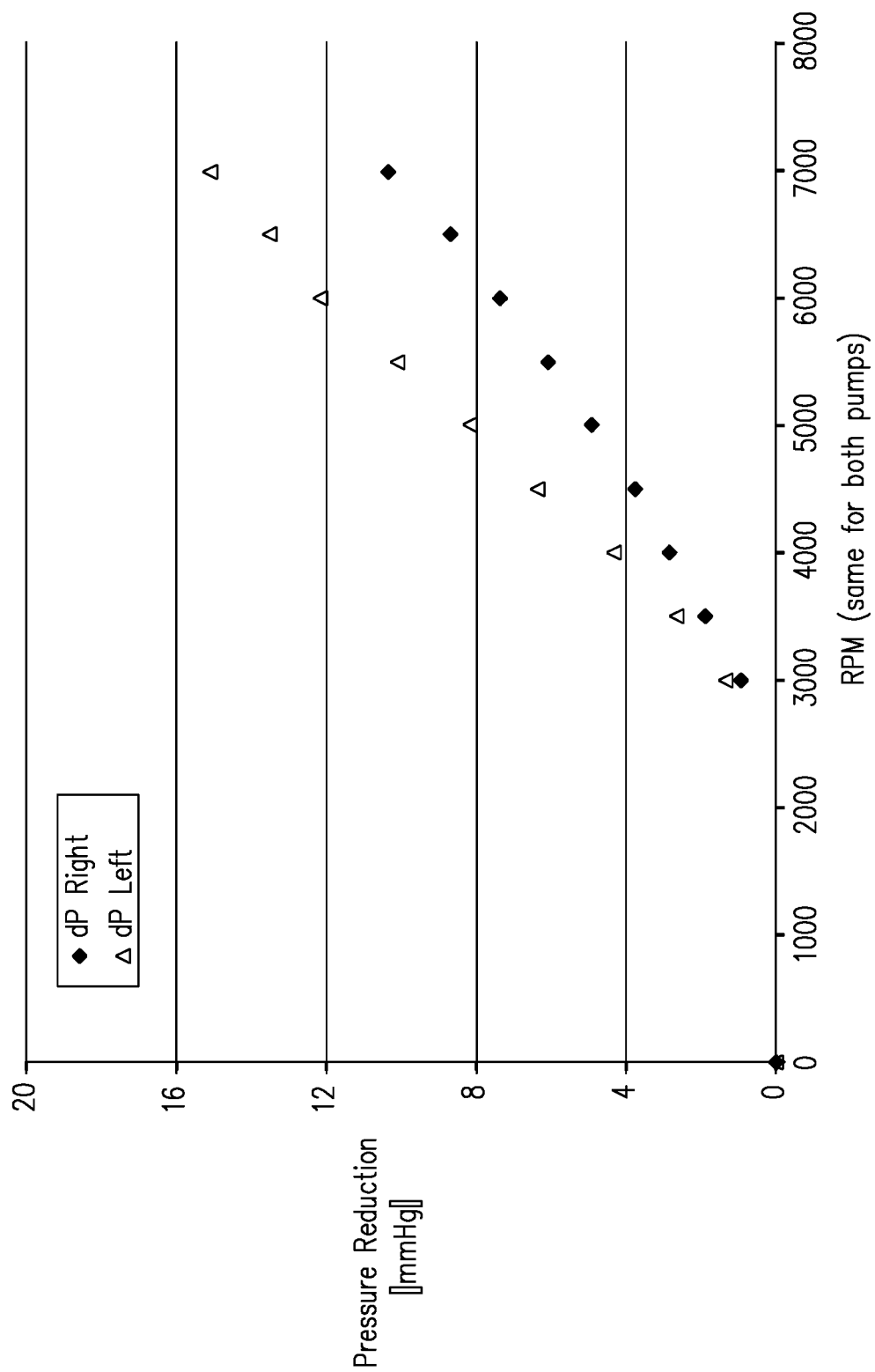

BLOOD PUMP

CROSS-REFERENCES TO RELATED APPLICATIONS

The present application is a continuation of U.S Ser. No. 16/859,100 to Schwammenthal (issued as U.S. Pat. No. 11,648,387), filed Apr. 27, 2020, which is a continuation of U.S. Ser. No. 15/574,948 to Schwammenthal (issued as U.S. Pat. No. 11,291,824), filed Nov. 17, 2017, which is a US national phase application of PCT Application No. PCT/IL/2016/050525 to Schwammenthal (published as WO 16/185473), filed May 18, 2016, which claims priority from U.S. Provisional Patent Application 62/162,881 to Schwammenthal, filed May 18, 2015, entitled "Blood pump," which is incorporated herein by reference.

FIELD OF EMBODIMENTS OF THE INVENTION

Some applications of the present invention generally relate to medical apparatus. Specifically, some applications of the present invention relate to apparatus and methods associated with placing a pump in one or more of a subject's renal veins, and/or in the subject's vena cava.

BACKGROUND

It is common for cardiac dysfunction or congestive heart failure to develop into kidney dysfunction, which, in turn, causes congestive heart failure symptoms to develop or worsen. Typically, systolic and/or diastolic cardiac dysfunction causes systemic venous congestion, which gives rise to an increase in renal venous and interstitial pressure. The increase in the pressure causes fluid retention by the body to increase due both to kidney dysfunction and renal neurohormonal activation, both of which typically develop as a result of the increase in renal venous and interstitial pressure. The resulting fluid retention causes congestive heart failure to develop or worsen, by causing a blood volume overload at the heart and/or by increasing systemic resistance. Similarly, it is common for kidney dysfunction and/or renal neurohormonal activation to develop into cardiac dysfunction and/or congestive heart failure. This pathophysiological cycle, in which cardiac dysfunction and/or congestive heart failure leads to kidney dysfunction and/or renal neurohormonal activation, or in which kidney dysfunction and/or renal neurohormonal activation leads to cardiac dysfunction and/or congestive heart failure, each dysfunction leading to deterioration in the other dysfunction, is called the cardio-renal syndrome.

Increased renal venous pressure has been experimentally shown to cause azotemia, and a reduction in glomerular filtration rate, renal blood flow, urine output, and sodium excretion. It has also been shown to increase plasma renin and aldosterone, and protein excretion. Venous congestion may also contribute to anemia via three different pathways: A reduction in the kidney's erythropoietin production, hemodilution by fluid retention, and an inflammatory response leading to a reduced gastro-intestinal iron uptake.

Mechanistically, increased renal venous pressure may cause intracapsular pressure and, subsequently, interstitial peritubular pressure, to rise. A rise in peritubular pressure may impact tubular function (reduce sodium excretion), as well as diminish glomerular filtration, by raising the pressure in the Bowman capsule.

In heart failure patients, increased renal venous pressure may not only result from increased central venous (right atrial) pressure, but also from intraperitoneal fluid accumulations (ascites) exerting direct pressure on the renal veins. Reduction of intraabdominal pressure in heart failure patients by removal of fluid (e.g., via paracentesis, and/or ultrafiltration), has been shown to reduce plasma creatinine levels.

Increased venous return resulting from activation of the "leg muscle pump" during physical activity such as walking may raise systemic venous pressure, particularly in heart failure patients, and may result in reflux into the renal veins.

SUMMARY OF EMBODIMENTS

In accordance with some applications of the present invention, a subject is identified as suffering from cardiac dysfunction, congestive heart failure, reduced renal blood flow, increased renal vascular resistance, arterial hypertension, diabetes, and/or kidney dysfunction. In response thereto, blood pressure within the subject's renal veins is reduced by placing at least one pump in the subject's vena cava, and generating a low-pressure region within the subject's vena cava adjacent to junctions of the vena cava with the subject's renal veins, by activating the pump to pump blood away from the region. The pump is activated such that blood pressure within the low-pressure region is lower than central venous pressure of the subject. Typically, a downstream pump is placed within the vena cava downstream of the junctions of the vena cava with the subject's renal veins, and the pump pumps blood through the vena cava in the downstream direction, away from the junctions. For some applications, an upstream pump is placed within the vena cava upstream of the junctions of the vena cava with the subject's renal veins, and the pump pumps blood through the vena cava in the upstream direction, away from the junctions. Alternatively or additionally, an occlusion element, such as a balloon or a covered stent is placed in the vena cava upstream of the junctions, and is configured to partially occlude the vena cava upstream of the junctions.

For some applications, the upstream and downstream pumps are disposed on a single catheter. Typically, the catheter is inserted into the vena cava via a venous pathway, e.g., via the femoral vein, via the subclavian vein, or via the jugular vein. For some applications, the upstream pump, or the occlusion element is disposed on a first catheter, which is inserted via a vein that is below the subject's inferior vena cava (e.g., the femoral vein), and the downstream pump is disposed on a second catheter, which is inserted via a vein that is above the subject's inferior vena cava (e.g., the subclavian vein, or the jugular vein).

For some applications, the downstream pump and/or the upstream pump includes an impeller and a cage. For some applications, impellers of the downstream and the upstream pumps rotate in the same direction, but the downstream pump is configured to pump blood in the downstream direction and the upstream pump is configured to pump blood in the upstream direction. For some such applications, a single motor is used to impart rotational motion to both of the impellers, and there is a shaft disposed between the impellers that imparts rotational motion from a first one of the impellers to a second one of the impellers. Typically, for such applications, the impellers of the upstream and the downstream pumps are (a) of opposing handedness with respect to one another (i.e., one of the impellers is a left-handed impeller, and the other impeller is a right-handed impeller), and (b) are disposed upon the aforementioned shaft, such that the impellers are facing opposite directions to one another.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

There is therefore provided, in accordance with some applications of the present invention, apparatus including:

a catheter;

a first pump disposed on the catheter;

a second pump disposed on the catheter, proximally to the first pump; and a control unit configured to control activation of the first and second pumps, the first and second pumps being configured, when activated, to pump fluid in opposite directions from one another.

For some applications, the catheter is configured to be placed within a vena cava of a subject such that the first pump is disposed downstream of junctions of the vena cava with all renal veins of the subject, and such that the second pump is disposed upstream of junctions of the vena cava with all renal veins of the subject.

For some applications, the first and second pumps are configured to lower pressure within the subject's renal veins by:

the first pump pumping blood through the vena cava in a downstream direction, and the second pump pumping blood through the vena cava in an upstream direction.

For some applications, the catheter is configured to be placed within the subject's vena cava by being inserted via a vein of the subject selected from the group consisting of: a subclavian vein, a jugular vein, and a femoral vein.

For some applications:

the first pump includes a first impeller configured to pump blood through the vena cava by rotating; and the second pump includes a second impeller configured to pump blood through the vena cava by rotating.

For some applications:

the apparatus further includes a first cage, the first impeller being disposed inside the first cage, and the first cage configured to maintain a separation between the first impeller and an inner wall of the vena cava; and the apparatus further includes a second cage, the second impeller being disposed inside the second cage, and the second cage being configured to maintain a separation between the second impeller and the inner wall of the vena cava.

For some applications, the first and second impellers are configured, when activated, to pump blood in opposite directions from one another by the first and second impellers being rotated in the same direction as one another, as viewed from an external reference point.

For some applications, the first and second impellers are of opposing-handedness with respect to one another, and are disposed upon the catheter such that the impellers face opposite directions from one another.

For some applications, the catheter is configured to be placed within a blood vessel of a subject, and the first and second pumps are configured to generate a region within the blood vessel that is of lower blood pressure than elsewhere within the blood vessel by pumping blood away from a region of the blood vessel between the first and second pumps.

For some applications, the catheter is configured to be placed within a main vein of a subject into which blood flows from a tributary venous system such that:

the first pump is placed in the main vein, downstream of the tributary venous system; and the second pump is placed in the main vein, upstream of the tributary venous system.

For some applications, the catheter is configured to be placed within a blood vessel of a subject, and the first and second pumps are configured to generate a region within the blood vessel that is of higher blood pressure than elsewhere within the blood vessel by pumping blood toward a region of the blood vessel between the first and second pumps.

For some applications, the catheter is configured to be placed within a main artery of a subject that supplies a branching arterial system that branches from the main artery such that:

the first pump is placed in the main artery, downstream of the branching arterial system; and the second pump is placed in the main artery, upstream of the branching arterial system.

For some applications:

the first pump includes a first impeller configured to pump fluid by rotating; and the second pump includes a second impeller configured to pump fluid by rotating.

For some applications, the first and second impellers are configured, when activated, to pump fluid in opposite directions from one another by the first and second impellers being rotated in the same direction as one another, as viewed from an external reference point.

For some applications, the first and second impellers are of opposing-handedness with respect to one another, and are disposed upon the catheter such that the impellers face opposite directions from one another.

For some applications, the apparatus further includes a motor configured to cause the first and second impellers to pump fluid in opposite directions from one another by rotating the first and second impellers in the same direction as one another.

There is further provided, in accordance with some applications of the present invention, apparatus including:

a catheter;

a first impeller disposed on the catheter; and a second impeller disposed on the catheter, proximally to the first impeller, longitudinal centers of the first and second impellers being separated from one another by a distance of at least 3 cm, the distance being measured along a longitudinal axis of the catheter.

For some applications, the first and second impellers are of opposing-handedness with respect to one another, and are disposed upon the catheter such that the impellers face opposite directions from one another.

For some applications, the catheter is configured to be placed within a vena cava of a subject such that the first impeller is disposed downstream of junctions of the vena cava with all renal veins of the subject, and such that the second impeller is disposed upstream of junctions of the vena cava with all renal veins of the subject.

For some applications, the catheter is configured to be placed within the subject's vena cava by being inserted via a vein of the subject selected from the group consisting of: a subclavian vein, a jugular vein, and a femoral vein.

For some applications:

the apparatus further includes a first cage, the first impeller being disposed inside the first cage, and the first cage being configured to maintain a separation between the first impeller and an inner wall of the vena cava; and the apparatus further includes a second cage, the second impeller being disposed inside the second cage, and the second cage being configured to maintain a separation between the second impeller and the inner wall of the vena cava.

For some applications:

the apparatus further includes a control unit configured to control rotation of the first and second impellers, and the first and second impellers are configured, by rotating, to lower pressure within the subject's renal veins by:

the first impeller pumping blood through the vena cava in a downstream direction, and the second impeller pumping blood through the vena cava in an upstream direction.

For some applications, the first and second impellers are configured to pump fluid in opposite directions from one another by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications:

the apparatus further includes a control unit configured to control rotation of the first and second impellers, and the first and second impellers are configured to pump fluid in opposite directions from one another, by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications, the apparatus further includes a motor configured to cause the first and second impellers to pump fluid in opposite directions from one another by rotating the first and second impellers in the same direction as one another.

For some applications, the catheter is configured to be placed within a blood vessel of a subject, and the first and second impellers are configured to generate a region within the blood vessel that is of lower blood pressure than elsewhere within the blood vessel by pumping blood away from a region of the blood vessel between the first and second impellers.

For some applications, the catheter is configured to be placed within a main vein of a subject into which blood flows from a tributary venous system such that:

the first impeller is placed in the main vein, downstream of the tributary venous system; and the second impeller is placed in the main vein, upstream of the tributary venous system.

For some applications, the catheter is configured to be placed within a blood vessel of a subject, and the first and second impellers are configured to generate a region within the blood vessel that is of higher blood pressure than elsewhere within the blood vessel by pumping blood toward a region of the blood vessel between the first and second impellers.

For some applications, the catheter is configured to be placed within a main artery of a subject that supplies a branching arterial system that branches from the main artery such that:

the first impeller is placed in the main artery, downstream of the branching arterial system; and the second impeller is placed in the main artery, upstream of the branching arterial system.

There is additionally provided, in accordance with some applications of the present invention, apparatus including:

a catheter configured to be placed inside a blood vessel of a subject;

a blood pump disposed on the catheter; and an occlusion element disposed on the catheter, and configured to partially occlude the subject's blood vessel, longitudinal centers of the blood pump and the occlusion element being separated from one another by a distance of at least 3 cm, the distance being measured along a longitudinal axis of the catheter.

For some applications, the blood pump includes an impeller configured to pump blood through the subject's blood vessel by rotating.

For some applications, the apparatus further includes a cage, the impeller being disposed inside the cage, and the cage being configured to maintain a separation between the impeller and an inner wall of the blood vessel.

For some applications, the catheter is configured to be placed within a vena cava of a subject such that the blood pump is disposed downstream of junctions of the vena cava with all renal veins of the subject, and such that the occlusion element is disposed upstream of junctions of the vena cava with all renal veins of the subject.

For some applications, the blood pump is configured to lower pressure within the subject's renal veins by pumping blood through the vena cava in a downstream direction.

For some applications, the catheter is configured to be placed within the subject's vena cava by being inserted via a vein of the subject selected from the group consisting of: a subclavian vein, a jugular vein, and a femoral vein.

For some applications, the blood pump includes an impeller configured to pump blood through the vena cava by rotating.

For some applications, the apparatus further includes a cage, the impeller being disposed inside the cage, and the cage being configured to maintain a separation between the impeller and an inner wall of the vena cava.

For some applications, the blood pump and the occlusion element are configured to generate a region within the blood vessel that is of lower blood pressure than elsewhere within the blood vessel by the blood pump pumping away from a region of the blood vessel between the blood pump and the occlusion element.

For some applications, the catheter is configured to be placed within a main vein of a subject into which blood flows from a tributary venous system such that:
the blood pump is placed in the main vein, downstream of the tributary venous system; and
the occlusion element is placed in the main vein, upstream of the tributary venous system.

For some applications, the blood pump and occlusion element are configured to generate a region within the blood vessel that is of higher blood pressure than elsewhere within the blood vessel by the blood pump pumping blood toward a region of the blood vessel between the blood pump and the occlusion element.

For some applications, the catheter is configured to be placed within a main artery of a subject that supplies a branching arterial system that branches from the main artery such that:
the occlusion element is placed in the main artery, downstream of the branching arterial system; and
the blood pump is placed in the main artery, upstream of the branching arterial system.

There is further provided, in accordance with some applications of the present invention, a method for use with a tributary venous system of a subject that flows into a main vein of the subject, the method including:
reducing blood pressure within the tributary venous system by:
placing a first pump in the main vein, downstream of the tributary venous system, and activating the first pump to pump blood through the main vein in a downstream direction; and
placing a second pump in the main vein, upstream of the tributary venous system, and activating the second pump to pump blood through the main vein in an upstream direction.

For some applications, the first and second pumps are disposed upon a single catheter, and placing the first and second pumps in the main vein includes inserting a distal end of the catheter into the main vein.

For some applications:
the main vein includes a vena cava of the subject,
the tributary venous system includes a renal venous system of the subject,
placing the first pump in the main vein, downstream of the tributary venous system, includes placing the first pump in the vena cava, downstream of junctions of the vena cava with all renal veins of the subject,
placing the second pump in the main vein, upstream of the tributary venous system, includes placing the second pump in the vena cava, upstream of the junctions of the vena cava with all of the subject's renal veins,
the method further includes identifying the subject as suffering from a condition selected from the group consisting of: cardiac dysfunction, congestive heart failure, reduced renal blood flow, increased renal vascular resistance, arterial hypertension, and kidney dysfunction, and
reducing pressure within the tributary venous system includes reducing pressure within renal veins of the subject, in response to the identifying.

For some applications, the first and second pumps are disposed upon a single catheter, and placing the first and second pumps in the vena cava includes inserting a distal end of the catheter into the subject's vena cava.

For some applications, inserting the distal end of the catheter into the subject's vena cava includes inserting the distal end of the catheter into the subject's vena cava via a vein of the subject selected from the group consisting of: a subclavian vein, a jugular vein, and a femoral vein.

For some applications:
placing the first pump in the main vein includes placing a first impeller in the main vein, downstream of the tributary venous system; and
placing the second pump in the main vein includes placing a second impeller in the main vein, upstream of the tributary venous system.

For some applications:
placing the first impeller inside the main vein includes inserting the first impeller into the main vein while the first impeller is disposed inside a cage that is configured to maintain a separation between the first impeller and an inner wall of the main vein; and
placing the second impeller inside the main vein includes inserting the second impeller into the main vein while the second impeller is disposed inside a cage that is configured to maintain a separation between the second impeller and the inner wall of the main vein.

For some applications, activating the first pump to pump blood through the main vein in the downstream direction includes rotating the first impeller in a given direction, and activating the second pump to pump blood through the main vein in the upstream direction includes rotating the second impeller in the same given direction, as viewed from an external reference point.

For some applications, the first and second impellers are of opposing-handedness to one another, and are disposed upon a single catheter such that the first and second impellers face in opposite directions from another, and placing the first and second pumps in the vena cava includes inserting a distal end of the catheter into the subject's vena cava.

For some applications, rotating the first and second impellers in the given direction includes using a single motor to rotate the first and second impellers.

There is additionally provided, in accordance with some applications of the present invention, a method for use with a tributary venous system of a subject that flows into a main vein of the subject, the method including:
reducing blood pressure within the tributary venous system by:
placing a pump in the main vein, downstream of the tributary venous system, and activating the pump to pump blood through the main vein in a downstream direction; and
placing an occlusion element in the main vein at a location within the main vein that is upstream of the tributary venous system, such that the occlusion element partially occludes the main vein at the location.

For some applications, placing the occlusion element in the main vein includes placing a balloon in the main vein.

For some applications, placing the occlusion element in the main vein includes placing a frame that is covered with a blood-impermeable material in the main vein.

For some applications, the pump and the occlusion element are disposed upon a single catheter, and placing the pump and the occlusion element in the main vein includes inserting a distal end of the catheter into the main vein.

For some applications:
the main vein includes a vena cava of the subject, the tributary venous system includes a renal venous system of the subject, placing the pump in the main vein, downstream of the tributary venous system includes placing the pump in the vena cava, downstream of junctions of the vena cava with all renal veins of the subject, placing the occlusion element in the main vein at the location within the main vein that is upstream of the tributary venous system includes placing the occlusion element in the vena cava upstream of the junctions of the vena cava with all of the subject's renal veins, the method further includes identifying the subject as suffering from a condition selected from the group consisting of: cardiac dysfunction, congestive heart failure, reduced renal blood flow, increased renal vascular resistance, arterial hypertension, and kidney dysfunction, and reducing pressure within the tributary venous system includes reducing pressure within renal veins of the subject, in response to the identifying.

For some applications, the pump and the occlusion element are disposed upon a single catheter, and placing the pump and the occlusion element in the vena cava includes inserting a distal end of the catheter into the vena cava.

For some applications, inserting the distal end of the catheter into the vena cava includes inserting the distal end of the catheter into the vena cava via a vein of the subject selected from the group consisting of: a subclavian vein, a jugular vein, and a femoral vein.

For some applications, placing the pump in the main vein includes placing an impeller in the main vein, downstream of the tributary venous system.

For some applications, placing the impeller inside the main vein includes inserting the first impeller into the main vein while the impeller is disposed inside a cage that is configured to maintain a separation between the first impeller and an inner wall of the main vein.

There is further provided, in accordance with some applications of the present invention, a method including:

identifying a subject as suffering from a condition selected from the group consisting of: cardiac dysfunction, congestive heart failure, reduced renal blood flow, increased renal vascular resistance, arterial hypertension, and kidney dysfunction; and in response thereto, reducing blood pressure within renal veins of the subject, by:
 placing at least one pump in a vena cava of the subject; and
 generating a low-pressure region within the subject's vena cava, adjacent to junctions of the vena cava with the subject's renal veins, blood pressure within the low-pressure region being lower than central venous pressure of the subject,
 by activating the at least one pump to pump blood away from the region.

For some applications, generating the low-pressure region within the subject's vena cava includes:
 placing a blood-impermeable sleeve in the subject's vena cava, such that a downstream end of the sleeve is coupled to a wall of the vena cava at a first location that is downstream of all of the renal veins of the subject, and such that an upstream end of the sleeve is coupled to the wall of the vena cava at a second location that is upstream of all the renal veins of the subject; and
 activating the pump to pump blood from a location outside the sleeve that is in fluid communication with the subject's renal veins, to a location within the vena cava that is in fluid communication with an interior of the sleeve.

For some applications:
 placing the at least one pump in the subject's vena cava includes:
  placing a first pump in the vena cava, downstream of junctions of the vena cava with all renal veins of the subject; and
  placing a second pump in the vena cava, upstream of the junctions of the vena cava with all of the subject's renal veins; and
 generating the low-pressure region within the subject's vena cava includes:
  activating the first pump to pump blood through the vena cava in a downstream direction; and
  activating the second pump to pump blood through the vena cava in an upstream direction.

For some applications:
 placing the at least one pump in the subject's vena cava includes:
  placing a pump in the vena cava, downstream of junctions of the vena cava with all renal veins of the subject; and
  placing an occlusion element in the vena cava at a location within the vena cava that is upstream of the junctions of the vena cava with all of the subject's renal veins, such that the occlusion element partially occludes the vena cava at the location; and
 generating the low-pressure region within the subject's vena cava includes activating the pump to pump blood through the vena cava in a downstream direction.

For some applications, placing the occlusion element in the vena cava includes placing a balloon in the vena cava.

For some applications, placing the occlusion element in the vena cava includes placing in the vena cava a frame that is covered with a blood-impermeable material.

There is additionally provided, in accordance with some applications of the present invention, apparatus including:
 a catheter configured to be placed inside a blood vessel of a subject;
 a first impeller disposed on the catheter;
 a second impeller disposed on the catheter, proximally to the first impeller; and
 a support structure disposed upon the catheter such that a longitudinal center of the support structure is disposed between the first and second impellers, the support structure being configured to support an inner wall of the blood vessel in an open configuration in a region between the first and second impellers.

For some applications, the longitudinal center of the support structure is disposed equidistantly from the first and second impellers.

For some applications, the support structure extends at least from a longitudinal center of the first impeller to a longitudinal center of the second impeller.

For some applications, the first and second impellers are of opposing-handedness with respect to one another, and are disposed upon the catheter such that the impellers face opposite directions from one another.

For some applications, the catheter is configured to be placed within a vena cava of a subject such that the first impeller is disposed downstream of junctions of the vena cava with all renal veins of the subject, and such that the second impeller is disposed upstream of junctions of the vena cava with all renal veins of the subject.

For some applications, the catheter is configured to be placed within the subject's vena cava by being inserted via a vein of the subject selected from the group consisting of: a subclavian vein, a jugular vein, and a femoral vein.

For some applications:

the apparatus further includes a first cage, the first impeller being disposed inside the first cage, and the first cage being configured to maintain a separation between the first impeller and an inner wall of the vena cava; and the apparatus further includes a second cage, the second impeller being disposed inside the second cage, and the second cage being configured to maintain a separation between the second impeller and the inner wall of the vena cava.

For some applications, the first and second cages are integrally formed with the support structure.

For some applications, the first and second cages are separately formed from the support structure.

For some applications:

the apparatus further includes a control unit configured to control rotation of the first and second impellers, and the first and second impellers are configured, by rotating, to lower pressure within the subject's renal veins by:

the first impeller pumping blood through the vena cava in a downstream direction, and the second impeller pumping blood through the vena cava in an upstream direction.

For some applications, the first and second impellers are configured to pump fluid in opposite directions from one another by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications, the catheter is configured to be placed within a vena cava of a subject such that the first impeller is disposed upstream of junctions of the vena cava with all renal veins of the subject, and such that the second impeller is disposed downstream of junctions of the vena cava with all renal veins of the subject.

For some applications, the catheter is configured to be placed within the subject's vena cava by being inserted via a vein of the subject selected from the group consisting of: a subclavian vein, and a jugular vein.

For some applications:

the apparatus further includes a first cage, the first impeller being disposed inside the first cage, and the first cage being configured to maintain a separation between the first impeller and an inner wall of the vena cava; and the apparatus further includes a second cage, the second impeller being disposed inside the second cage, and the second cage being configured to maintain a separation between the second impeller and the inner wall of the vena cava.

For some applications, the first and second cages are integrally formed with the support structure.

For some applications, the first and second cages are separately formed from the support structure.

For some applications:

the apparatus further includes a control unit configured to control rotation of the first and second impellers, and the first and second impellers are configured, by rotating, to lower pressure within the subject's renal veins by:

the first impeller pumping blood through the vena cava in an upstream direction, and the second impeller pumping blood through the vena cava in a downstream direction.

For some applications, the first and second impellers are configured to pump fluid in opposite directions from one another by the first and second impellers rotating in the same direction as one another, as viewed from an external reference point.

For some applications, the first and second impellers are of opposing handedness with respect to one another, and are disposed upon the catheter such that the impellers face opposite directions from one another.

For some applications:

the apparatus further includes a control unit configured to control rotation of the first and second impellers, and the first and second impellers are configured to pump fluid in opposite directions from one another, by the first and second impellers rotating in the same direction as one another, as viewed from an external reference point.

For some applications, the first and second impellers are of opposing-handedness with respect to one another, and are disposed upon the catheter such that the impellers face opposite directions from one another.

For some applications, the catheter is configured to be placed within a blood vessel of a subject, and the first and second impellers are configured to generate a region within the blood vessel that is of lower blood pressure than elsewhere within the blood vessel by pumping blood away from a region of the blood vessel between the first and second impellers.

For some applications, the catheter is configured to be placed within a main vein of a subject into which blood flows from a tributary venous system such that:

the first impeller is placed in the main vein, downstream of the tributary venous system; and the second impeller is placed in the main vein, upstream of the tributary venous system.

For some applications, the catheter is configured to be placed within a main vein of a subject into which blood flows from a tributary venous system such that:

the first impeller is placed in the main vein, upstream of the tributary venous system; and the second impeller is placed in the main vein, downstream of the tributary venous system.

There is additionally provided, in accordance with some applications of the present invention, apparatus including:

a catheter configured to be placed inside a blood vessel of a subject;

a first pump disposed on the catheter and configured to pump blood through the blood vessel in a first direction;

a second pump disposed on the catheter, proximally to the first pump, and configured to pump blood through the blood vessel in a second direction that is opposite to the first direction; and a support structure disposed upon the catheter such that a longitudinal center of the support structure is disposed between the first and second pumps, the support structure being configured to support an inner wall of the blood vessel in an open configuration in a region between the first and second pumps.

For some applications, the longitudinal center of the support structure is disposed equidistantly from the first and second impellers.

For some applications, the support structure extends at least from a longitudinal center of the first pump to a longitudinal center of the second pump.

There is further provided, in accordance with some applications of the present invention, a method for use with a tributary venous system of a subject that flows into a main vein of the subject, the method including:

reducing blood pressure within the tributary venous system by:

placing a first pump in the main vein, downstream of the tributary venous system, and activating the pump to pump blood through the main vein in a downstream direction;

placing a second pump in the main vein, upstream of the tributary venous system, and activating the pump to pump blood through the main vein in an upstream direction; and placing a support structure within the main vein, such that a longitudinal center of the support structure is disposed between the first and second pump, and such that the support structure supports an inner wall of the main vein in an open configuration during the pumping of the blood by the first and second pumps.

For some applications, the first and second pumps are disposed upon a single catheter, and placing the first and second pumps in the main vein includes inserting a distal end of the catheter into the main vein.

For some applications:

the main vein includes a vena cava of the subject, the tributary venous system includes a renal venous system of the subject, placing the first pump in the main vein, downstream of the tributary venous system includes placing the first pump in the vena cava, downstream of junctions of the vena cava with all renal veins of the subject, placing the second pump in the main vein, upstream of the tributary venous system includes placing the second pump in the vena cava, upstream of the junctions of the vena cava with all of the subject's renal veins, the method further includes identifying the subject as suffering from a condition selected from the group consisting of: cardiac dysfunction, congestive heart failure, reduced renal blood flow, increased renal vascular resistance, arterial hypertension, and kidney dysfunction, and reducing pressure within the tributary venous system includes reducing pressure within renal veins of the subject, in response to the identifying.

For some applications, the first and second pumps are disposed upon a single catheter, and placing the first and second pumps in the vena cava includes inserting a distal end of the catheter into the subject's vena cava.

For some applications, inserting the distal end of the catheter into the subject's vena cava includes inserting the distal end of the catheter into the subject's vena cava via a vein of the subject selected from the group consisting of: a subclavian vein, a jugular vein, and a femoral vein.

For some applications:

placing the first pump in the main vein includes placing a first impeller in the main vein, downstream of the tributary venous system; and placing the second pump in the main vein includes placing a second impeller in the main vein, upstream of the tributary venous system.

For some applications:

placing the first impeller inside the main vein includes inserting the first impeller into the main vein while the first impeller is disposed inside a first cage that is configured to maintain a separation between the first impeller and an inner wall of the main vein; and placing the second impeller inside the main vein includes inserting the second impeller into the main vein while the second impeller is disposed inside a second cage that is configured to maintain a separation between the second impeller and the inner wall of the main vein.

For some applications:

placing the first impeller inside the main vein includes inserting the first impeller into the main vein the first cage being integrally formed with the support structure; and placing the second impeller inside the main vein includes inserting the second impeller into the main vein the second cage being integrally formed with the support structure.

For some applications:

placing the first impeller inside the main vein includes inserting the first impeller into the main vein the first cage being separately formed with respect to the support structure; and placing the second impeller inside the main vein includes inserting the second impeller into the main vein the second cage being separately formed with respect to the support structure.

For some applications, activating the first pump to pump blood through the main vein in the downstream direction includes rotating the first impeller in a given direction, and activating the second pump to pump blood through the main vein in the upstream direction includes rotating the second impeller in the same given direction, as viewed from an external reference point.

For some applications, the first and second impellers are of opposing-handedness to one another, and are disposed upon a single catheter such that the first and second impellers face in opposite directions from another, and placing the first and second pumps in the vena cava includes inserting a distal end of the catheter into the subject's vena cava.

For some applications, rotating the first and second impellers in the given direction includes using a single motor to rotate the first and second impellers.

There is further provided, in accordance with some applications of the present invention, a method for use with a tributary venous system of a subject that flows into a main vein of the subject, the method including:

reducing blood pressure within the tributary venous system by:

placing a first pump in the main vein, downstream of the tributary venous system, and activating the pump to pump blood through the main vein in a downstream direction;

placing an occlusion element in the main vein at a location within the main vein that is upstream of the tributary venous system, such that the occlusion element partially occludes the main vein at the location; and placing a support structure within the main vein, such that a longitudinal center of the support structure is disposed between the first pump and the occlusion element, and such that the support structure supports an inner wall of the main vein in an open configuration during pumping of the blood by the first pump.

For some applications:

the main vein includes a vena cava of the subject, the tributary venous system includes a renal venous system of the subject, placing the first pump in the main vein, downstream of the tributary venous system includes placing the first pump in the vena cava, downstream of junctions of the vena cava with all renal veins of the subject, placing the occlusion element in the main vein at the location within the main vein that is upstream of the tributary venous system includes placing the occlusion element in the vena cava upstream of the junctions of the vena cava with all of the subject's renal veins, the method further includes identifying the subject as suffering from a condition selected from the group consisting of: cardiac dysfunction, congestive heart failure, reduced renal blood flow, increased renal vascular resistance, arterial hypertension, and kidney dysfunction, and reducing pressure within the tributary venous system includes reducing pressure within renal veins of the subject, in response to the identifying.

There is additionally provided, in accordance with some applications of the present invention, apparatus including:
  a catheter;
  a first impeller disposed on the catheter;
  a second impeller disposed on the catheter, proximally to the first impeller; and
  a telescopic shaft extending between the first and second impellers, a length of the telescopic shaft being adjustable.

There is further provided, in accordance with some applications of the present invention, a method, including:
  manufacturing an impeller by:
    cutting a tube such that the cut tube defines a structure having first and second end portions at proximal and distal ends of the structure, the end portions being connected to one another by a plurality of elongate elements;
    causing the elongate elements to radially expand and form helical elongate elements, by axially compressing the structure;
    coupling respective reinforcement elements to each of the helical elongate elements, such that each of the reinforcement elements extends from the helical elongate element toward a longitudinal axis of the structure; and
    coupling a material to the helical elongate elements, such that each of the helical elongate elements with the material coupled thereto defines a respective blade of the impeller,
    the reinforcement elements being configured to reinforce central portions of respective blades of the impeller.

For some applications:
  the method further includes coupling an axial element to the structure such that the axial element extends along a longitudinal axis of the structure, and
  coupling respective reinforcement elements to each of the helical elongate elements, includes coupling respective reinforcement elements to each of the helical elongate elements such that each of the reinforcement elements extends from a respective helical elongate element toward the axial element.

For some applications, the method further includes, subsequent to coupling the material to the helical elongate elements, removing the axial element from the structure.

For some applications:
  the method further includes coupling axial elements to each of the helical elongate elements, such that each of the axial elements extends from a proximal end of a respective helical elongate element to a distal end of the helical elongate element, and
  coupling respective reinforcement elements to each of the helical elongate elements, includes coupling respective reinforcement elements to each of the helical elongate elements such that each of the reinforcement elements extends from a respective helical elongate element toward a corresponding one of the axial elements.

For some applications, the method further includes, subsequent to coupling the material to the helical elongate elements, removing the axial elements from the structure.

There is additionally provided, in accordance with some applications of the present invention, apparatus including:
  an impeller, including:
    an impeller frame that includes proximal and distal end portions and a plurality of helical elongate elements that wind from the proximal end portion to the distal end portion; and
    a material that is coupled to the helical elongate elements, such that each of the helical elongate elements with the material coupled thereto defines a respective blade of the impeller,
    each of the impeller blades including a reinforcement element extending from the helical elongate element of the blade toward a longitudinal axis of the impeller frame, and configured to reinforce a central portion of the impeller blade.

There is further provided, in accordance with some applications of the present invention, a method, including:
  manufacturing an expandable impeller by:
    cutting a tube such that the cut tube defines a structure having first and second end portions at proximal and distal ends of the structure, the end portions being connected to one another by a plurality of elongate elements;
    causing the elongate elements to radially expand and form helical elongate elements, by axially compressing the structure;
    coupling axial elements to each of the helical elongate elements, such that each of the axial elements extends from a proximal end of a respective helical elongate element to a distal end of the helical elongate element; and
    coupling a material to the helical elongate elements, such that each of the helical elongate elements, with a film of the material extending from the helical elongate element to the axial element, defines a respective blade of the impeller.

For some applications, the method further includes, subsequent to coupling the material to the helical elongate elements, removing the axial elements from the structure.

For some applications, the method further includes mounting the structure upon an axial shaft.

For some applications, mounting the structure upon the axial shaft includes mounting the structure upon a telescopic axial shaft.

There is additionally provided, in accordance with some applications of the present invention, apparatus including:
  an impeller, including:
    an impeller frame that includes proximal and distal end portions and a plurality of helical elongate elements that wind from the proximal end portion to the distal end portion;
    a material that is coupled to the helical elongate elements, such that each of the helical elongate elements with the material coupled thereto defines a respective blade of the impeller; and
    an axially-elongatable telescopic shaft disposed along a longitudinal axis of the impeller frame.

The present invention will be more fully understood from the following detailed description of embodiments thereof, taken together with the drawings, in which:

BRIEF DESCRIPTION OF THE DRAWINGS

FIGS. 11A, 11B, and 11C are schematic illustrations of a blood-pump catheter placed within a subject's vena cava, an upstream pump being disposed upon the catheter, distally to a downstream pump, the upstream and downstream pumps being disposed at respective separations from one another in FIGS. 11A, 11B, and 11C, in accordance with some applications of the present invention;

FIGS. 14A, 14B, and 14C are graphs showing the pressure drop recorded in models of a subject's left and right renal veins, during experiments that were conducted using blood pumps, in accordance with some applications of the present invention.

DETAILED DESCRIPTION OF EMBODIMENTS

Figure 1A:
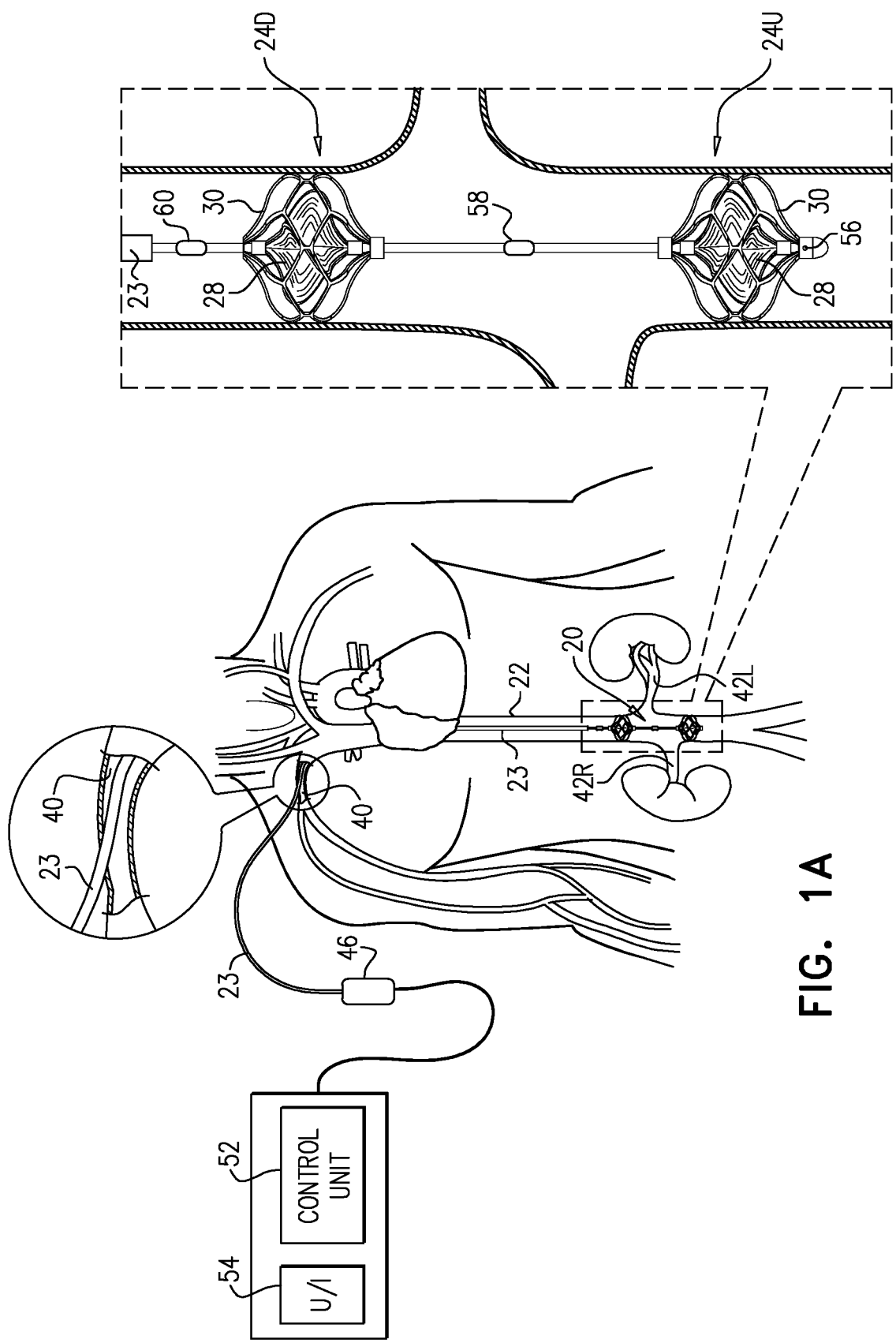
FIGS. 1A, 1B, 1C, and 1D are schematic illustrations of a blood-pump catheter placed within a subject's vena cava, an upstream pump being disposed upon the catheter, distally to a downstream pump, in accordance with some applications of the present invention.
Figure 1B:
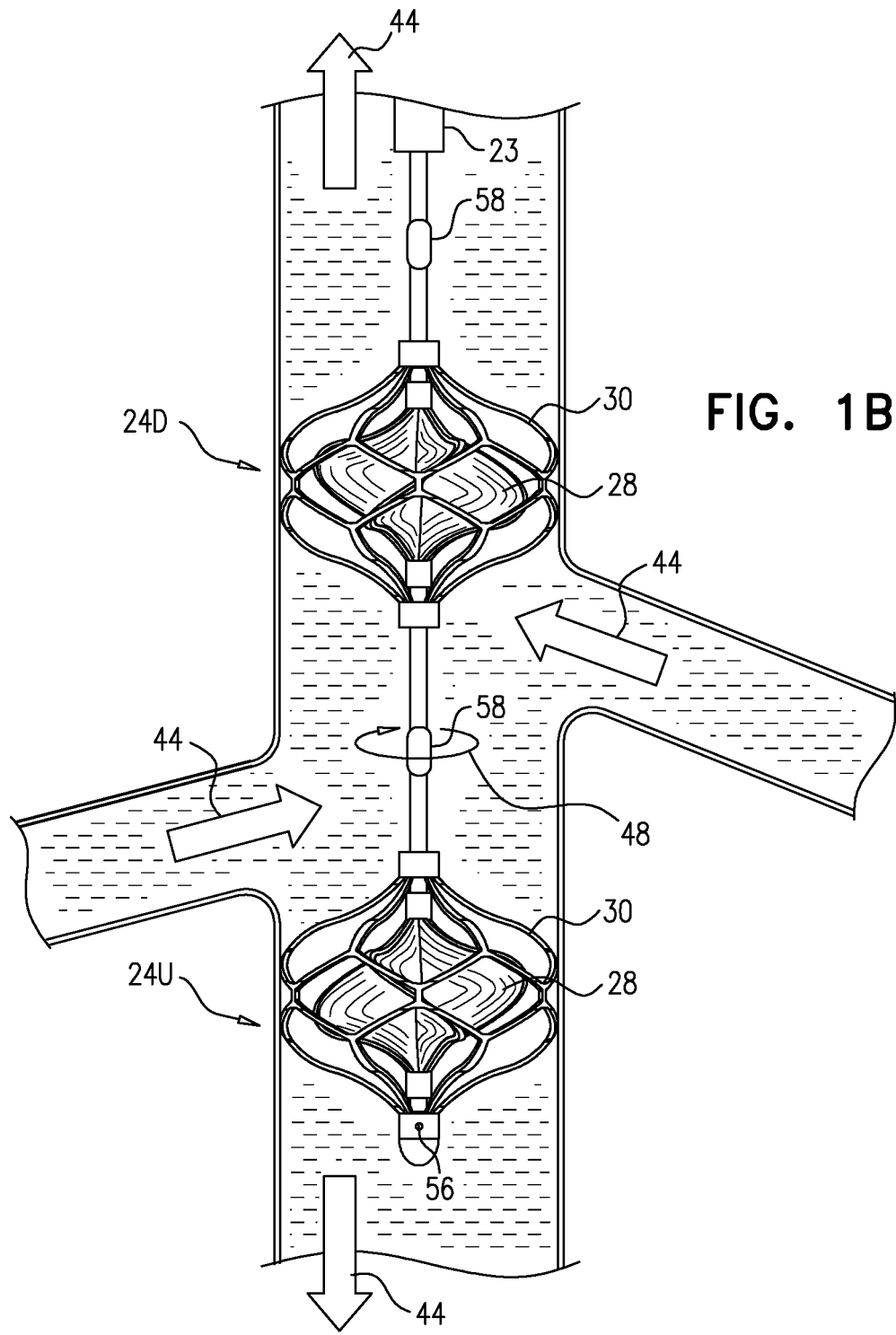

Reference is made to FIGS. 1A-D, which are schematic illustrations of a blood-pump catheter 20 placed within a subject's vena cava 22, via a guide catheter 23, an upstream pump 24U being disposed upon the catheter, distally to a downstream pump 24D, in accordance with some applications of the present invention. Typically, the distal portion of blood-pump catheter 20 is configured to be straight, when the catheter is in a non-constrained state, such that both the upstream and the downstream pumps are disposed along the axis of the catheter, within the vena cava.

Each of the upstream and downstream pumps 24U and 24D typically includes a radially-expandable impeller 28 disposed inside a radially-expandable impeller cage 30. Typically, impeller 28 and cage 30 are shape-set such as to assume radially expanded configurations thereof in the absence of any radially constraining force acting upon the impeller and the cage. Further typically, an engagement mechanism engages the impeller and the cage with respect to one another, such that in response to the cage becoming radially constrained, the impeller becomes radially constrained, e.g., in accordance with apparatus and methods described in described in WO 14/141284 to Schwammenthal, which is incorporated herein by reference.

It is noted that the term "impeller" is used herein to denote a bladed rotor, as shown in 1A-D, for example. When the bladed rotor is placed inside a blood vessel (such as vena cava 22) and rotated, the bladed rotor functions as an impeller, by modifying the flow of blood through the blood vessel, and/or by generating a pressure difference between the upstream end and the downstream end of the impeller.

It is noted that reference numeral 24 is generally used to denote a blood pump in the present application. When a pump that is placed upstream is being referred to, reference numeral 24U is used, and when a pump that is placed downstream is being referred to, reference numeral 24D is used. Similarly, reference numeral 28 is generally used to denote an impeller in the present application. When an impeller that is placed upstream is being referred to, reference numeral 28U is used, and when an impeller that is placed downstream is being referred to, reference numeral 28D is used.

Blood-pump catheter 20 is typically placed inside the subject's vena cava 22, and operated therein, in order to provide acute treatment of a subject suffering from cardiac dysfunction, congestive heart failure, low renal blood flow, high renal vascular resistance, arterial hypertension, diabetes, and/or kidney dysfunction. For example, the blood-pump catheter may be placed inside the subject's vena cava, and operated therein, for a period of more than one hour (e.g., more than one day), less than one week (e.g., less than four days), and/or between one hour and one week (e.g., between one day and four days). For some applications, the blood-pump catheter is chronically placed inside the subject's vena cava in order to provide chronic treatment of a subject suffering from cardiac dysfunction, congestive heart failure, low renal blood flow, high renal vascular resistance, arterial hypertension, diabetes, and/or kidney dysfunction. For some applications, a course of treatment is applied to a subject over several weeks, several months, or several years, during which the blood-pump catheter is intermittently placed inside the subject's vena cava, and the subject is intermittently treated in accordance with the techniques described herein. For example, the subject may be intermittently treated at intervals of several days, several weeks, or several months.

For some applications, blood-pump catheter 20 is inserted into vena cava 22, via the subject's subclavian vein 40, as shown in FIG. 1A. Typically, the blood-pump catheter is inserted under fluoroscopic imaging. Alternatively, the blood-pump catheter is inserted under ultrasound imaging, such as to reduce exposure of the subject to radiation and/or contrast agent. The catheter is placed into the vena cava such that upstream pump 24U is disposed upstream of the junctions of the vena cava and all of the subject's renal veins 42, and such that downstream pump 24D is disposed downstream of the junctions of the vena cava and all of the subject's renal veins. Typically, the upstream pump is configured to pump blood through the vena cava in the upstream direction, away from the renal veins, and the downstream pump is configured to pump blood through the vena cava in the downstream direction, away from the renal veins.

The effect of both of pumps 24U and 24D pumping blood in the above-described manner is that, between the pumps, and adjacent to the junctions of the vena cava with the renal veins, there is a low-pressure region of the vena cava, within which blood pressure is lower than the subject's central venous pressure. Functionally, this region may be viewed as a compartment within the vena cava within which blood pressure is controlled (by controlling pumps 24U and 24D), regardless of the blood pressure elsewhere within the vena cava. This typically increases blood flow from the renal veins into the vena cava, lowers pressure within the subject's renal veins, and causes renal perfusion to increase. The effect of pumps 24U and 24D on blood flow through the renal veins and the vena cava is indicated by arrows 44 in FIG. 1B.

As described hereinabove, the effect of operating blood pumps 24U and 24D is that between the pumps there is a low-pressure region of the vena cava. However, typically, the pumps are operated simultaneously such that the pressure within other portions of the vena cava is substantially unchanged relative to when blood-pump catheter 20 is not in operation. For example, the pumps are typically operated simultaneously such that the pressure within the vena cava downstream of downstream pump 24D is not substantially increased relative to when blood-pump catheter 20 is not in operation. Similarly, the pumps are typically operated simultaneously such that the pressure within the vena cava upstream of upstream pump 24U is not substantially increased relative to when blood-pump catheter 20 is not in operation. This is because the pumps are typically operated simultaneously such that outside of the region between the two pumps, the effects of the pumping by the upstream and downstream pumps cancel each other with respect to pressure. It is noted that there is likely to be some increase in the pressure within the vena cava downstream of downstream pump and upstream of upstream pump due to the increased blood flow from the renal veins into the vena cava.

Similarly, the pumps are typically operated simultaneously such that venous return to the vena cava from regions upstream of the upstream pump and downstream from the downstream pump is substantially unchanged relative to when blood-pump catheter 20 is not in operation. In this manner, the pumps are typically operated simultaneously such as to have a generally synergistic effect on pressure and flow in the region between the pumps, but to have an antagonistic effect on pressure and flow outside of the region, such that, outside of the region, the effects of the two pumps typically substantially cancel each other out.

Typically, blood-pump catheter 20 pumps blood in a manner that enhances the rate of blood flow through the renal veins and into the vena cava, but does not cause a substantial change in the direction of the blood flow relative to the natural direction of flow through the renal veins, or from the renal veins to the vena cava (i.e., relative to blood flow in the absence of pumping by the blood-pump catheter). That is to say, the blood-pump catheter pumps blood in the downstream direction through the renal veins and then directly into the portion of the vena cava that is adjacent to the renal veins, rather than, for example, pumping the blood from the renal veins into a different portion of the subject's veins (such as, an upstream location within the vena cava). It is noted that, due to the pumping of the downstream pump in the downstream direction, there is likely to be some blood flow from the renal veins to the portion of the vena cava that is below the renal veins. Further typically, blood-pump catheter 20 enhances blood flow through the renal veins without removing blood from the subject's venous system into a non-venous receptacle, such as an artificial lumen of a blood pump.

As described hereinabove, typically blood-pump catheter 20 is placed inside the vena cava of a subject suffering from cardiac dysfunction, congestive heart failure, low renal blood flow, high renal vascular resistance, arterial hypertension, diabetes, and/or kidney dysfunction. Typically, operating the blood-pump catheter in the vena cava of such a subject causes a lowering and flattening of the subject's renal vein pressure profile, even though the subject's central venous pressure is elevated, e.g., as described with reference to FIG. 4B of WO 14/141284 to Schwammenthal, which is incorporated herein by reference.

Typically, due to the reduction in pressure in the renal vein that is caused by the pumping of blood by blood-pump catheter 20, perfusion of the kidney increases. In turn, this may cause pressure in the renal veins to rise relative to the pressure in the renal veins immediately subsequent to initiation of the pumping, due to increased blood flow into the renal vein. Typically, even after perfusion of the kidney increases, the pump is configured to maintain the pressure in the renal vein at a lower value than the pressure in the renal vein before the initiation of the pumping. For some applications, in addition to lowering the subject's renal vein pressure, and/or increasing perfusion of the subject's kidney, blood-pump catheter 20 performs ultrafiltration on the subject's blood.

It is noted that, for some applications, due to the reduction in pressure in the renal vein that is caused by the pumping of blood by blood-pump catheter 20, the subject's renal vascular resistance decreases, in accordance with physiological mechanisms that are described, for example, in an article by Haddy et al., entitled "Effect of elevation of intraluminal pressure on renal vascular resistance" (Circulation Research, 1956), which is incorporated herein by reference. It is further noted that a treatment of the subject that increases renal perfusion by increasing blood pressure in the subject's renal arteries would typically not effect the aforementioned physiological mechanisms.

Typically, when blood-pump catheter 20 is used to reduce pressure in the subject's renal veins, it is expected that there will be an improved responsiveness by the subject to administration of diuretics to the subject, due to the reduction in renal venous pressure. Therefore, for some applications, a reduced dosage of diuretics may be administered to the subject relative to a dosage of diuretics that would be administered to the subject in the absence of performing the techniques described herein. Alternatively, a regular dosage of diuretics may be administered to the subject, but the diuretics may have a greater effect on the subject, due to the reduction in renal venous pressure.

Typically, high central venous pressure leads to a high level of blood pressure within the heart, which in turn leads to the release of atrial natriuretic peptide (ANP) and B-type natriuretic peptide (BNP) by the subject, both of which act as natural diuretics. For some applications, when blood-pump catheter 20 is used to reduce pressure in the subject's renal veins, there is expected to be an improved responsiveness by the subject to the release of the natural diuretics by the subject, due to the reduction in renal venous pressure. For some applications, since the subject's central venous pressure is not lowered by using blood-pump catheter 20, it is expected that the subject will continue to release atrial natriuretic peptide (ANP) and B-type natriuretic peptide (BNP), even while the subject's renal venous pressure is reduced by the use of the blood pumps. Thus, for some applications, using blood-pump catheter 20 may result in the subject continuing to release atrial natriuretic peptide (ANP) and B-type natriuretic peptide (BNP), as well as resulting in the effectiveness of the aforementioned natural diuretics being greater than the effectiveness of the diuretics in the absence of the use of blood-pump catheter 20.

Typically, each of upstream and downstream pumps 24U and 24D includes an impeller 28, for example, an impeller as shown in any one of FIGS. 7A-C, 8A-C, 9A-C, and/or 10A-C, and/or any one of the impellers described in WO 14/141284 to Schwammenthal, which is incorporated herein by reference. In accordance with respective applications, impeller 28 may have a single blade, two blades (e.g., as described in WO 14/141284 to Schwammenthal, which is incorporated herein by reference, and as shown in FIGS. 8A-C and FIGS. 9A-C), three blades (e.g., as described in WO 14/141284 to Schwammenthal, which is incorporated herein by reference, and as shown in FIGS. 7A-C and FIGS. 10A-C), or more than three blades. For some applications, one or both of blood pumps 24U and 24D includes more than one impeller. Typically, ceteris paribus, by using more than one impeller in at least one of the pumps, in order to generate a given flow of blood with the pump, the force that impacts each of the impellers within the pump is smaller than if a single impeller were to be used in the pump.

For some applications, one or both of the pumps includes radially expandable cage 30. Typically, cage 30 is configured to hold open the inner wall of the vena cava and to separate the inner wall of the vena cava from the impeller, such that the vena cava does not become injured by the impeller. As described hereinabove, typically, impeller 28 and 30 are shape-set such as to assume radially expanded configurations thereof in the absence of any radially constraining force acting upon the impeller and/or the cage. Further typically, an engagement mechanism engages the impeller and the cage with respect to one another, such that in response to the cage becoming radially constrained the impeller becomes radially constrained, e.g., in accordance with apparatus and methods described in described in WO 14/141284 to Schwammenthal, which is incorporated herein by reference.

Figure 1C:
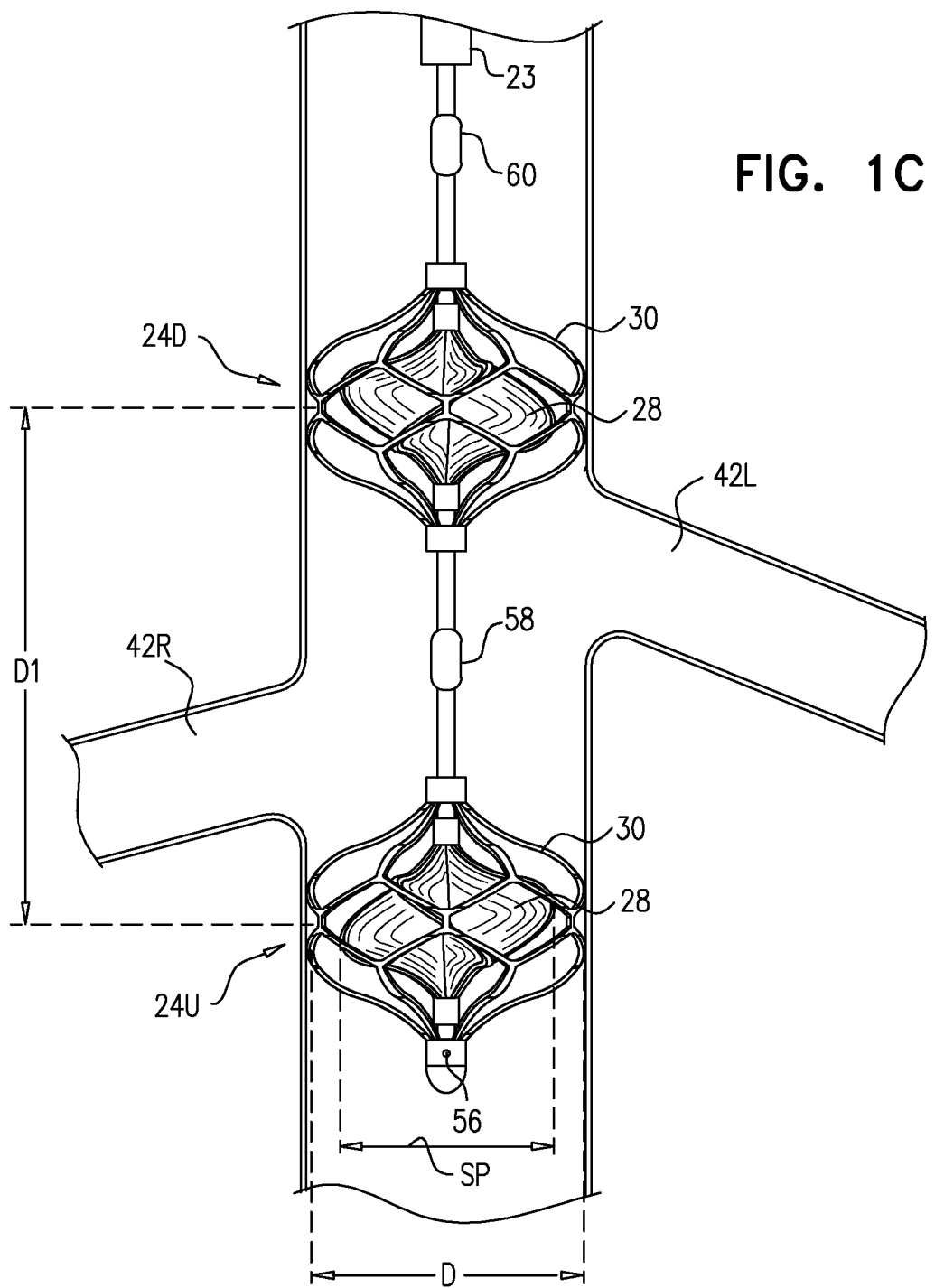

Referring now to FIG. 1C, typically, when blood-pump catheter 20 is placed inside vena cava 22, impeller 28 and cage 30 are substantially not radially constrained, due to the relatively low radial force exerted by the vena cava wall on the cage. Typically, a span SP of impeller 28, when the impeller is in a non-constrained configuration thereof inside the vena cava is more than 14 mm (e.g., more than 16 mm), and/or less than 28 mm (e.g., less than 22 mm), e.g., 14-28 mm, or 16-22 mm Typically, a diameter D of cage 30, when the cage is in a non-constrained configuration thereof inside the vena cava is more than 14 mm (e.g., more than 16 mm), and/or less than 40 mm (e.g., less than 35 mm), e.g., 14-40 mm, or 16-35 mm. Further typically, when blood-pump catheter 20 is used to enhance blood flow from the renal veins into the subject's vena cava, as described herein, a longitudinal distance D1 between centers of the impellers of the upstream and downstream pumps, measured along the longitudinal axis of the catheter, is typically more than 3 cm (e.g., more than 6 cm), and/or less than 18 cm (e.g., less than 14 cm), e.g., 3-18 cm, or 6-14 cm. For some applications, distance D1 is adjustable and is set based upon measurements that are performed upon a subject, as described in further detail hereinbelow, with reference to FIGS. 11A-C.

Typically, impellers of pumps 24U and 24D are coupled to one or more motors 46 (FIG. 1A), which impart rotational motion to the impellers, via one or more shafts, the shaft(s) being housed inside blood-pump catheter 20. In accordance with respective applications, the motors are disposed outside of the subject's body (as shown), or are placed inside the subject's body (not shown).

For some applications, in order for the impellers to pump blood in opposite directions (i.e., in order for the upstream impeller to pump blood upstream, and the downstream pump to pump blood downstream), the impellers are rotated in opposite directions from one another, as viewed from an external reference point.

Figure 1D:
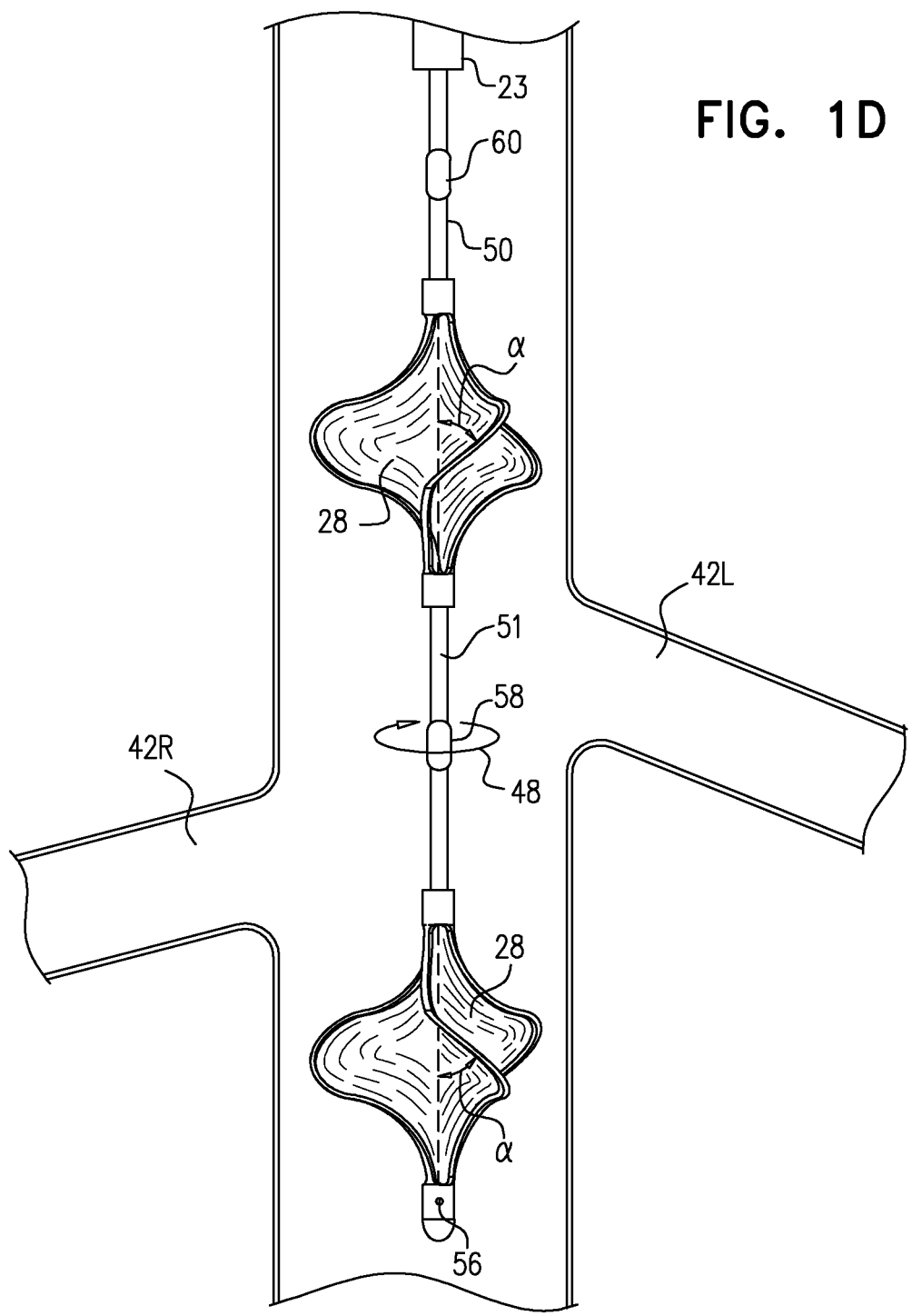

Referring now to FIG. 1D, typically, impellers 28 of upstream and downstream pumps 24U and 24D are rotated in the same rotational direction as one another, as viewed from an external reference point (e.g., in the direction of arrow 48 (i.e., clockwise), or counterclockwise), but the impellers are disposed on the catheter such that the rotation of the impellers in this direction of rotation causes the impellers to pump blood in respective, opposite directions. It is noted that the rotational direction of the impellers "as viewed from an external reference point" should be interpreted to mean the direction of rotational motion of the impellers as observed from any point that is not undergoing the same rotational motion as either of the impellers. (For illustrative purposes, FIG. 1D shows the impellers in the absence of the cages, although typically, the impellers are used together with cages, as described hereinabove.)

Typically, for such applications, a single motor is used to rotate both of the impellers. A shaft 50 is used to impart the rotational motion from the motor to the proximal impeller. An additional shaft 51, which is in series with shaft 50, couples the proximal impeller to the distal impeller and imparts the rotational motion from the proximal impeller to the distal impeller. For some applications, by using a single series of shafts to impart rotation to impellers 28 of both upstream and downstream pumps 24U and 24D, the diameter of blood-pump catheter 20 is reduced relative to if parallel shafts were used, in order to impart rotation to the upstream and downstream impellers.

For some applications, the angles and/or orientations of the impeller blades of impellers 28 of upstream and downstream pumps 24U and 24D may be such as to cause the impellers to pump blood in respective, opposite directions. For some applications, as shown in FIG. 1D, each propeller is shaped and/or oriented in the mirror image of the other, the axis of reflection being orthogonal to the longitudinal axes of the impellers. Typically, the upstream and downstream impellers are of opposing handedness to one another, a first one of the impellers being a left-handed impeller, and the other one of the impellers being a right-handed impeller. It is generally the case that impellers of opposing handedness that are positioned parallel to one another, facing the same direction as one another, and rotating in opposite rotational directions from one another, generate flow in the same direction as one another. In accordance with the present invention, the upstream and downstream impellers are typically disposed upon shaft 51 such that the impellers are facing in opposite directions to one another. As described hereinabove, the impellers are typically rotated in the same rotational direction as one another, as viewed from an external reference point. The result of the impellers (a) being of opposing handedness to one another, and (b) facing in opposite directions, is that, when the impellers are rotated in the same direction as one another about an axis defined by shaft 51, the impellers pump blood in opposite directions from one another.

Typically, the blades of the downstream impeller are oriented such that, as the downstream impeller rotates in the direction of arrow 48, the downstream impeller pumps in the downstream direction. The blades of the upstream impeller are oriented such that, as the upstream impeller rotates in the direction of arrow 48, the upstream impeller pumps in the upstream direction.

As described in further detail hereinbelow, for some applications, upstream and downstream pumps 24U and 24D and blood-pump catheter 20 are placed within a main artery upstream and downstream of bifurcations of the artery with one or more branching arterial systems that branch from the main artery and supply a given organ, mutatis mutandis. For such applications, the blades of the downstream impeller are oriented such that, as the downstream impeller is rotated, the downstream impeller pumps in the upstream direction (toward the bifurcations). The blades of the upstream impeller are oriented such that, as the upstream impeller rotates is rotated, the upstream impeller pumps in the downstream direction (toward the bifurcations), such that blood flow into the branching arterial system is increased, thereby increasing perfusion of the organ.

For some applications, the blades of the impellers of the upstream and downstream pumps are configured to pump blood in the same direction as one another (e.g., in the antegrade direction). For example, the impellers may be of the same handedness as one another, placed upon catheter 20 such that the impellers are facing in the same direction as one another, and rotated in the same direction as one another, as viewed from an external reference point. Alternatively, the two impellers may be of opposing handedness to one another, placed within the vena cava such that the two impellers are facing in the same direction as one another, and rotated in opposite directions to one another, as viewed from an external reference point.

For some applications, blades of the upstream and downstream impellers are disposed at an angle alpha with respect to the longitudinal axes of the impellers, the blades of the respective impellers being oriented in opposite directions. For some applications, angle alpha is greater than 15 degrees (e.g., greater than 25 degrees), and/or less than 45 degrees (e.g., less than 35 degrees), e.g. 15-45 degrees, or 25-35 degrees.

For some applications, impellers 28 of upstream and downstream pumps 24U and 24D are rotated at respective rotation rates, in order to cause the pumping of blood in the upstream and downstream directions to be performed at respective rates. Alternatively, the impellers are rotated at the same rotation rate (and, typically, in the same direction), but the impellers are sized, shaped, and/or oriented such that the rate at which blood is pumped, respectively, in the upstream and downstream directions, by the respective impellers, is not equal.

Typically, a control unit 52 and a user interface 54 are disposed outside the subject's body. Further typically, the control unit receives inputs from one or more pressure sensors 56, 58, and/or 60, e.g., as shown in FIGS. 1A-D.

In accordance with some applications:

(a) a pressure sensor 56 is disposed on the upstream side of upstream blood pump 24U and is configured to measure pressure within the vena cava upstream of the low-pressure region of the vena cava, which is typically indicative of venous pressure within the subject's lower body;

(b) a pressure sensor 58 disposed between the two blood pumps, and is configured to measure pressure within the low-pressure region of the vena cava between the two blood pumps, which is typically indicative of blood pressure within the subject's renal veins; and/or (c) a pressure sensor 60 is disposed on the downstream side of downstream blood pump 24D and is configured to measure pressure within the vena cava downstream of the low-pressure region of the vena cava, which is typically indicative of the subject's central venous pressure close to the subject's right heart.

For some applications, blood-pump catheter 20 includes pressure sensor 58 disposed between the two blood pumps, and is configured to measure pressure within the low-pressure region of the vena cava between the two blood pumps, which is typically indicative of blood pressure within the subject's renal veins, and the blood-pump catheter does not include pressure sensor 56, or pressure sensor 60.

For some applications, control unit 52 controls pumps 24U and 24D, e.g., by controlling rotation of impellers 28, responsively to one or more of the above-described inputs. Typically, user interface 54 displays the subject's current lower-body venous pressure, renal venous pressure, and/or central venous pressure, based upon the signals generated by sensors 56, 58, and/or 60. Typically, based upon the current values of the subject's lower-body venous pressure, renal venous pressure, and/or central venous pressure, a user (such as a healthcare professional) inputs a target value for the subject's renal venous pressure, via the user interface. In response thereto, control unit 52 controls the speed of the rotation of the impellers, such that the impellers pump blood away from the renal veins at a flow rate that is such as to reduce the renal venous pressure toward the target level, as indicated by the user. For some applications, in response a signal received from sensor 60 indicating that the central venous pressure is at the target renal venous pressure, the control unit stops the impellers rotating. For some applications, the control unit receives an input from an additional sensor (such as a flow sensor and/or an oxygen-saturation sensor, and/or a thermal flow sensor, e.g., as described with reference to FIGS. 22Ai-22Cii of WO 14/141284 to Schwammenthal, which is incorporated herein by reference), and the control unit controls the speed of the rotation of the impellers responsively to an input from the additional sensor.

It is noted that control unit 52 typically includes a computer processor that comprises circuitry and that is configured to execute the actions described herein. Typically, the operations described herein that are performed by the computer processor transform the physical state of a memory, which is a real physical article that is in communication with the computer processor, to have a different magnetic polarity, electrical charge, or the like, depending on the technology of the memory that is used. Control unit 52 is typically a hardware device programmed with computer program instructions to produce a special-purpose computer. For example, when programmed to perform the techniques described herein, control unit 52 typically acts as a special-purpose, renal-venous-pressure-modulating computer processor.

It is further noted that user interface 54 typically includes any type of user interface configured to receive inputs from a user and/or to provide outputs to the user. For example, the user interface may include one or more input devices (such as a keyboard, a mouse, a trackball, a joystick, a touchscreen monitor, a touchpad, a voice-command interface, a smartphone, a tablet computer, and/or other types of input devices that are known in the art), and/or one or more output devices (such as a monitor, an audio output device, a smartphone, a tablet computer, and/or other types of output devices that are known in the art).

Figure 2:
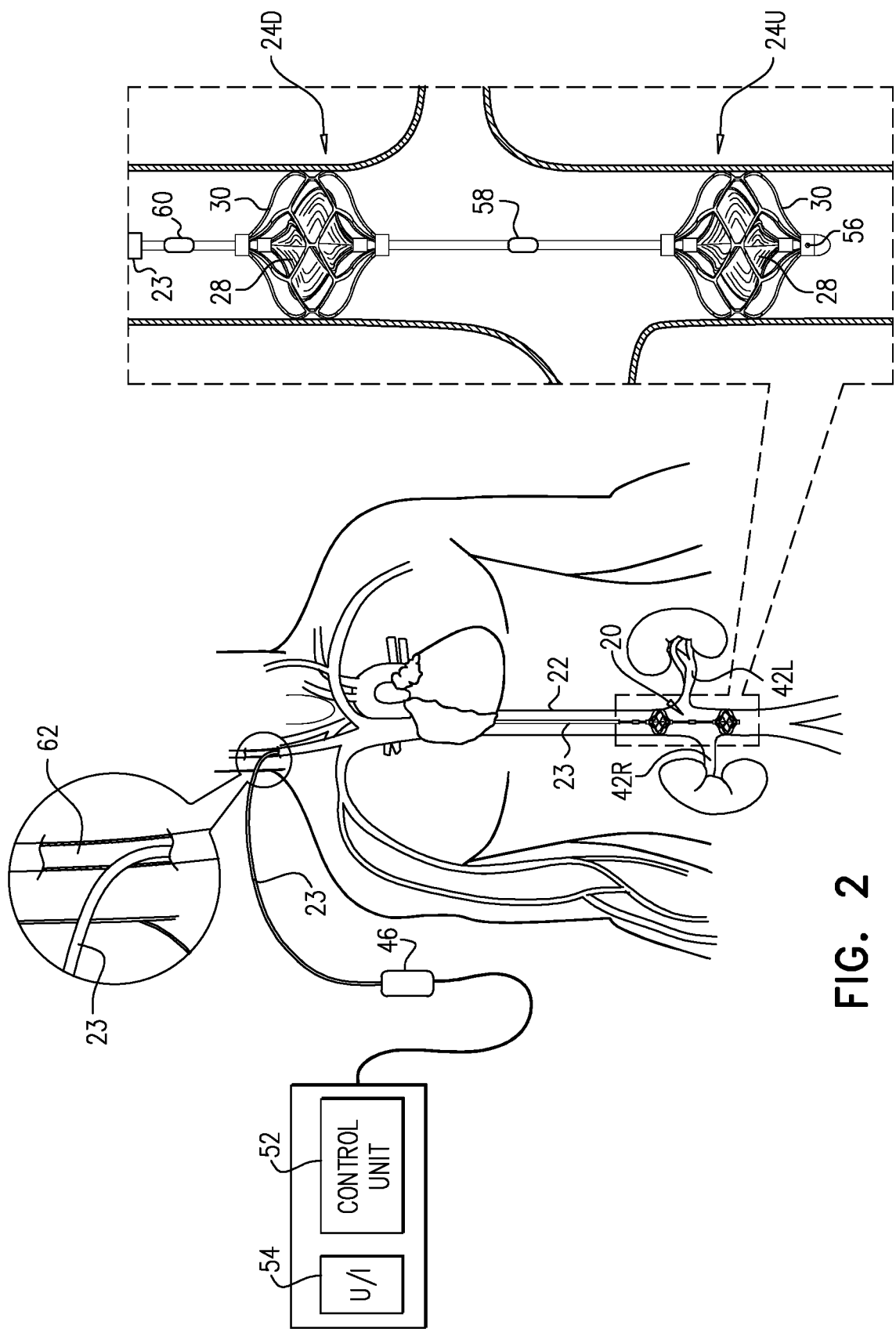
FIG. 2 is a schematic illustration of the catheter of FIGS. 1A, 1B, 1C, and 1D inserted into the subject's vena cava via the subject's right jugular vein, in accordance with some applications of the present invention.

Reference is now made to FIG. 2, which is a schematic illustration of blood-pump catheter 20 being inserted into the subject's vena cava 22 via the subject's right jugular vein 62 (through guide catheter 23), in accordance with some applications of the present invention. For some applications, instead of being inserted via the subclavian vein (as shown in FIG. 1A, for example), blood-pump catheter 20 is inserted into the vena cava via the subject's right jugular vein, or via another vein that is above the subject's inferior vena cava. In all other aspects, blood-pump catheter 20 and the functioning thereof are generally as described with reference to FIGS. 1A-D.

Figure 3:
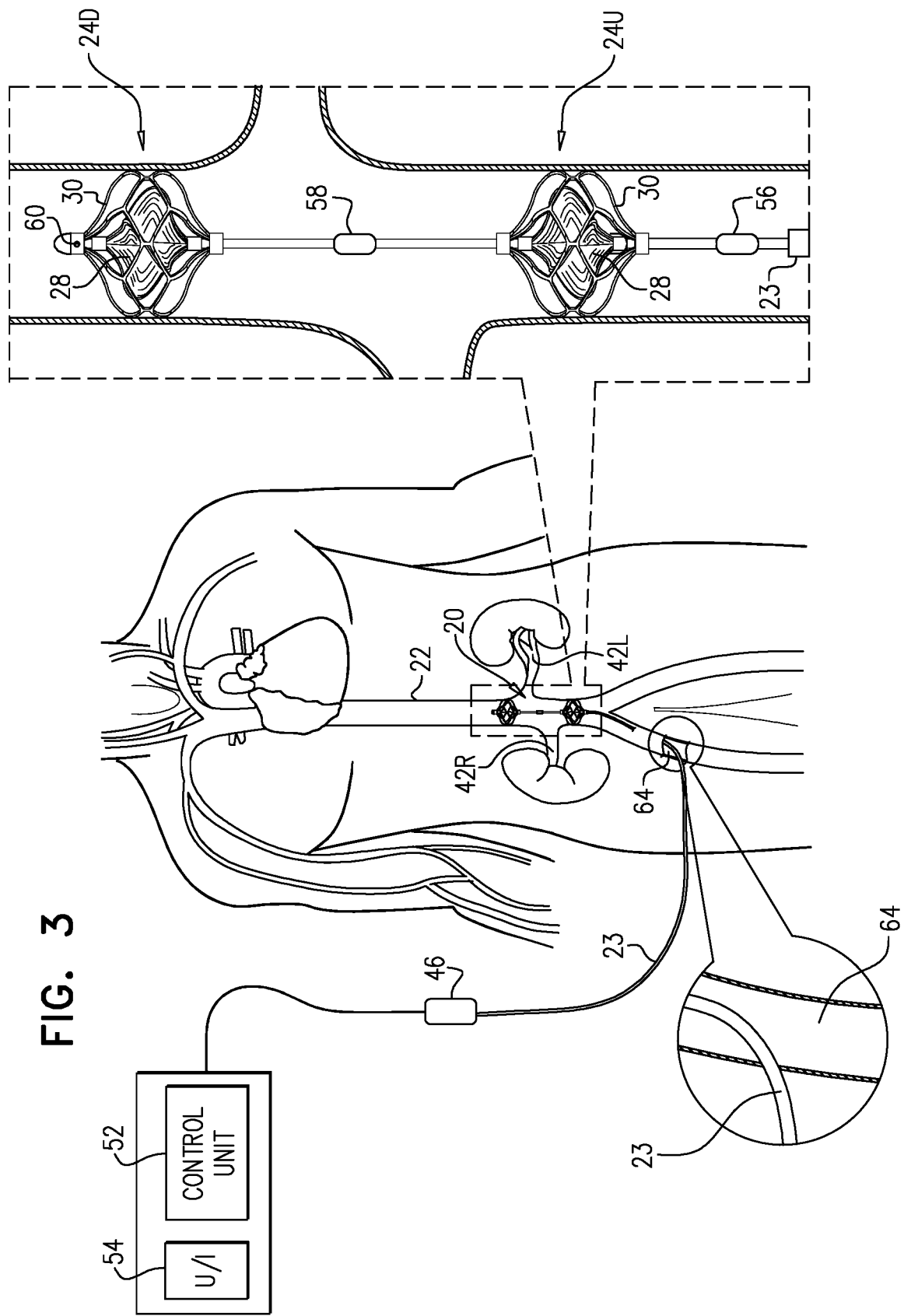
FIG. 3 is a schematic illustration of a blood-pump catheter inserted into a subject's vena cava via the subject's femoral vein, a downstream pump being disposed upon the catheter distally to an upstream pump, in accordance with some applications of the present invention.

Reference is now made to FIG. 3, which is a schematic illustration of blood-pump catheter 20 being inserted into the subject's vena cava 22 via the subject's femoral vein 64 (through guide catheter 23), downstream pump 24D being disposed upon the catheter distally to upstream pump 24U, in accordance with some applications of the present invention. For some applications, instead of being inserted via the subclavian vein (as shown in FIG. 1A, for example), blood-pump catheter 20 is inserted into the vena cava, via the subject's femoral vein 64, or via another vein that is below the subject's inferior vena cava. Typically, downstream blood pump 24D is disposed on blood-pump catheter 20 distally to upstream blood pump 24U. Blood-pump catheter 20 is configured to be placed within the vena cava, such that the upstream pump is disposed upstream of the junctions of the vena cava with all of the subject's renal veins 42, and such that the downstream pump is disposed downstream of the junctions of the vena cava with all of the subject's renal veins. Other than the dispositions of the upstream and downstream blood pumps with respect to blood-pump catheter 20, blood-pump catheter 20, as shown in FIG. 3, and the functioning thereof, is generally similar to that described with reference to blood-pump catheter 20 as shown in FIGS. 1A-D.

Figure 4:
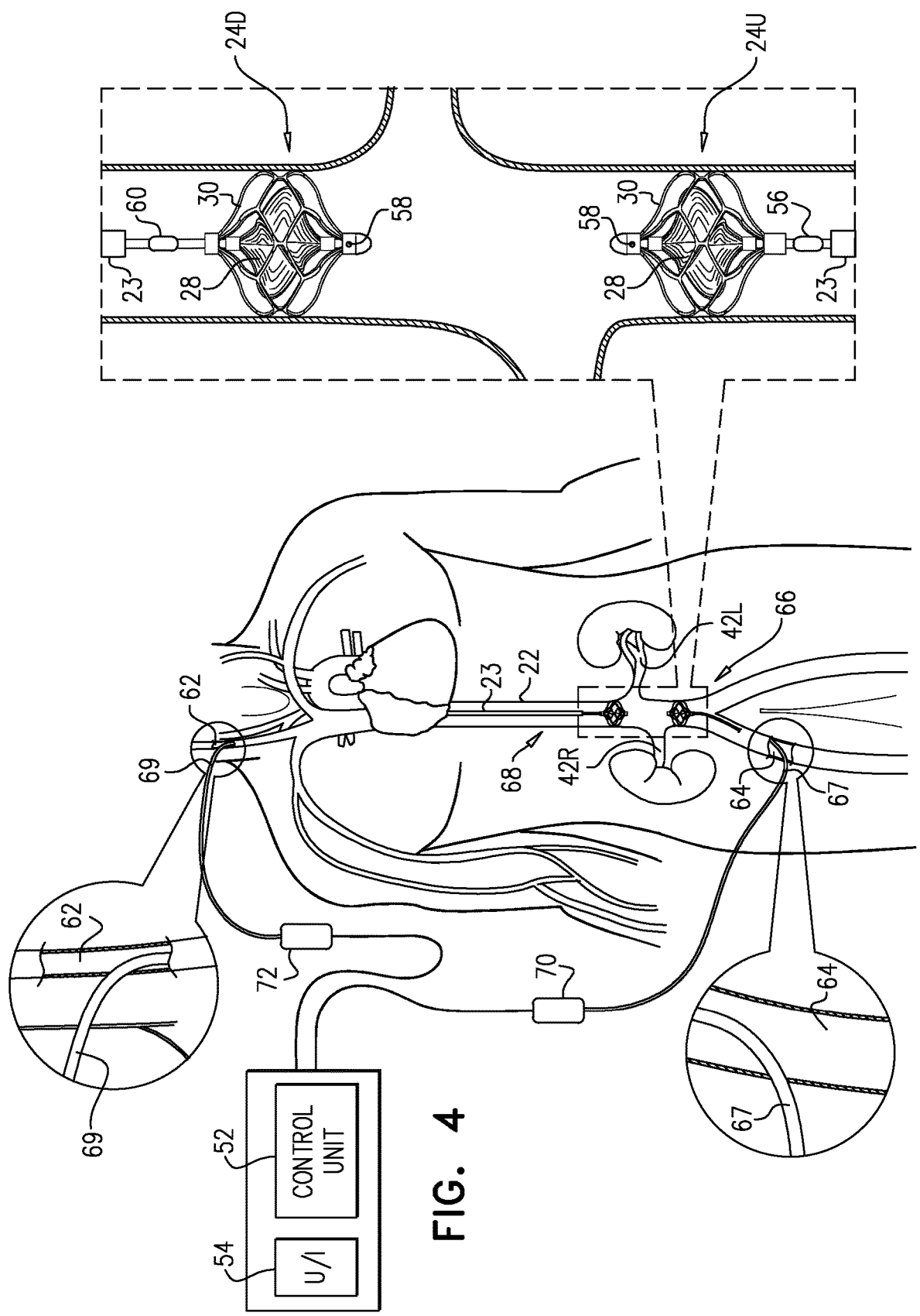
FIG. 4 is a schematic illustration of upstream and downstream pumps disposed on respective blood-pump catheters, in accordance with some applications of the present invention.

Reference is now made to FIG. 4, which is a schematic illustration of upstream and downstream pumps 24U and 24D being disposed on respective catheters 66 and 68, in accordance with some applications of the present invention. For some applications, a first catheter 66 is inserted into vena cava 22 through a guide catheter 67 that is inserted via the subject's femoral vein 64, or via another vein that is below the subject's inferior vena cava. Upstream blood pump 24U is disposed on the first catheter, and is configured to be placed within the vena cava upstream of the junctions of the vena cava with all of the subject's renal veins, and to pump blood through the vena cava in the manner described hereinabove. A second catheter 68 is inserted into the vena cava through a guide catheter 69 that is inserted via the subject's jugular vein 62 (as shown), via the subclavian vein (not shown), or via a different vein that is above the subject's inferior vena cava. Downstream blood pump 24D is disposed on the second catheter, and is configured to be placed within the vena cava downstream of the junctions of the vena cava with all of the subject's renal veins, and to pump blood through the vena cava in the manner described hereinabove.

For applications in which the upstream and downstream blood pumps include impellers, typically, respective motors 70 and 72 are used to control rotation of the impellers. Further typically, control unit 52 controls both pumps (e.g., by controlling the rates of rotation of the impellers). For some applications, pressure sensors 56, 58 and 60 are disposed upon the first and/or second catheters, and are configured to detect indications of, respectively, lower body venous pressure, renal venous pressure, and central venous pressure. The control unit is configured to control the operation of the upstream and downstream pumps responsively to the detected indications, in accordance with the techniques described hereinabove.

Figure 5B:
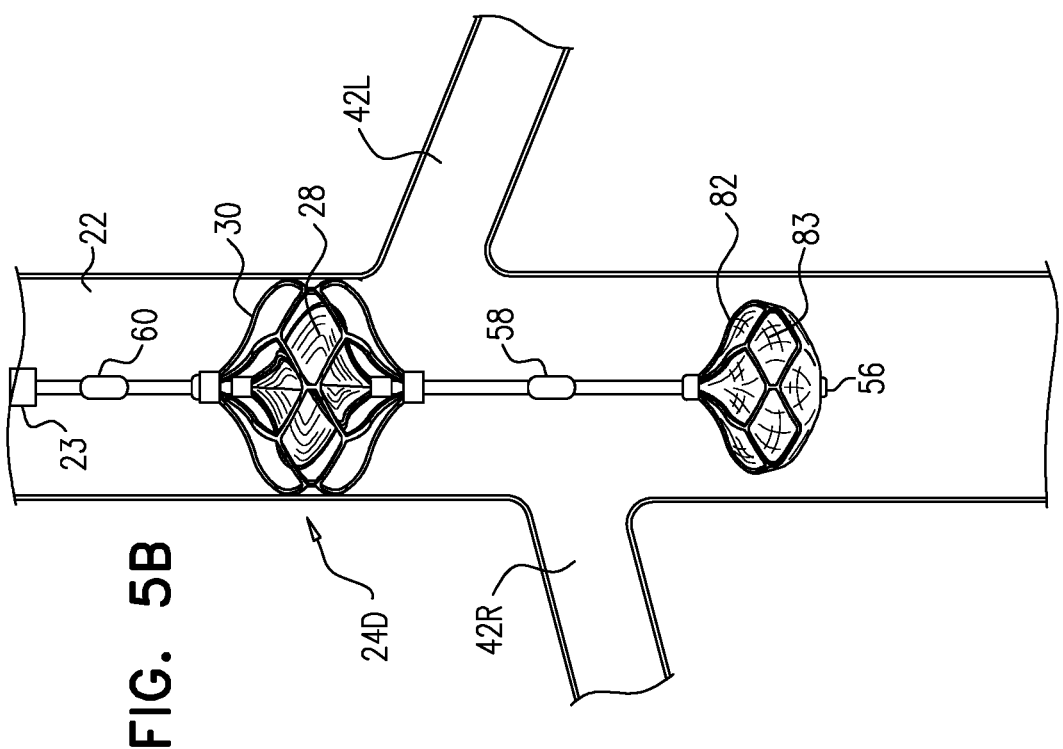
FIGS. 5A and 5B are schematic illustrations of a catheter that includes a downstream pump and an occlusion element, such as a balloon (FIG. 5A), or a covered frame (FIG. 5B), in accordance with some applications of the present invention.
Figure 5A:
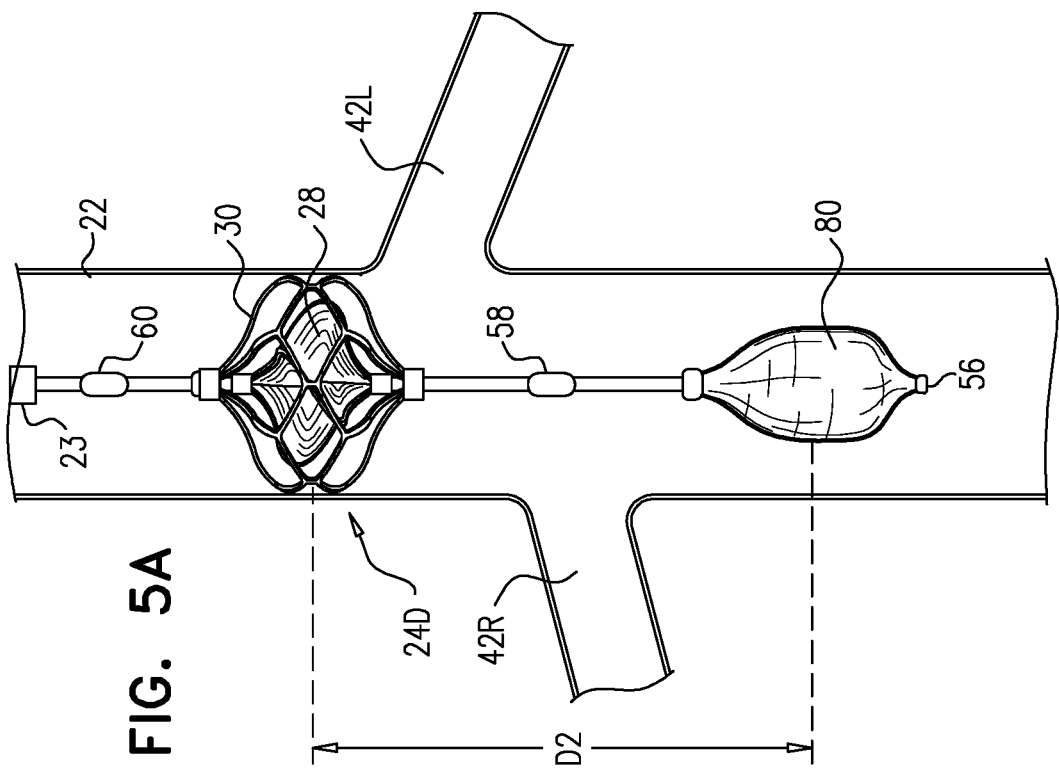

Reference is now made to FIGS. 5A-B, which are schematic illustrations of blood-pump catheter 20, the catheter including downstream pump 24D and an occlusion element, such as a balloon 80 (FIG. 5A), or a covered frame 82 (FIG. 5B), in accordance with some applications of the present invention. For some applications, downstream pump is placed inside vena cava 22, downstream of the junctions of the vena cava with all of the subject's renal veins. The downstream pump pumps blood through the vena cava, in the downstream direction, away from the junctions of the vena cava with the renal veins, in the manner described hereinabove. As an alternative to, or in addition to using an upstream pump as described hereinabove, the occlusion element is placed inside the vena cava upstream of the junctions of the vena cava with the subject's renal veins. Typically, the occlusion element is configured to partially occlude the subject's vena cava upstream of the junctions of the vena cava with the subject's renal veins. The occlusion element is configured to partially occlude the subject's vena cava such that, in response to the pumping of the downstream blood pump, there is not a substantial increase of blood flow from the subject's lower body toward the subject heart, but such that a region of low pressure within the vena cava is generated, between the occlusion element and the downstream blood pump, within which the blood pressure is lower than the subject's central venous pressure. Typically, by generating a region of low pressure, blood flow from the renal veins into the vena cava increases, thereby lowering renal blood pressure and enhancing renal perfusion. It is noted that the occlusion element is configured to partially occlude, but not to totally occlude, the vena cava, in such a manner as to generate a region of low pressure within the vena cava, but to allow a substantial flow of blood through the vena cava.

When blood-pump catheter 20 is used to enhance blood flow from the renal veins into the subject's vena cava, as described herein, a longitudinal distance D2 between the longitudinal center of the impeller of the downstream pump and the longitudinal center of the occlusion element, measured along the longitudinal axis of the catheter, is typically more than 3 cm (e.g., more than 6 cm), and/or less than 18 cm (e.g., less than 14 cm), e.g., 3-18 cm, or 6-14 cm.

As used in the present application, including in the claims, a "longitudinal axis" of a structure is the set of all centroids of cross-sectional sections of the structure along the structure. Thus the cross-sectional sections are locally perpendicular to the longitudinal axis, which runs along the structure. (If the structure is circular in cross-section, the centroids correspond with the centers of the circular cross-sectional sections.) As used in the present application, including in the claims, the term "longitudinal center" denotes the center of a structure along the direction of the structure's longitudinal axis.

For some applications, the occlusion element is balloon 80, as shown in FIG. 5A. Alternatively or additionally, the occlusion element is covered frame 82, as shown in FIG. 5B. For example, the frame may be a rigid frame made of a shape-memory element (such as nitinol) that is covered with a blood-impermeable material 83 (e.g., polyester, polyurethane, and/or a different polymer).

As described hereinabove, typically, the occlusion element is configured to partially occlude the vena cava upstream of the junctions of the vena cava with the subject's renal veins. For some applications, the diameter to which the occlusion element is expanded is controllable. For example, inflation of the balloon may be controllable, or the stent may be expandable (e.g., by heating the stent, or by applying an electrical current to the stent). For some applications, the extent to which the occlusion element occludes the vena cava is controlled by a control unit (e.g., control unit 52) responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of WO 14/141284 to Schwammenthal, which is incorporated herein by reference), and/or in response to an input from a user. For some applications, the rate at which pump 24D pumps blood away from the renal veins (e.g., the rate at which impeller 28 of the pump is rotated), as well as the extent to which the occlusion element occludes the vena cava is controlled by a control unit responsively to the blood pressure detected by blood pressure sensor 56, 58, and/or 60, in response to an input from a different sensor (such as a flow sensor and/or an oxygen-saturation sensor, and/or a thermal flow sensor, e.g., as described with reference to FIGS. 22Ai-Cii of WO 14/141284 to Schwammenthal, which is incorporated herein by reference), and/or in response to an input from a user.

Although FIGS. 5A and 5B show the downstream blood pump and the occlusion element disposed on a catheter that is inserted into the vena cava from above the junctions of the vena cava with the subject's renal veins (e.g., via the subject's subclavian vein or jugular vein), for some applications, the downstream blood pump and the occlusion element are disposed on a catheter that is inserted into the vena cava from below the junctions of the vena cava with the subject's renal veins (e.g., via the subject's femoral vein), mutatis mutandis. Alternatively or additionally, the occlusion element is disposed on a first catheter which is inserted into the vena cava from below the junctions of the vena cava with the subject's renal veins (e.g., via the subject's femoral vein), and the downstream blood pump is disposed on a second catheter, which inserted into the vena cava from above the junctions of the vena cava with the subject's renal veins (e.g., via the subject's subclavian vein, or jugular vein).

Figure 6:
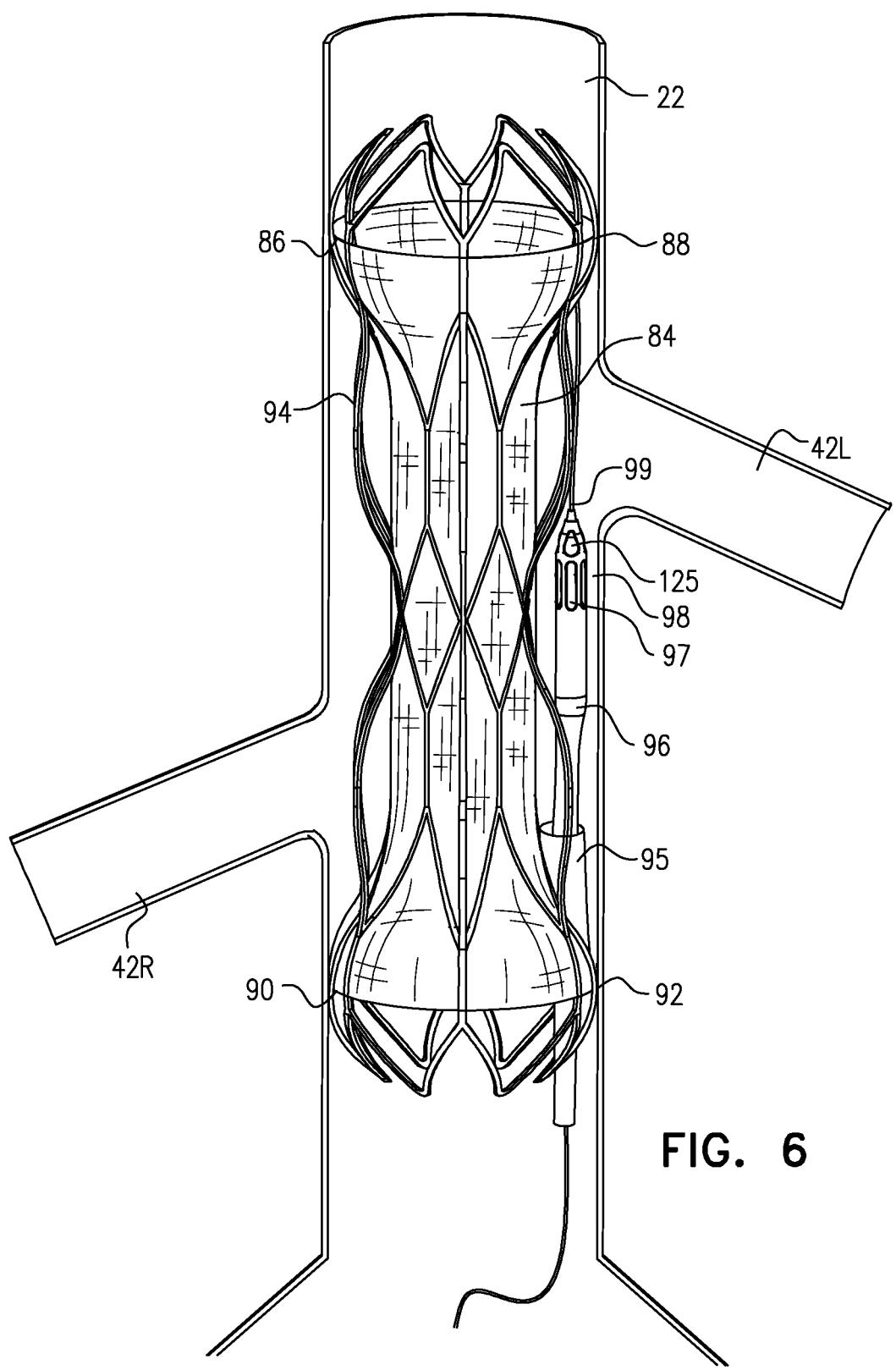
FIG. 6 is a schematic illustration of a blood-impermeable sleeve configured to occlude blood flow from a subject's vena cava to the subject's renal veins, as described in WO 14/141284 to Schwammenthal, which is incorporated herein by reference, and in accordance with some applications of the present invention.

Reference is now made to FIG. 6, which is a schematic illustration of a blood-impermeable sleeve 84 configured to occlude blood flow from a subject's vena cava to the subject's renal veins, as described in WO 14/141284 to Schwammenthal, which is incorporated herein by reference. Typically, the sleeve is placed within the vena cava such that a downstream end 86 of the sleeve is coupled to the wall of the vena cava at a first location 88 that is downstream of all renal veins 42 of the subject (e.g., left and right renal vein in a typical subject that has two renal veins), and such that an upstream end 90 of the sleeve is coupled to a wall of the vena cava at a second location 92 that is upstream of all renal veins of the subject. Thus, the sleeve isolates the blood in the renal veins into a compartment that is separated from blood flow through the center of the vena cava. Typically, a rigid structure, e.g., a stent 94 as shown, is configured to couple the upstream and downstream ends of the sleeve to the vena cava.

A pump 96 is configured to pump blood through inlet holes 97, from a location that is exterior to sleeve 98 (i.e., from the isolated compartment) to a location that is in fluid communication with the interior of the sleeve (e.g., a location within the vena cava upstream or downstream of the sleeve). Thus, the pump pumps blood out of the subject's renal veins and into the subject's vena cava. The sleeve prevents backflow of blood from the vena cava into the renal veins.

For some applications, sleeve 84 and stent 94 are inserted into the subject's vena cava, while a guidewire 99 is disposed inside a pump-accommodating sleeve 95. Subsequent to anchoring sleeve 84 and stent 94 to the vena cava, pump 96 is inserted through the pump-accommodating sleeve, by advancing the pump over the guidewire.

Sleeve 84 and pump 96 are generally as described with reference to FIGS. 10A-D of WO 14/141284 to Schwammenthal, which is incorporated herein by reference.

It is noted that the effect of inserting sleeve 84 into the vena cava and activating pump 96 in the described manner is that a low-pressure region is generated within the subject's vena cava, adjacent to junctions of the vena cava with the subject's renal veins, blood pressure within the low-pressure region being lower than central venous pressure of the subject. Similarly, by using blood-pump catheter 20 as described with reference to FIGS. 1A-5B, a low-pressure region is generated within the subject's vena cava, adjacent to junctions of the vena cava with the subject's renal veins, blood pressure within the low-pressure region being lower than central venous pressure of the subject. The effect of generating the low-pressure region within the vena cava is typically that blood flow from the renal veins to the vena cava is increased, thereby reducing renal venous pressure, and increasing renal perfusion.

Figure 7A:
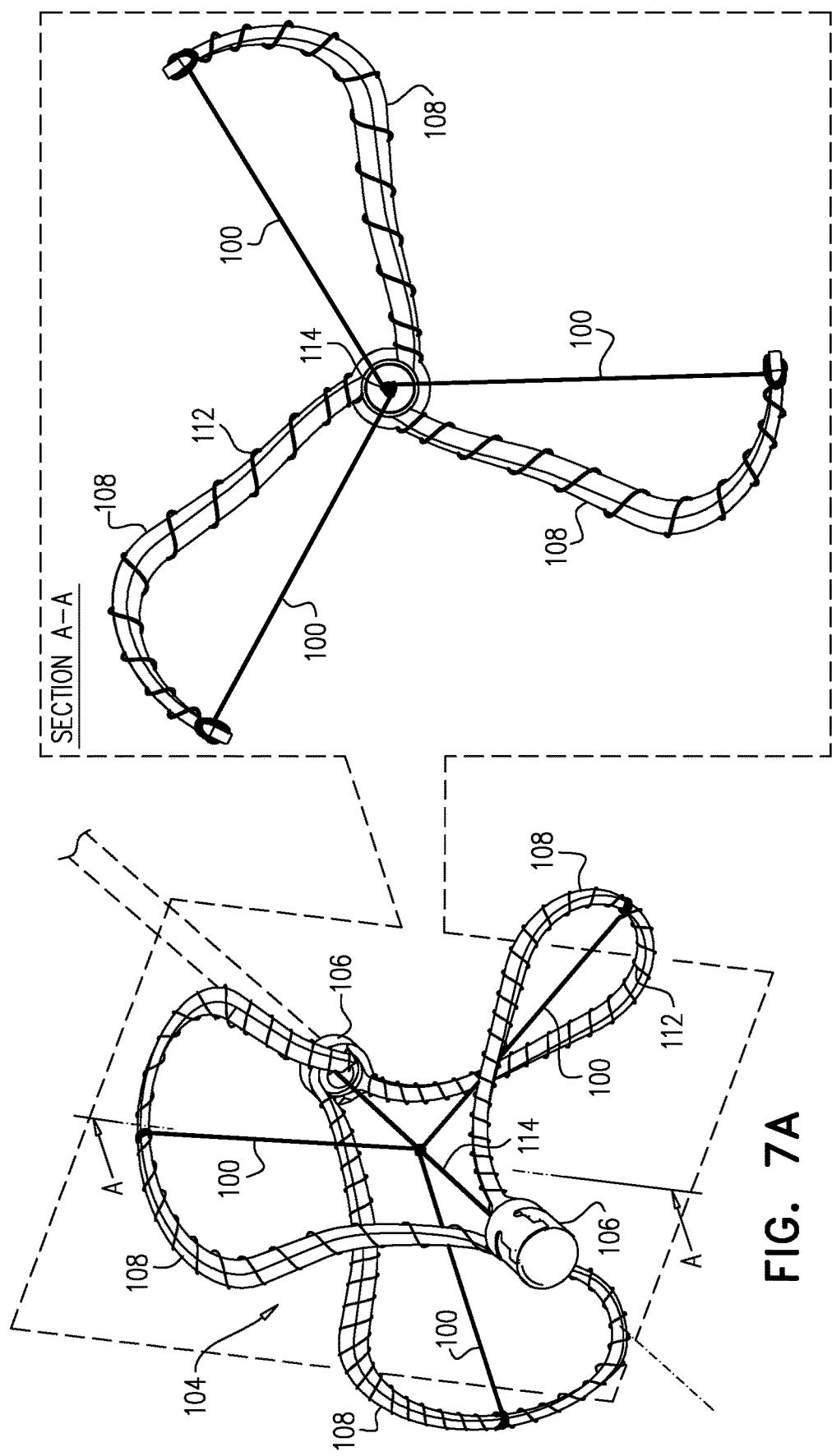
FIGS. 7A, 7B, and 7C are schematic illustrations of respective stages of a method of manufacture of an impeller that includes reinforcement elements for reinforcing blades of the impeller, in accordance with some applications of the present invention.
Figure 7B:
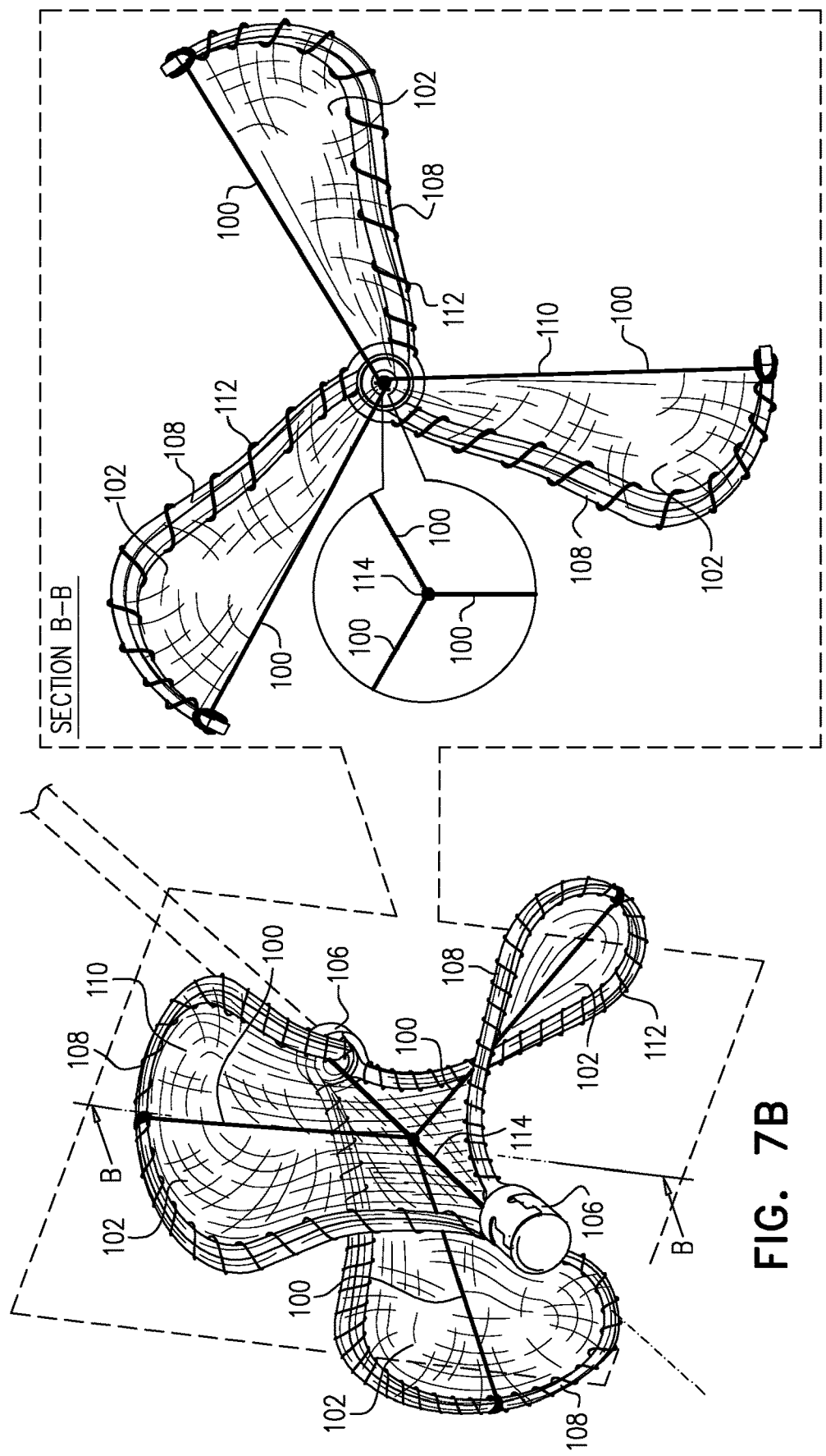
Figure 7C:
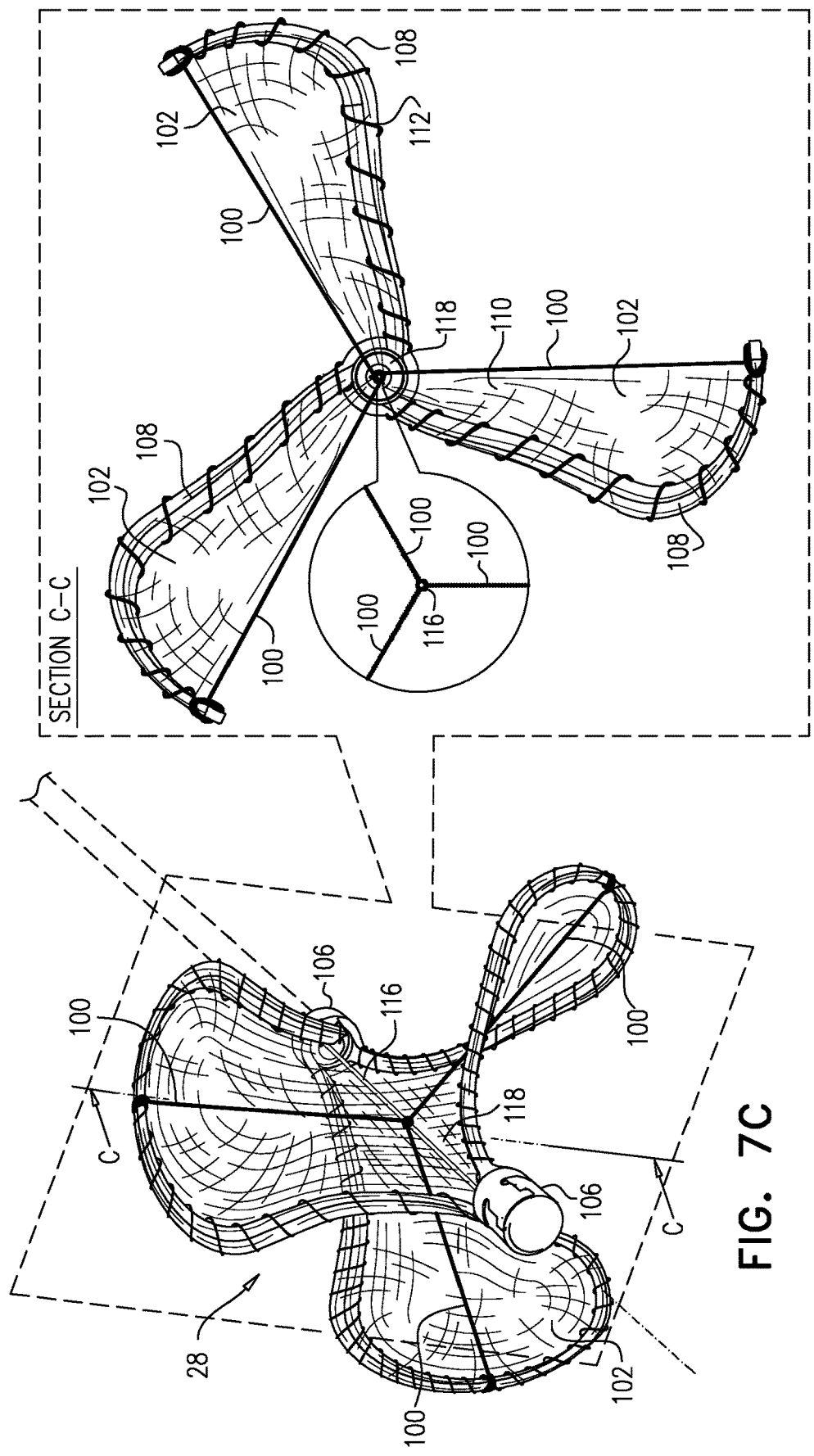

Reference is now made to FIGS. 7A-C, which are schematic illustrations of respective stages of a method of manufacture of impeller 28 (which is typically a bladed rotor), the impeller including reinforcement elements 100 for reinforcing blades 102 of the impeller, in accordance with some applications of the present invention. It is noted that FIGS. 7A-C show a three-bladed impeller. However, the techniques described with reference to FIGS. 7A-C may be practiced with an impeller having a different number of blades (e.g., one blade, two blades, or more than three blades), mutatis mutandis, in accordance with some applications of the present invention.

In accordance with the techniques described in WO 14/141284 to Schwammenthal, which is incorporated herein by reference, for some applications, a tube (e.g., a nitinol, a stainless steel, or a plastic tube) is cut (e.g., laser cut), such that the cut tube defines a structure 104 having first and second end portions, e.g., rings 106, at ends of the structure, the rings being connected to each other by a plurality of elongate elements. The tube is then axially compressed, such that the elongate elements form respective helical elongate elements 108, and typically, the structure is shape-set in the axially compressed state of the structure. Structure 104 forms the frame of impeller 28.

For some applications, as shown in FIGS. 7A-C, the impeller defines three blades 102, in accordance with some applications of the present invention. For such applications, the tube is cut define three elongate elements. Alternatively or additionally, the impeller defines two blades (e.g., as described in WO 14/141284 to Schwammenthal, which is incorporated herein by reference), or a different number of blades.

As described hereinabove, typically, in the axially compressed state of structure 104, each of the elongate elements of structure 104 forms a helical elongate element 108. Each of the helical elongate elements originates from a first one of the end portions (e.g., rings 106) and terminates at the second one of the end portions (e.g., rings 106). The pitches of each of the helical elongate elements are typically within 20 percent of one another, the helical elongate elements typically having the same pitch as one another. For some applications, the pitch of the helical elongate elements varies along the length of the helical elongate elements. The radii of each of the helical elongate elements are typically within 20 percent of one another, and, typically, the helical elongate elements have the same radius as one another. For some applications, the helices defined by the three elongate elements are not symmetrical with respect to one another. The longitudinal axis of each one of the helical elongate elements is typically parallel to the longitudinal axis of the other one of the helical elongate elements, and is typically parallel to the longitudinal axis of the impeller. For some applications, each of the elongate elements defines more than one eighth of a winding of a helix, and/or less than half a winding of a helix, e.g., between one eighth of a winding and half a winding of a helix.

It is noted that, although each of the elongate elements is described as being helical, for some applications, the elongate elements do not define precise mathematical helices, but each of the elongate elements defines a generally helical shape in that the elongate element spirals radially outwardly from a first one of end portions (e.g., rings), while extending axially away from the first one of the end portions, and then spirals radially inwardly toward the second one of the end portions, while extending axially toward the second one of the end portions.

As described in WO 14/141284 to Schwammenthal, which is incorporated herein by reference, subsequent to axially compressing structure 104, a material 110 (e.g., a flexible polymeric material, such as silicone, polyurethane, and/or polyester) is coupled to at least a portion of structure 104, e.g., to helical elongate elements 108 of structure 104. Typically, material 110 is coupled to the portion of structure 104 by structure 104 being dipped into material 110, while material 110 is in a liquid state thereof. For example, structure 104 may be dipped into liquid silicone, a silicone-based elastomer, and/or a different elastomer. Subsequently, the material is dried (e.g., by a curing and/or a polymerization process), such that a film of the material forms that is supported by the helical elongate elements 108 of structure 104.

For some applications, during the drying of material 110, structure 104 is rotated about its longitudinal axis, such as to facilitate the formation of a film of material 110 having a uniform thickness. For some applications, material 110 is coupled to structure 104 in a different manner to the above-described manner, e.g., via suturing and/or electrospinning a flexible polymeric material (such as silicone, polyurethane, and/or polyester) to the helical elongate elements of structure 104. The helical elongate elements 108 with the material coupled thereto define the impeller blades. For some applications, the material is dried (e.g., by curing, and/or polymerization) onto the helical elongate elements such that the helical elongate elements with the material coupled thereto forms a three-bladed impeller, as shown in FIG. 7B-C.

For some applications, sutures 112 are tied around a portion of the frame of the impeller, in accordance with techniques described in WO 14/141284 to Schwammenthal, which is incorporated herein by reference. For some applications, in order to facilitate the formation of a film of material 110 on structure 104, and/or in order to facilitate coupling of material 110 to helical elongate elements 108, sutures 112 are tied around a portion of structure 104. For example, the sutures may be tied around helical elongate elements 108 of structure 104, as shown in FIG. 7A, which shows sutures 112 tied around helical elongate elements 108 before material 110 has been coupled to structure 104.

As is generally described in WO 14/141284 to Schwammenthal, which is incorporated herein by reference, for some applications, sutures 112 increase the surface area with which material 110 comes into contact, while material 110 is in its liquid state. Alternatively or additionally, the surface of the sutures is more rough and/or porous than that of elongate elements 108 (which are typically made of nitinol). Therefore, material 110 becomes coupled to the sutures with a greater coupling strength than that of the coupling between material 110 and elongate elements 108. For some applications, the sutures act as mediators between a material from which the elongate elements are made, which typically has a relatively high stiffness (and is typically nitinol), and material 110, which is typically an elastomer having a relatively low stiffness. The sutures thereby enhance the strength of the coupling between material 110 and helical elongate elements 108, when the material dries. For some applications, by enhancing the strength of the coupling between material 110 and helical elongate elements 108, the sutures prevent gaps from forming between the material and helical elongate elements 108, during and/or after the drying of material 110. In this manner, the sutures facilitate the formation of a film of material 110 between the helical elongate elements.

For some applications, before material 110 is coupled to structure 104 (i.e., the frame of the impeller), reinforcement elements 100 are coupled to the structure. Typically, a respective reinforcement element is coupled to each of helical elongate elements 108, such that there is a respective reinforcement element corresponding to each one of the impeller blades. Further typically, each of the reinforcement elements extends from a helical elongate element toward the longitudinal axis of the structure 104. For some applications, each of the reinforcement elements extends from a longitudinal center of a helical elongate element toward the longitudinal axis of the structure 104. Typically, the reinforcement elements are strings (e.g., strings made of polyester, polyamide, silicone, nylon, synthetic or biological polymers) and/or wires (e.g., wires made of nitinol, stainless steel, cobalt chrome or other metal alloys).

For some applications, an axial element 114 is placed along the longitudinal axis of structure 104, and the reinforcement elements are coupled to the axial element, such that each of the reinforcement elements extends from a helical elongate element to the axial element. For some applications, the axial element is a string (e.g., a string made of polytetrafluoroethylene, extruded polytetrafluoroethylene, and/or nylon), and/or a wire (e.g., a wire made of nitinol, stainless steel, cobalt chrome or other metal alloys).

With reference to FIG. 7B, subsequent to coupling reinforcement elements 100 to structure 104, material 110 is coupled to the structure, typically using techniques as described hereinabove, e.g., by structure 104 being dipped into material 110, while material 110 is in a liquid state thereof. For some applications, including a reinforcement element in the space between a helical elongate element and the longitudinal axis of structure 104, facilitates the formation of a film of material 110 that encompasses the entire aforementioned space, and that does not include any holes. Typically, the reinforcement elements reinforce central portions of the impeller blades. For example, the reinforcement element may reinforce the film along the longitudinal center of the film, where, in the absence of the reinforcement element, the film may be thin and may be given to allow the formation of a hole through the film. The reinforcement element provides an additional surface to which the film of the material can become attached. For some applications, the reinforcement elements are used to facilitate the formation of a film of material 110 that encompasses the space between a helical elongate element and the longitudinal axis of structure 104 for an impeller that is suitable for placing in the vena cava, e.g., an impeller having a span of more than 14 mm (e.g., more than 16 mm). As shown in FIG. 7B, typically, each of the blades of the impeller includes a respective reinforcement element, in accordance with the techniques described hereinabove.

With reference to FIG. 7C, for some applications, subsequent to the coupling of material 110 to structure 104, axial element 114 is removed from the longitudinal axis of structure 104. As described hereinabove, for some applications, the axial element is a string (e.g., a string made of polytetrafluoroethylene, extruded polytetrafluoroethylene, and/or nylon), and/or a wire (e.g., a wire made of nitinol, stainless steel, cobalt chrome or other metal alloys). For such applications, the string and/or the wire is typically removed from the longitudinal axis of structure 104, such that reinforcement elements 100 remain in place. Typically, material 110 defines a hollow central lumen 116 along the longitudinal axis of structure 104, subsequent to the removal of the axial element from the longitudinal axis. Further typically, the film of material 110 defines a thickened portion 118 that surrounds the hollow central lumen and that is thickened relative to the thickness of the material at other portions of the film. For some applications, the impeller is strengthened by virtue of the thickened portion of the film that surrounds the hollow central lumen, relative to an otherwise similarly shaped impeller that does not define the thickened portion of film.

For some applications of the present invention, axial element 114 is placed inside structure 104 before material 110 is coupled to the structure, even in the absence of reinforcing elements inside the structure. In this manner, the film of material forms a thickened portion 118 that surrounds the hollow central lumen and that is thickened relative to the thickness of the material at other portions of the film, in accordance with the techniques described hereinabove.

As is generally described in WO 14/141284 to Schwammenthal, which is incorporated herein by reference, for some applications, the three-bladed impeller shown in FIGS. 7A-C does not include an axial support member (such as a shaft) between the proximal and distal ends of the helical elongate elements and along the axis of the impeller, for providing support to material 110. More generally, for some applications, the impeller does not include a support member (such as a shaft) for providing support to material 110 in addition to the helical elongate elements, between the proximal and distal ends of the helical elongate elements. Furthermore, rotational motion is imparted from the proximal end portion (e.g., proximal ring 106) of the impeller to the distal end portion (e.g., distal ring 106) of the impeller via the helical elongate elements 108 of the impeller (e.g., substantially solely via the helical elongate elements), and not via an axial support member (such as a shaft).

For some applications, material 110 of the impeller itself is molded such as to facilitate the insertion of an axial support member therethrough. For example, an elastomer (such as silicone or a silicone-based elastomer) may be used as material 110, and the elastomer may be molded to form a hollow central lumen therethrough. In accordance with the techniques described hereinabove, for some applications, axial element 114 is placed inside structure 104 before material 110 is coupled to the structure. In this manner, the film of material is shaped to define hollow central lumen 116. For some applications, an axial support member is coupled to the impeller by being passed through the hollow central lumen defined by the elastomer. Alternatively or additionally, an impeller that includes an axial support member is provided using the techniques described hereinbelow with reference to FIGS. 8A-10C.

Figure 8A:
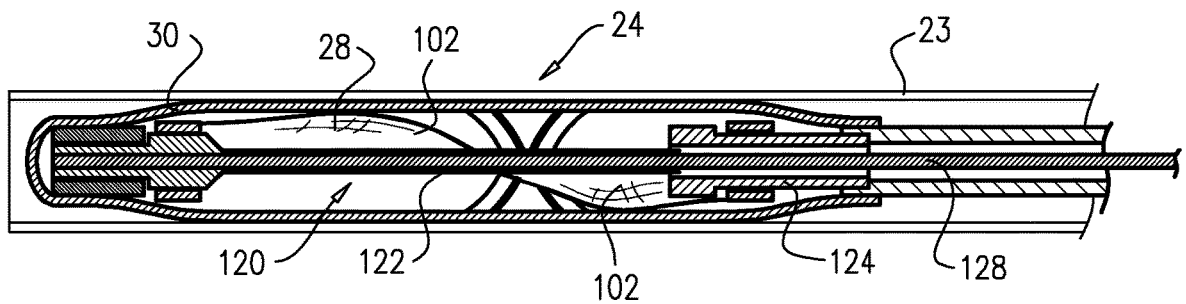
FIGS. 8A, 8B, and 8C are schematic illustrations of a blood-pump catheter that includes an impeller that includes a telescopic axial shaft, in accordance with some applications of the present invention.
Figure 8B:
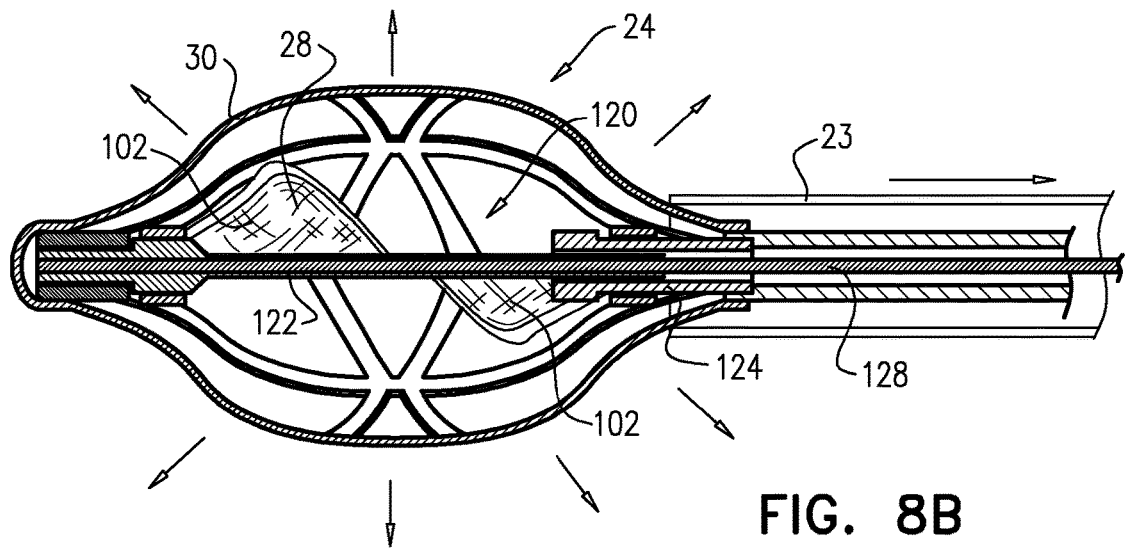
Figure 8C:
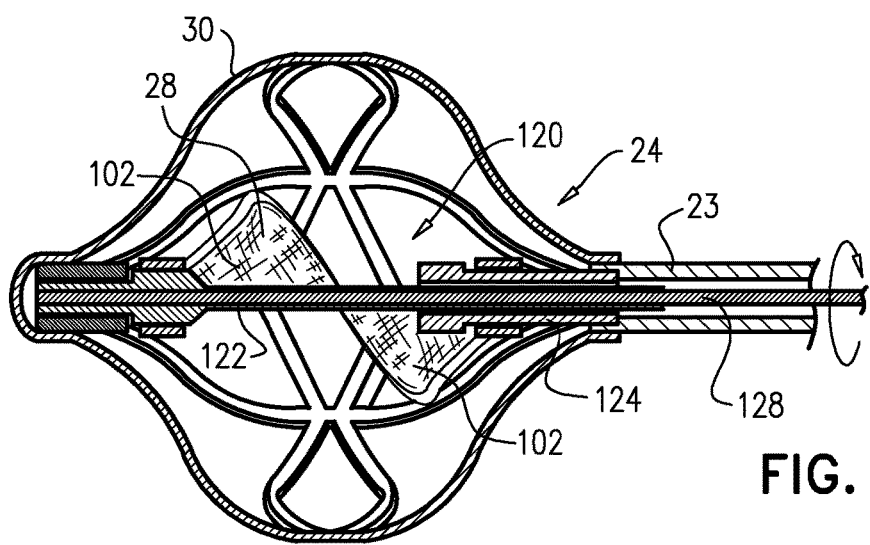

Reference is now made to FIGS. 8A-C, which are schematic illustrations of blood-pump catheter 20, the blood-pump catheter including impeller 28, the impeller including an axially elongatable telescopic axial shaft 120, in accordance with some applications of the present invention. It is noted that FIGS. 8A-C show a two-bladed impeller. However, the techniques described with reference to FIGS. 8A-C may be practiced with an impeller having a different number of blades (e.g., one blade, three blades, or more than three blades), mutatis mutandis, in accordance with some applications of the present invention.

As is generally described in WO 14/141284 to Schwammenthal, which is incorporated herein by reference, typically, during insertion of cage 30 and impeller 28 into the subject's vasculature, the cage and the impeller are crimped by axially elongating the cage and the impeller, such that the cage and the impeller become radially compressed. The cage and the impeller are inserted into the vasculature, while the cage and the impeller are maintained in radially-compressed configurations by an insertion device, e.g., catheter 23. The cage and the impeller are released from the distal end of the insertion device into the renal vein, typically by retracting the insertion device. In response to being released from the distal end of the insertion device, the cage and the impeller automatically radially expand, and axially contract.

As shown in the transition from FIG. 8A to FIG. 8B and then to FIG. 8C, for some applications, as the cage expands radially, the distal end of the cage moves closer to the proximal end of the cage. (It is noted that distal end of the cage may move closer to the proximal end of the cage by either or both ends of the cage moving. That is, the distal end of the cage may move proximally, and/or the proximal end of the cage may move distally.) The distal end of the cage engages an inner tubular member 122 of telescopic shaft 120, such that the movement of the distal end of the cage closer to the proximal end of the cage causes the inner tubular member of the telescopic shaft to slide proximally with respect to an outer tubular member 124 of the telescopic shaft. In this manner the telescopic shaft contracts in the axial direction causing impeller blades 102 to radially expand. It is noted that, typically, the impeller is shape-set such as to radially expand in the absence of any radial constraining force acting upon the impeller. Typically, a rotating shaft member 128 is disposed inside both the inner and outer tubular members of the telescopic shaft and is configured to impart rotational motion to the impeller blades.

Typically, cage 30 is configured to hold open the inner wall of the vena cava and to separate the inner wall of the vena cava from the impeller, such that the vena cava does not become injured by the impeller, in accordance with the general techniques described in WO 14/141284 to Schwammenthal, which is incorporated herein by reference. For some applications, in response to the cage becoming radially contracted and axially elongated (e.g., in response to the renal vein exerting radial pressure on the cage), the distal end of the cage moves away from the proximal end of the cage. The distal end of the cage engages inner tubular member 122 of telescopic shaft 120, so as to cause the inner tubular member of the telescopic shaft to slide distally with respect to an outer tubular member 124 of the telescopic shaft. In this manner the telescopic shaft elongates in the axial direction causing impeller blades 102 to radially contract.

The cage is typically engaged with respect to the telescopic shaft such that, even at a circumferential location at which a separation between the impeller and the inner surface of the cage is smallest, a separation between the impeller and the inner surface of the cage is maintained (i.e., the impeller and the inner surface of the cage are still separated from each other), even if the cage radially contracts. A fortiori, even at the circumferential location at which a separation between the impeller and the outer surface of the cage is smallest, the cage is engaged with respect to the telescopic shaft such that the separation between the impeller and the outer surface of the cage is maintained (i.e., the impeller and the outer surface of the cage are still separated from each other), even if the cage radially contracts. Since the inner wall of the renal vein is supported by the outer surface of the cage, the separation between the impeller and the outer surface of the cage is typically also the separation between the impeller and the inner wall of the renal vein at the location at which the inner wall of the renal vein is closest to the impeller. Thus, the cage is engaged with respect to the telescopic shaft such that a separation between the impeller and the inner wall of the renal vein is maintained, even at the location at which the inner wall of the renal vein is closest to the impeller, and even when the renal vein exerts pressure on the cage such that the cage radially contracts.

Figure 9A:
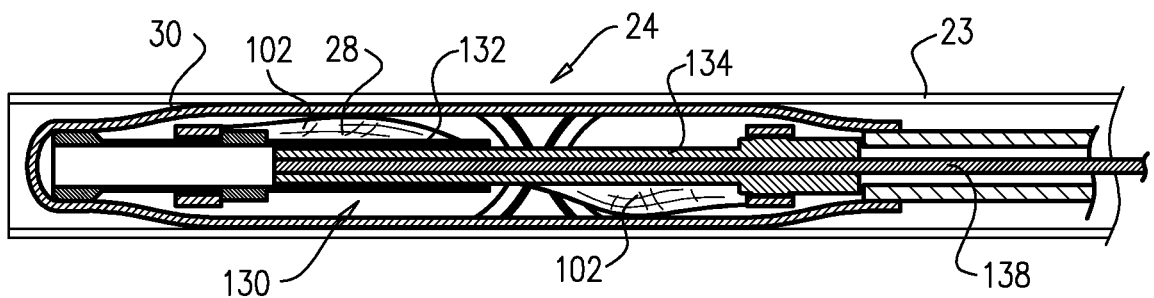
FIGS. 9A, 9B, and 9C are schematic illustrations of a blood-pump catheter that includes an impeller that includes a telescopic axial shaft, in accordance with some alternative applications of the present invention.
Figure 9B:
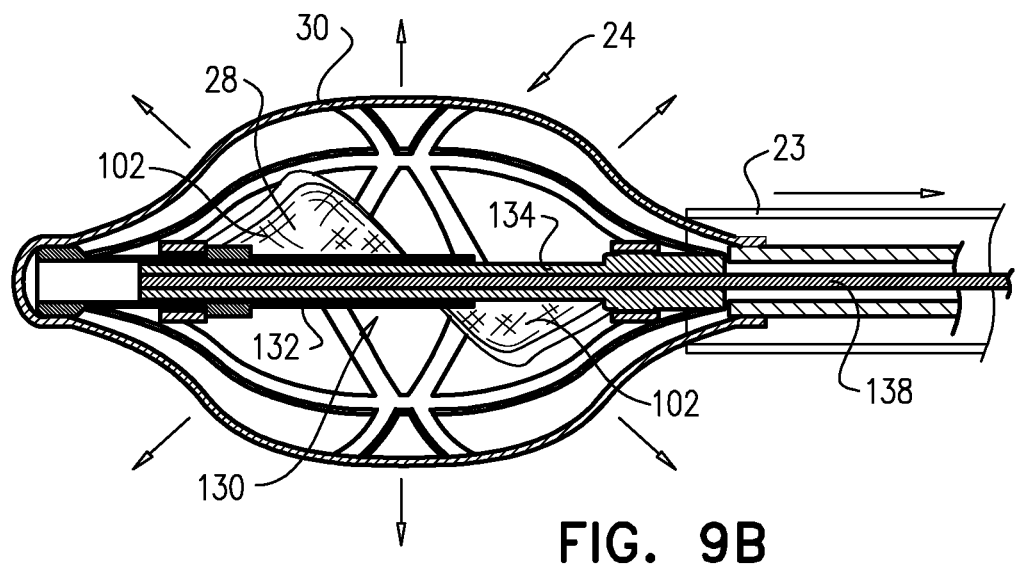
Figure 9C:
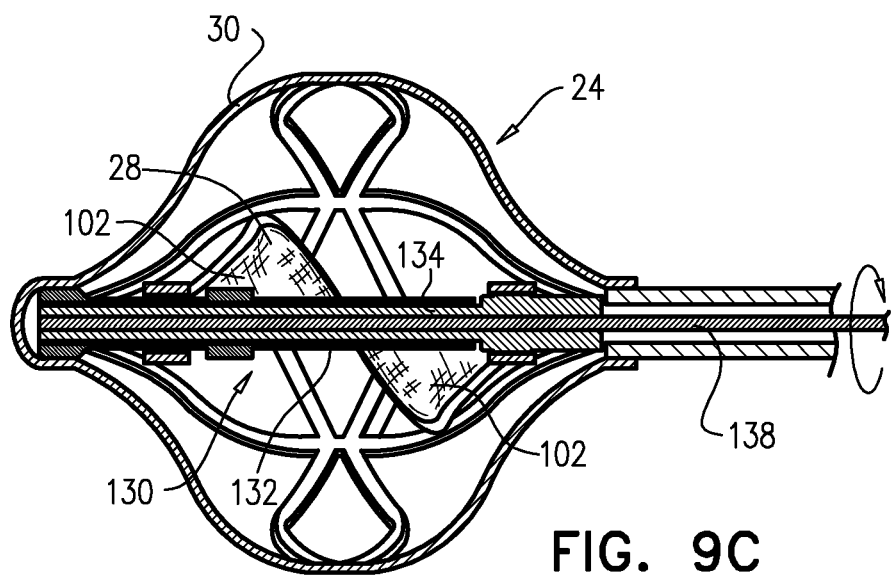

Reference is now made to FIGS. 9A-C, which are schematic illustrations of blood-pump catheter 20, the blood-pump catheter including impeller 28, the impeller including axially elongatable telescopic axial shaft 130, in accordance with some applications of the present invention. It is noted that FIGS. 9A-C show a two-bladed impeller. However, the techniques described with reference to FIGS. 8A-C may be practiced with an impeller having a different number of blades (e.g., one blade, three blades, or more than three blades), mutatis mutandis, in accordance with some applications of the present invention.

As is generally described in WO 14/141284 to Schwammenthal, which is incorporated herein by reference, typically, during insertion of cage 30 and impeller 28 into the subject's vasculature, the cage and the impeller are crimped by axially elongating the cage and the impeller, such that the cage and the impeller become radially compressed. The cage and the impeller are inserted into the vasculature, while the cage and the impeller are maintained in radially compressed configurations by an insertion device, e.g., catheter 23. The cage and the impeller are released from the distal end of the insertion device into the renal vein, typically by retracting the insertion device. In response to being released from the distal end of the insertion device, the cage and the impeller automatically radially expand, and axially contract.

As shown in the transition from FIG. 9A to FIG. 9B and then to FIG. 9C, for some applications, as the cage expands radially, the distal end of the cage moves closer to the proximal end of the cage. (It is noted that distal end of the cage may move closer to the proximal end of the cage by either or both ends of the cage moving. That is, the distal end of the cage may move proximally, and/or the proximal end of the cage may move distally.) The distal end of the cage engages an outer tubular member 132 of telescopic shaft 130, such that the movement of the distal end of the cage closer to the proximal end of the cage causes the outer tubular member of the telescopic shaft to slide proximally with respect to an inner tubular member 134 of the telescopic shaft. In this manner the telescopic shaft contracts in the axial direction causing impeller blades 102 to radially expand. It is noted that, typically, the impeller is shape-set such as to radially expand in the absence of any radial constraining force acting upon the impeller. Typically, a rotating shaft member 138 is disposed inside both the inner and outer tubular members of the telescopic shaft and is configured to impart rotational motion to the impeller blades.

Typically, cage 30 is configured to hold open the inner wall of the vena cava and to separate the inner wall of the vena cava from the impeller, such that the vena cava does not become injured by the impeller, in accordance with the general techniques described in WO 14/141284 to Schwammenthal, which is incorporated herein by reference. For some applications, in response to the cage becoming radially contracted and axially elongated (e.g., in response to the renal vein exerting radial pressure on the cage), the distal end of the cage moves away from the proximal end of the cage. The distal end of the cage engages outer tubular member 132 of telescopic shaft 130, so as to cause the outer tubular member of the telescopic shaft to slide distally with respect to inner tubular member 134 of the telescopic shaft. In this manner the telescopic shaft elongates in the axial direction causing impeller blades 102 to radially contract.

The cage is engaged with respect to the telescopic shaft such that, even at a circumferential location at which a separation between the impeller and the inner surface of the cage is smallest, a separation between the impeller and the inner surface of the cage is maintained (i.e., the impeller and the inner surface of the cage are still separated from each other), even if the cage radially contracts. A fortiori, even at the circumferential location at which a separation between the impeller and the outer surface of the cage is smallest, the cage is engaged with respect to the telescopic shaft such that the separation between the impeller and the outer surface of the cage is maintained (i.e., the impeller and the outer surface of the cage are still separated from each other), even if the cage radially contracts. Since the inner wall of the renal vein is supported by the outer surface of the cage, the separation between the impeller and the outer surface of the cage is typically also the separation between the impeller and the inner wall of the renal vein at the location at which the inner wall of the renal vein is closest to the impeller. Thus, the cage is engaged with respect to the telescopic shaft such that a separation between the impeller and the inner wall of the renal vein is maintained, even at the location at which the inner wall of the renal vein is closest to the impeller, and even when the renal vein exerts pressure on the cage such that the cage radially contracts.

Figure 10A:
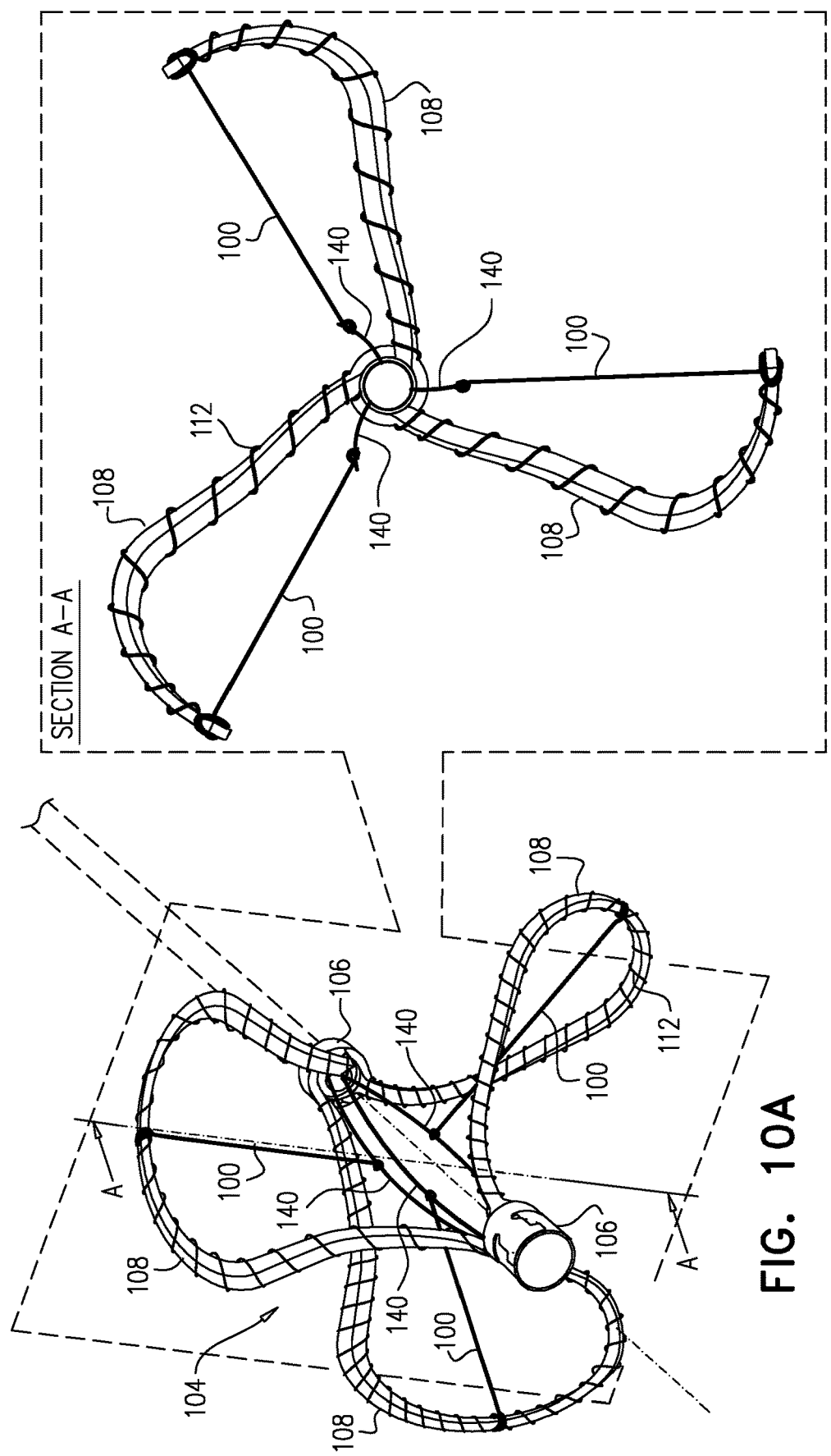
FIGS. 10A, 10B, and 10C are schematic illustrations showing respective steps of stages of a method of manufacture of an impeller that includes a telescopic axial shaft, in accordance with some applications of the present invention.
Figure 10B:
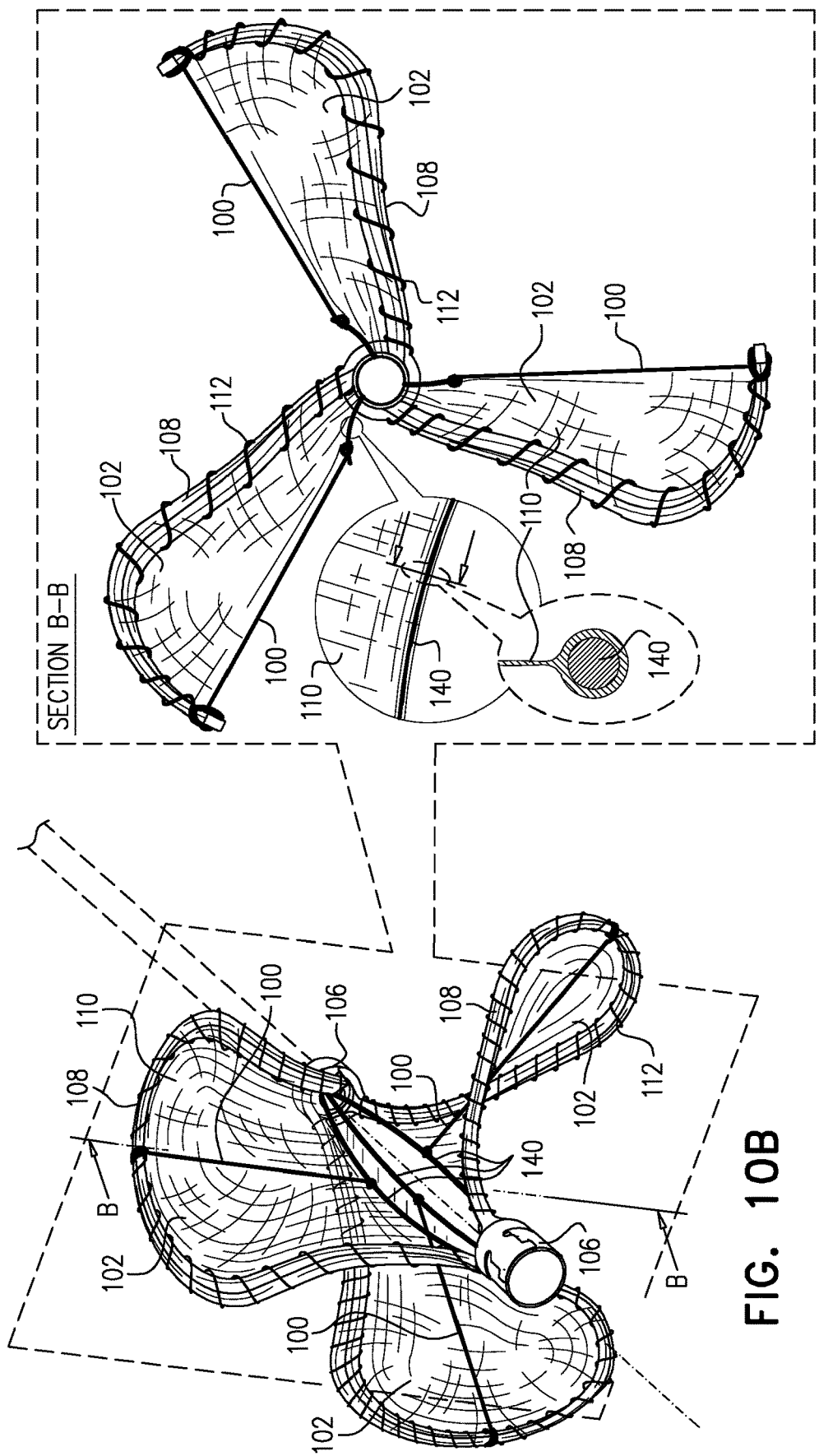
Figure 10C:
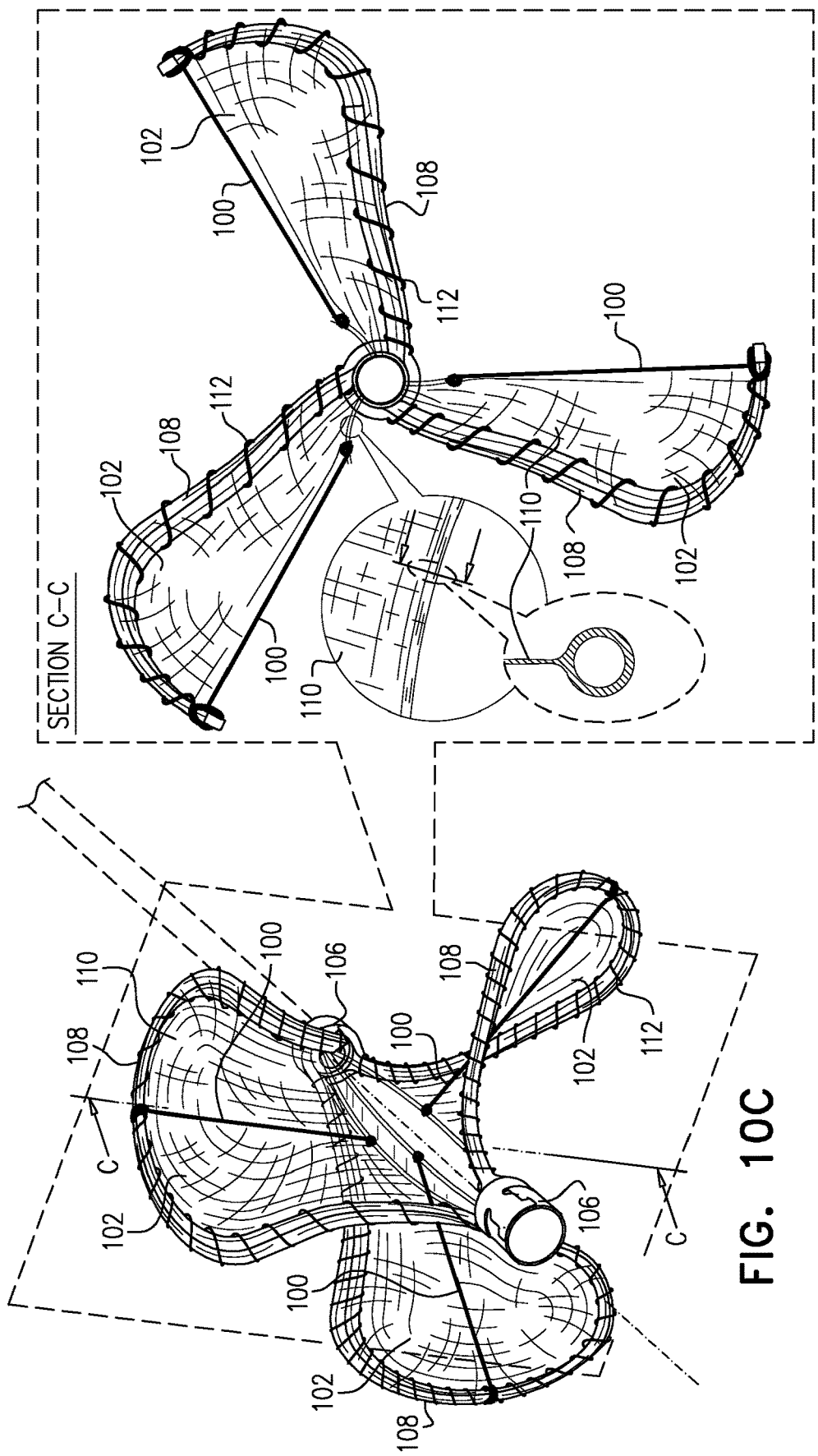

Reference is now made to FIGS. 10A-C, which are schematic illustrations showing respective steps of a method of manufacture of impeller 28, the impeller including a telescopic axial shaft (e.g., telescopic shaft 120, or telescopic shaft 130), in accordance with some applications of the present invention. It is noted that FIGS. 10A-C show a three-bladed impeller. However, the techniques described with reference to FIGS. 10A-C may be practiced with an impeller having a different number of blades (e.g., one blade, two blades, or more than three blades), mutatis mutandis, in accordance with some applications of the present invention.

For some applications, structure 104, which includes helical elongate elements (and which is generally as described hereinabove) forms the frame of the impeller 28. Material 110 (e.g., a flexible polymeric material, such as silicone, polyurethane, and/or polyester) is coupled to at least a portion of structure 104, e.g., to helical elongate elements 108 of structure 104. For some applications, sutures 112 are tied around a portion of the frame of the impeller, in accordance with techniques described in WO 14/141284, which is incorporated herein by reference. As described hereinabove, with reference to FIGS. 7A-C, for some applications, impeller 28 includes reinforcement elements 100 for reinforcing blades 102 of the impeller.

For some applications, before material 110 is coupled to structure 104 (i.e., the frame of the impeller), reinforcement elements 100 are coupled to the structure. Typically, a respective reinforcement element is coupled to each of helical elongate elements 108, such that there is a respective reinforcement element corresponding to each one of the impeller blades. For some applications, axial elements 140 are placed on the helical elongate elements in the vicinity of the longitudinal axis of structure 104, typically, such that the axial elements extend from the proximal end to the distal end of respective helical elongate elements. Respective reinforcement elements are coupled to (e.g., sutured to) respective axial elements, such that each of the reinforcement elements extends from a helical elongate element to a respective axial element. For some applications, the axial elements are strings (e.g., strings made of polytetrafluoroethylene, extruded polytetrafluoroethylene, and/or nylon), and/or a wire (e.g., a wire made of nitinol, stainless steel, cobalt chrome, or other metal alloys).

With reference to FIG. 10B, subsequent to coupling reinforcement elements 100 to structure 104, material 110 is coupled to the structure, typically using techniques as described hereinabove, e.g., by structure 104 being dipped into material 110, while material 110 is in a liquid state thereof. For some applications, including a reinforcement element in the space between a helical elongate element and an axial element 140 facilitates the formation of a film of material 110 that encompasses the entire aforementioned space, and that does not include any holes. For example, the reinforcement element may reinforce the film along the longitudinal center of the film, where, in the absence of the reinforcement element, the film may be thin and may be given to allow the formation of a hole through the film. The reinforcement element provides an additional surface to which the film of the material can become attached. For some applications, the reinforcement elements are used to facilitate the formation of a film of material 110 that encompasses the space between a helical elongate element and the axial elements for an impeller that is suitable for placing in the vena cava, e.g., an impeller having a span of more than 14 mm (e.g., more than 16 mm). As shown in FIG. 10B, typically, each of the blades of the impeller includes a respective reinforcement element, in accordance with the techniques described hereinabove. Further typically, for each of the blades of the impeller, an axial element is placed in the vicinity of the longitudinal axis of structure 104.

With reference to FIG. 10C, for some applications, subsequent to the coupling of material 110 to structure 104, axial elements 140 are removed from structure 104. As described hereinabove, for some applications, the axial elements are strings (e.g., strings made of polytetrafluoroethylene, extruded polytetrafluoroethylene, and/or nylon), and/or a wire (e.g., a wire made of nitinol, stainless steel, cobalt chrome or other metal alloys). For such applications, the strings and/or the wires are typically removed from structure 104, such that reinforcement elements 100 remain in place.

Typically, subsequent to the steps described hereinabove with reference to FIGS. 10A-C, structure 104 is mounted upon a telescopic shaft, e.g., telescopic shaft 120 (described with reference to FIGS. 8A-C), or telescopic shaft 130 (described with reference to FIGS. 9A-C).

Reference is now made to FIGS. 11A-C, which are schematic illustrations of blood-pump catheter 20 placed within a subject's vena cava 22, upstream pump 24U being disposed upon the catheter, distally to downstream pump 24D, the upstream and downstream pumps being disposed at respective separations from one another in FIGS. 11A, 11B, and 11C, in accordance with some applications of the present invention. For some applications, the upstream and downstream pumps are coupled to one another via a telescopic shaft 150, the length of which is adjustable, such that the distance between the upstream and downstream pumps is adjustable. For some applications, upon being placed inside the subject's body, the response of the subject's renal venous pressure to the pumping of pumps 24D and 24U is measured, when the pumps are disposed at respective distance from one another. Based upon the measured responses of the subject's renal venous pressure, the pumps are deployed at a given separation from one another and are operated.

For some applications, regardless of the separation between the upstream and downstream pumps 24U and 24D, the pumps are deployed in the vena cava such that the distance from the right renal vein 42R to the longitudinal center of the impeller of the upstream pump 24U is approximately equal to the distance between the left renal vein 42L and the longitudinal center of the impeller of the downstream pump 24D. Alternatively, the distance from the right renal vein 42R to the longitudinal center of the impeller of the upstream pump 24U is different from the distance between the left renal vein 42L and the longitudinal center of the impeller of the downstream pump 24D.

It is noted that blood-pump catheter 20, as shown in FIGS. 11A-C, includes only blood pressure sensor 58, in accordance with some applications of the present invention. Alternatively, blood-pump catheter 20 includes one or more additional sensors, e.g., blood pressure sensors 56 and 60, as described hereinabove.

Figure 12:
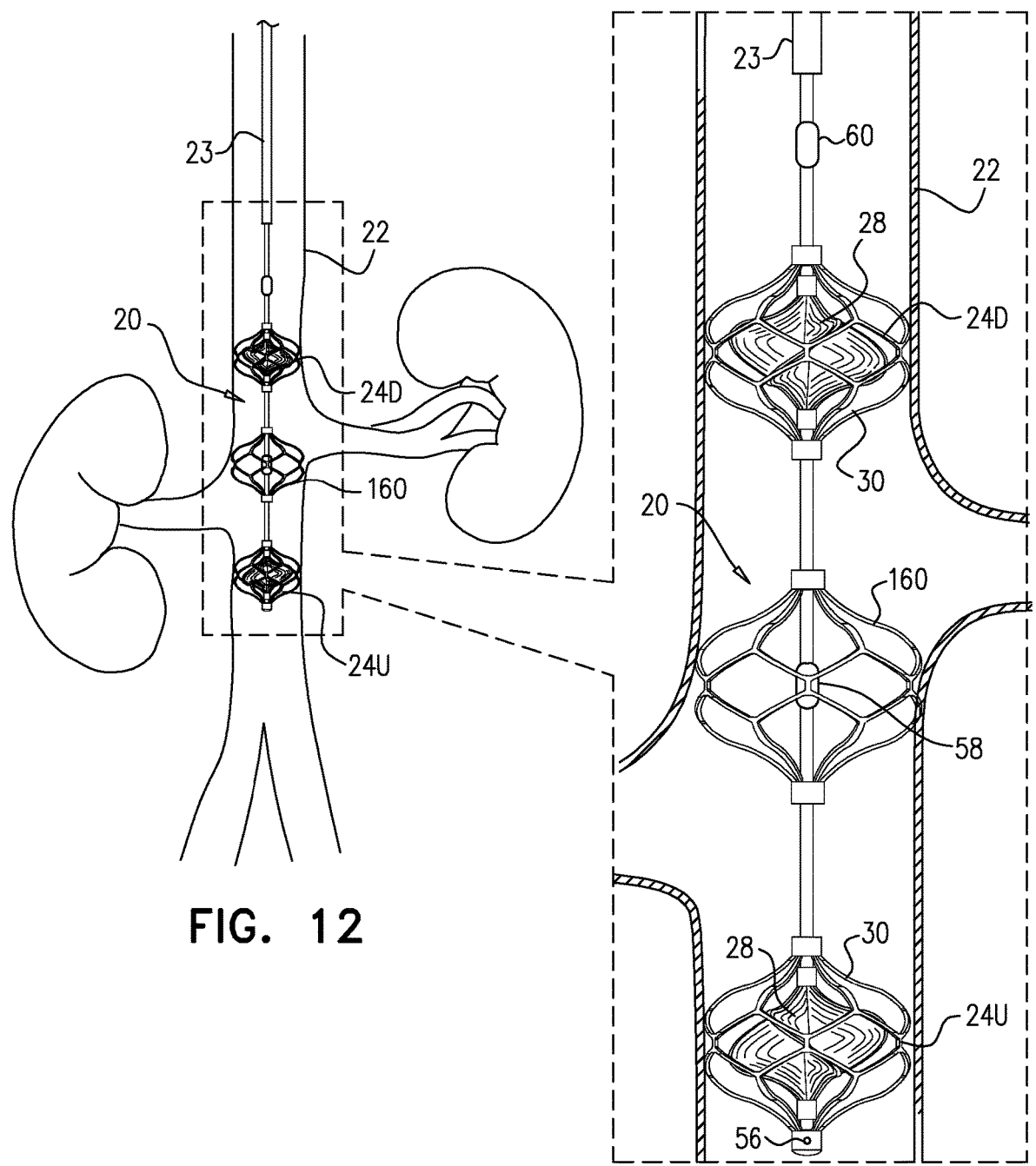
FIG. 12 is a schematic illustration of a blood-pump catheter placed within a subject's vena cava, an upstream pump being disposed upon the catheter, distally to a downstream pump, and a support stent being disposed upon the catheter between the upstream and downstream pumps, in accordance with some applications of the present invention.

Reference is now made to FIG. 12, which is a schematic illustration of blood-pump catheter 20 placed within a subject's vena cava 22, upstream pump 24U being disposed upon the catheter, distally to downstream pump 24D, and a support stent 160 being disposed upon the catheter between the upstream and downstream pumps, in accordance with some applications of the present invention. As described hereinabove, typically during operation of pumps 24U and

24D, a region of low pressure is generated within the vena cava between the two pumps. Typically, stent 160 is configured to support the walls of the vena cava at the low pressure region, such that the vena cava does not become obstructed at the low pressure region, due to the walls of the vena cava collapsing. For some applications, stent 160 has a generally similar shape to cage 30. Although FIG. 12 shows stent 160 disposed upon a blood-pump catheter, upon which the upstream pump is disposed distally to the downstream pump, for some applications, stent 160 is disposed upon a blood-pump catheter, upon which the downstream pump is disposed distally to the upstream pump, as described hereinabove.

Reference is now made to FIGS. 13A-E, which are schematic illustrations of blood-pump catheter 20 placed within a subject's vena cava 22, upstream impeller 28U being disposed upon the catheter, distally to downstream impeller 28D, the upstream and downstream impellers being disposed within a support cage 170 that supports the walls of a portion of the vena cava between the upstream and downstream impellers, in accordance with some applications of the present invention. Although some of FIGS. 13A-E shows support cage 170 disposed upon a blood-pump catheter, upon which the upstream pump is disposed distally to the downstream pump, for some applications, support cage 170 is disposed upon a blood-pump catheter, upon which the downstream pump is disposed distally to the upstream pump, as described hereinabove.

As described hereinabove, typically during operation of pumps 24U and 24D, a region of low pressure is generated within the vena cava between the two pumps. Typically, support cage 170 is configured to support the walls of the vena cava at the low pressure region, such that the vena cava does not become obstructed at the low pressure region, due to the walls of the vena cava collapsing.

Figure 13A:
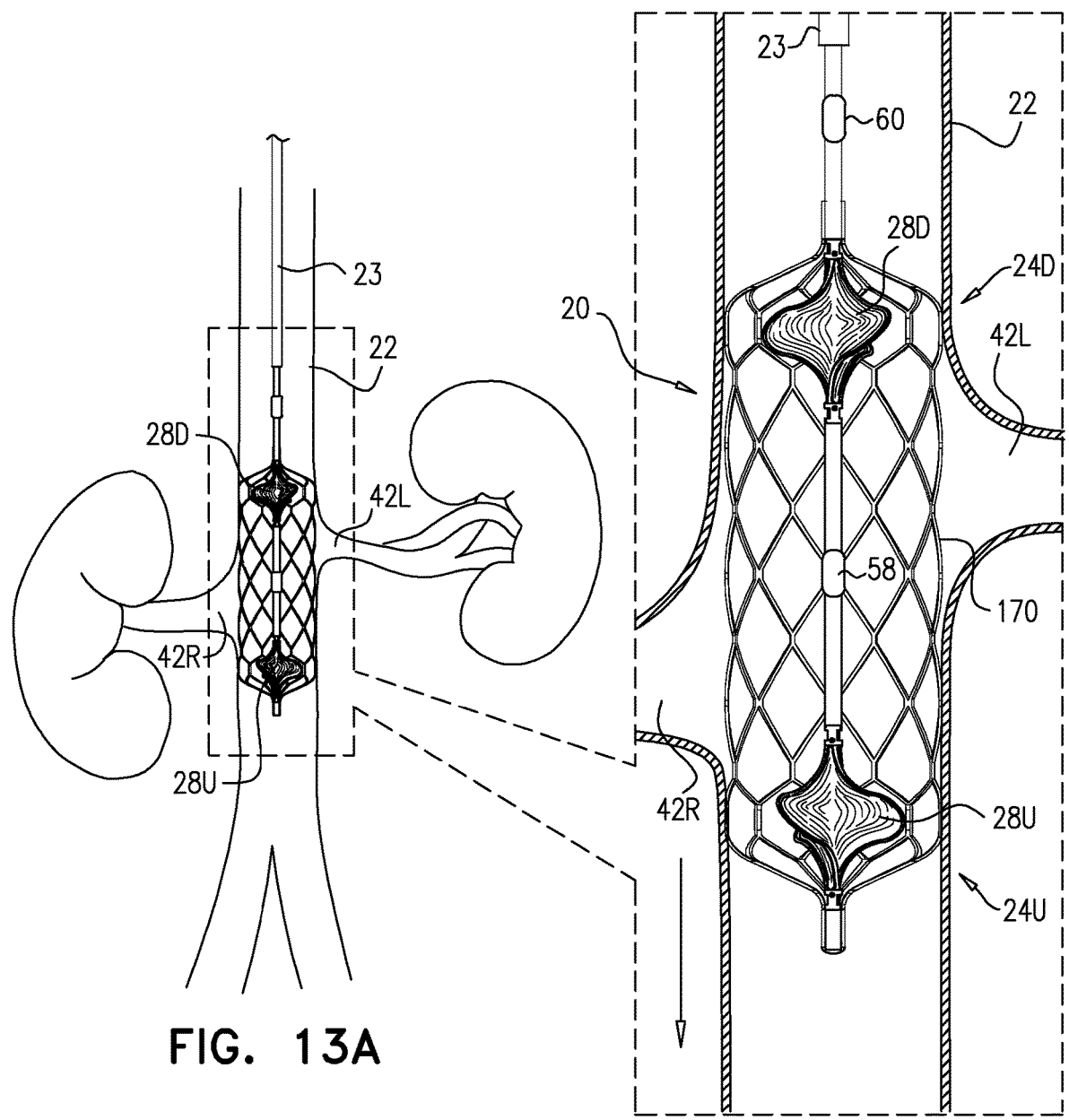
FIGS. 13A, 13B, 13C, 13D, and 13E are schematic illustrations of a blood-pump catheter for placing within a subject's vena cava, an upstream impeller being disposed upon the catheter, distally to a downstream impeller, the upstream and downstream impellers being disposed within a support cage that supports the walls of a portion of the vena cava between the upstream and downstream impellers, in accordance with some applications of the present invention.
Figure 13B:
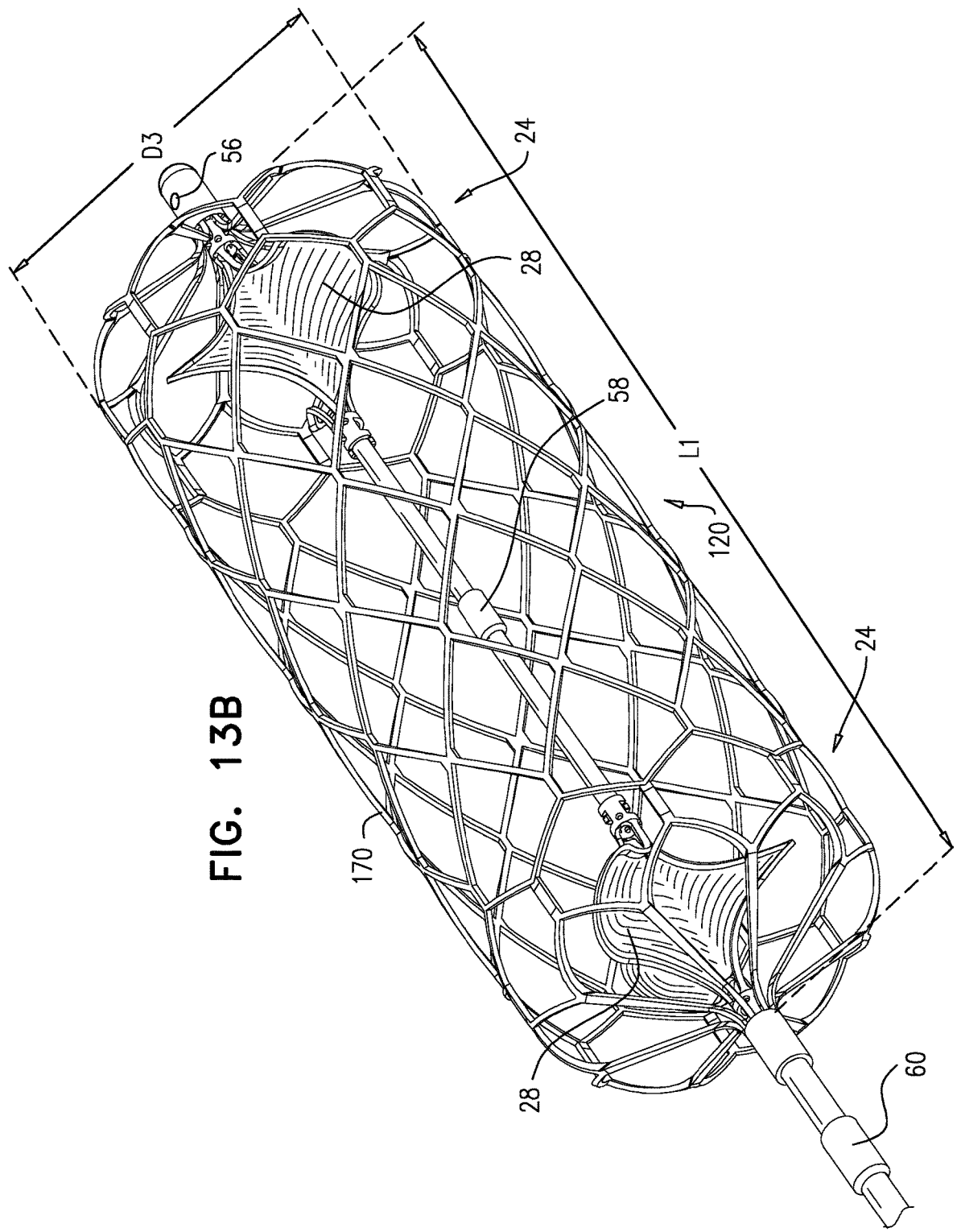
Figure 13C:
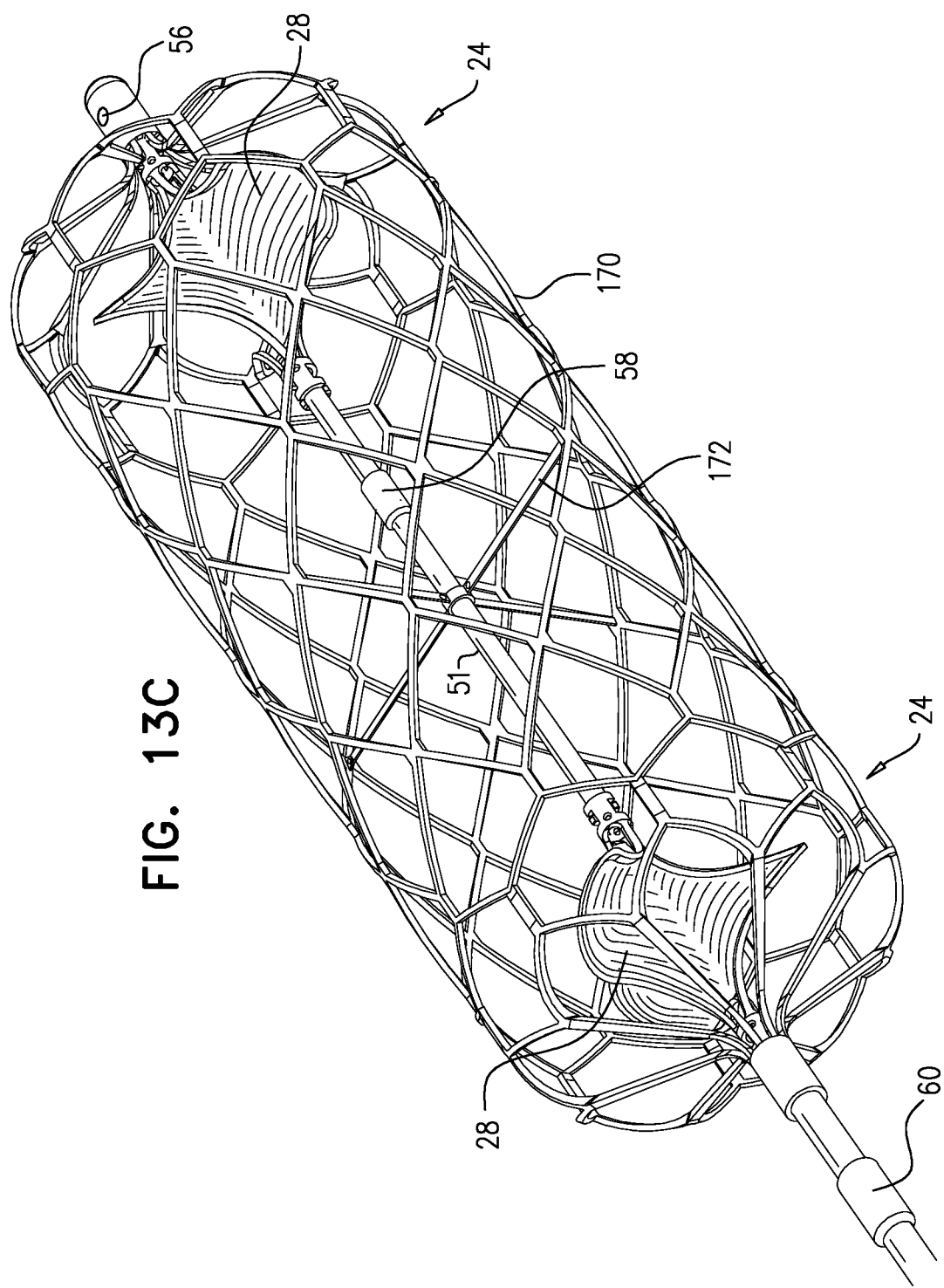

Support cage typically extends at least from the longitudinal center of the downstream impeller to the longitudinal center of the upstream impeller. For some applications, a length L1 (FIG. 13B) of the support cage, when the cage is in a non-constrained configuration thereof inside the vena cava, is more than 3 cm (e.g., more than 6 cm), and/or less than 18 cm (e.g., less than 14 cm), e.g., 3-18 cm, or 6-14 cm. Further typically, a diameter D3 (FIG. 13B) of support cage 170, when the cage is in a non-constrained configuration thereof inside the vena cava, is more than 14 mm (e.g., more than 16 mm), and/or less than 35 mm (e.g., less than 25 mm), e.g., 14-35 mm, or 16-25 mm For some applications, as shown in FIGS. 13A-C, the impellers are placed inside support cage 170, in the absence of individual cages that are disposed around the respective impellers. For such applications, the support cage is typically configured to (a) support the walls of the vena cava at the low pressure region, as described hereinabove, and (b) to maintain a separation between the impellers and the inner wall of the vena cava, in a generally similar manner to that described hereinabove with respect to cage 30.

FIG. 13A shows a blood-pump catheter as described, placed inside the subject's vena cava 22. FIG. 13B shows a three-dimensional view of impellers and support cage 170 as described, in the absence of the subject's anatomy. FIG. 13C shows a three-dimensional view of impellers and support cage 170, in the absence of the subject's anatomy, and with the support cage including support elements 172, in accordance with some applications of the present invention. As described hereinabove, for some applications, an axial shaft 51 is disposed between the proximal and distal impellers and is configured to impart rotational motion from the proximal impeller to the distal impeller. For some applications, support elements 172 extend from the support cage, and are coupled to axial shaft 51, such as to maintain the disposition of shaft 51 along the longitudinal axis of the support cage. In this manner, the disposition of the axial shaft is typically maintained along the longitudinal axis of the vena cava. Further typically, the support elements maintain the longitudinal axes of the proximal and distal impellers in alignment with one another, and in alignment with the longitudinal axis of the vena cava.

Figure 13D:
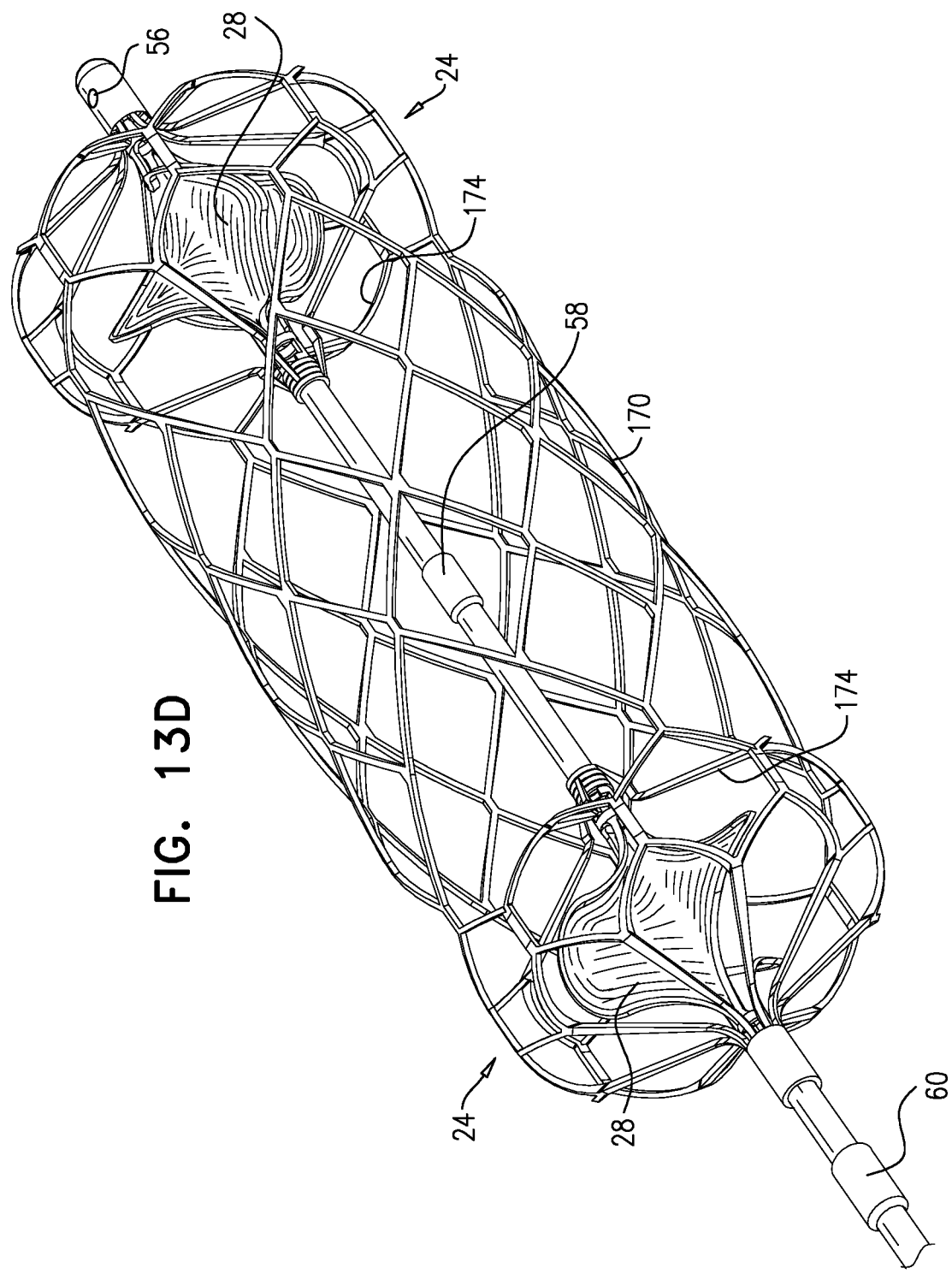
Figure 13E:
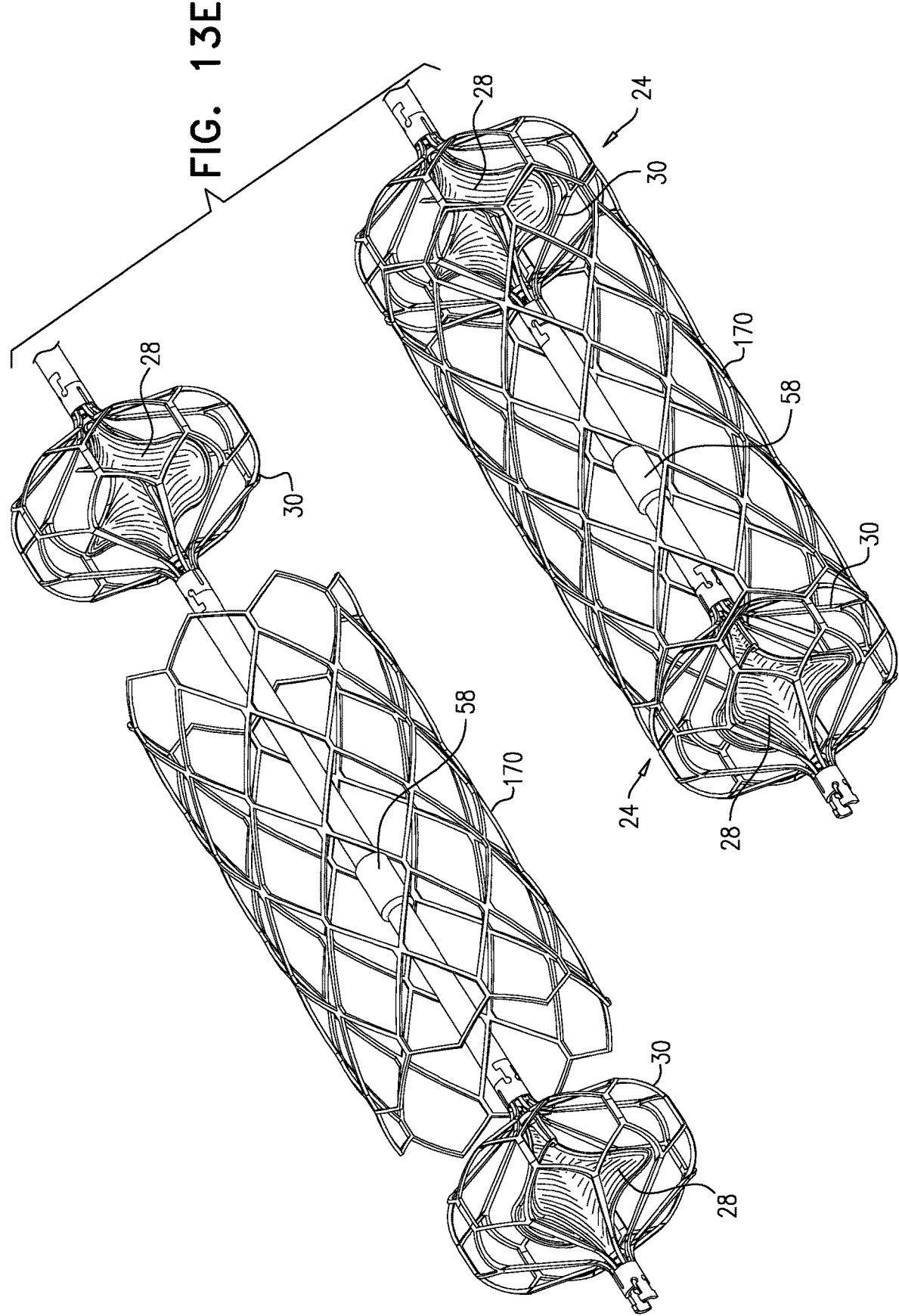

For some applications, as shown in FIGS. 13D-E, impellers 28D and 28U are placed inside support cage 170, in the presence of individual cages that are disposed around the respective impellers. Typically, the individual cages in which the impellers are disposed are generally similar to cage 30, as described hereinabove.

For some applications, support cage 170 is shaped to define individual cages 174 that are formed as a single integrated structure together with the support cage, as shown in FIG. 13D. For example, the individual cages and the support cage may be cut from a single piece of metal or alloy (e.g., nitinol). Alternatively, individual cages 30 may be formed separately from support cage 170, as shown in FIG. 13E. For such applications, the impellers may be placed inside individual cages 30, as described hereinabove, and individual cages 30 may then be placed inside support cage 170. For some such applications, individual cages 30 are placed inside support cage 170 inside the subject's body (e.g., inside the subject's vena cava). Alternatively, individual cages 30 are placed inside support cage 170 outside the subject's body (e.g., within guide catheter 23, shown in FIG. 1A), and the individual cages are deployed inside the subject's body (e.g., inside the subject's vena cava) together with the support cage.

In general, FIGS. 12 and FIGS. 13A-E show examples of blood-pump catheter 20 in which the blood-pump catheter includes a support structure (e.g., stent 160, or support cage 170), a longitudinal center of which is disposed between the upstream and downstream blood pumps (e.g., between the upstream and downstream impellers). For some applications, the longitudinal center of the support structure is disposed equidistantly from the upstream and downstream blood pumps (e.g., the upstream and downstream impellers). The support structure is configured to support an inner wall of the vena cava in an open configuration during the pumping of the blood by the first and second pumps. For some applications (not shown), a support structure, such as the structure shown in FIGS. 12 and 13A-E, is used in conjunction with a blood-pump catheter that includes a downstream pump and an upstream occlusion element (e.g., as shown in FIGS. 5A-B), mutatis mutandis. For such applications, the support structure is configured to support an inner wall of the vena cava in an open configuration during the pumping of the blood by the downstream pump.

Figure 14C:
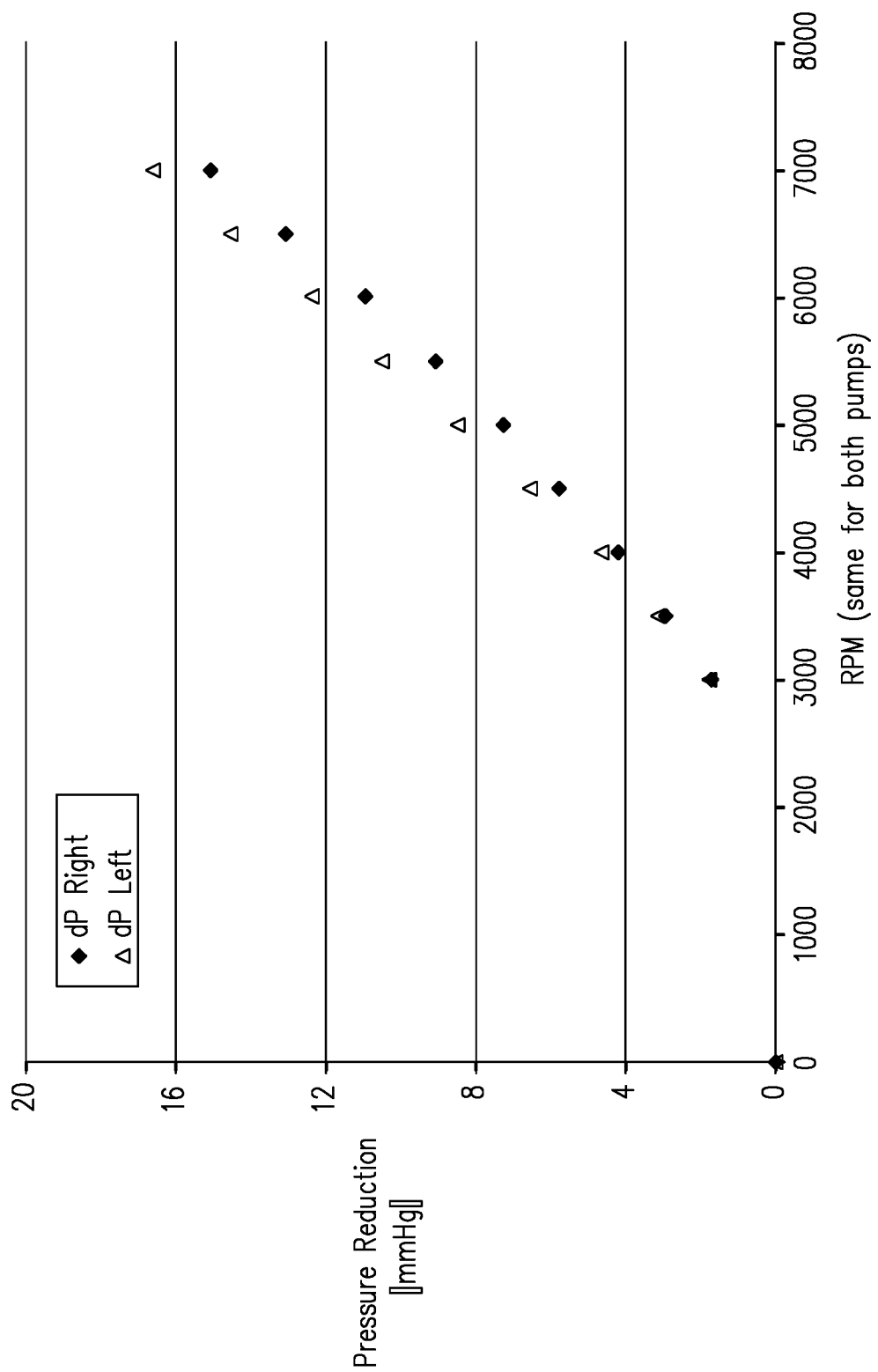

FIGS. 14A-C are graphs showing the pressure drop recorded in models of a subject's left and right renal veins, during experiments that were conducted using pumps, in accordance with some applications of the present invention.

In the experiments, a model of the vena cava and renal veins was used. The model was made of flexible silicone filled with saline. Upstream and downstream pumps as described herein were placed inside the vena cava, respectively below and above the renal veins. The pumps were activated to pump the saline through the vena cava in the manner described herein, and the drop in pressure in left and right renal veins was measured relative the pressure in the left and right renal veins before the pumps were activated.

FIG. 14A shows a plot of the measured pressure reduction (dP) in the left and right renal veins for respective rates of revolutions per minute (RPM) of the pumps (which was always the same for both pumps), for when the pumps were placed in the vena cava in the absence of either a support stent (as shown in FIG. 12) or a support cage (as shown in FIGS. 13A-E) between the upstream and downstream pumps.

FIG. 14B shows a plot of the measured pressure reduction (dP) in the left and right renal veins for respective rates of revolutions per minute (RPM) of the pumps (which was always the same for both pumps), for when the pumps were placed in the vena cava in the presence of a support stent (as shown in FIG. 12) between the upstream and downstream pumps.

FIG. 14C shows a plot of the measured pressure reduction (dP) in the left and right renal veins for respective rates of revolutions per minute (RPM) of the pumps (which was always the same for both pumps), for when the pumps were placed in the vena cava in the presence of a support cage between the upstream and downstream pumps, the support cage being configured as shown in FIG. 13E.

As may be observed in FIGS. 14A-C, the greatest pressure reduction was achieved when the pumps were used in conjunction with a support cage that extends at least from the longitudinal center of the downstream impeller to the longitudinal center of the upstream impeller (the results of which are shown in FIG. 14C). In addition, the most even pressure reduction of both the left and right renal veins was achieved when the pumps were used in conjunction with a support cage that extends at least from the longitudinal center of the downstream impeller to the longitudinal center of the upstream impeller. When a support stent as shown in FIG. 12 was disposed between the upstream and downstream pumps (the result of which are shown in FIG. 14B), there was still a greater and more even pressure reduction than when the upstream and downstream pumps were used in the absence of any supporting structure between the upstream and downstream pumps (the results of which are shown in FIG. 14A).

Therefore, the results shown in FIGS. 14A-C indicate that the efficacy of the reducing renal venous pressure by pumping blood through the vena cava using upstream and downstream pumps as described herein may be improved by placing a support structure inside the vena cava between the upstream and downstream pumps, in accordance with techniques described herein. Furthermore, the results indicate that the efficacy of the aforementioned technique may be particularly improved by placing a support cage inside the vena cava that extends at least from the longitudinal center of the downstream pump (e.g., the longitudinal center of the impeller of the downstream pump) to the longitudinal center of the upstream pump (e.g., longitudinal center of the impeller of the upstream pump). Therefore, for some applications of the present invention, apparatus and methods as described in FIGS. 12-13E are used.

Figures 15A, 15B:
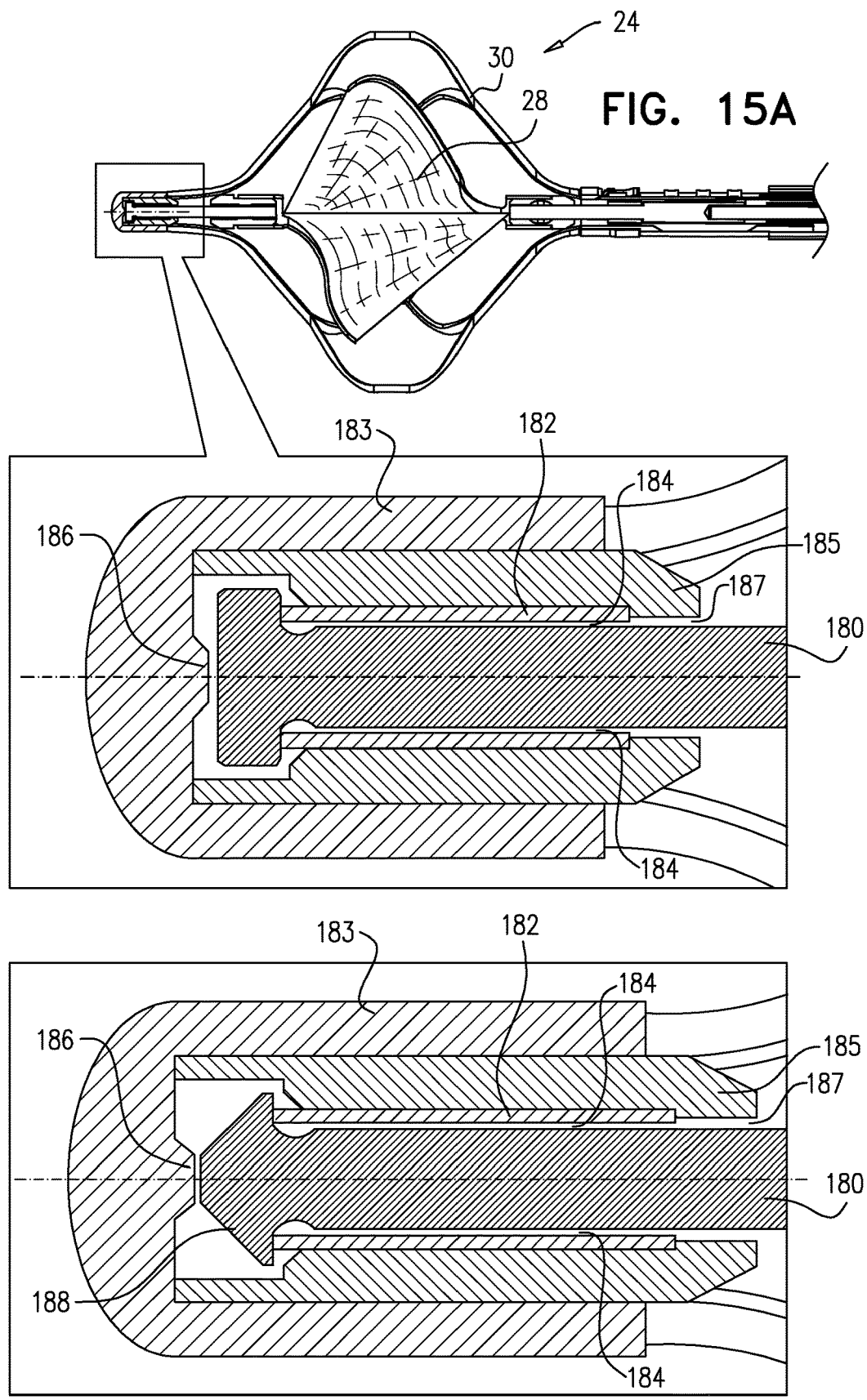
FIGS. 15A and 15B are schematic illustrations of a bearing and axial shaft of a distal end of an impeller, in accordance with respective applications of the present invention.

Reference is now made to FIGS. 15A-B, which are schematic illustrations of an axial shaft 180 of a distal end of impeller 28 and a bearing 182 within which the axial shaft rotates, in accordance with respective applications of the present invention. Typically, axial shaft 180 and bearing 182 are disposed inside a housing 183. For some applications, the axial shaft and the bearing are configured to reduce the formation of clots of blood that may be generated at the interface between the axial shaft and the bearing due to the heat generated by the axial shaft rotating within the bearing.

For some applications, as shown in FIG. 15A, the axial shaft and the bearing are sized such that there is a gap 184 between the axial shaft and the bearing. Typically, there is a difference between the outer diameter of the axial shaft and the inner diameter of the bearing that is greater than 0.02 mm (e.g., greater than 0.03 mm) and/or less than 0.1 mm (e.g., less than 0.07 mm), e.g., 0.02 mm-0.1 mm, or 0.03 mm-0.07 mm, such that gap 184 is defined between the axial shaft and the bearing. Typically, the gap facilitates the flow of blood therethrough which reduces friction at the interface between the axial shaft and the bearing.

For some applications, bearing 182 is supported inside housing 183 by a supporting element 185. Typically, the supporting element is sized such that, at locations at which the bearing does not separate between the supporting element and axial shaft 180, there is a gap 187 between the supporting element and the axial shaft. Typically, gap 187 between the supporting element and axial shaft is larger than gap 184 between the axial shaft and the bearing.

For some applications, housing 183 includes a protrusion 186 from its inner wall. The protrusion is configured to prevent the inner wall of the housing from wearing away due to contact between the distal end of the axial shaft and the inner wall of the housing.

For some applications, as shown in FIG. 15B, a distal end 188 of the axial shaft is frustoconically shaped. For some applications, due to the frustoconical shape of the distal end of the axial shaft, even if blood clots develop inside housing 183, the vector of the resisting force that is exerted upon the distal end of the axial shaft by the blood clots is such that it does not impede rotation of the axial shaft.

In experiments that were conducted by the inventors of the present application, impellers as described herein were rotated inside a Tygon® tube that contained blood. The blood was maintained at 37 degrees Celsius by being placed in a water bath. When a pump was used in which the difference between the outer diameter of the shaft and the inner diameter of the bearing was less than 0.02 mm, and in which the distal end of the axial shaft had not been shaped frustoconically, after one hour the motor current started to increase and showed instability. After another 10 minutes the impeller stopped rotating due to high resistance to rotation. The front axis assembly of the device was opened and clot formation was observed. Subsequently, a pump was operated under the same conditions, but the pump was configured such that the difference between the outer diameter of the shaft and the inner diameter of the bearing was between 0.04 mm and 0.05 mm, and the distal end of the axial shaft had been shaped frustoconically. In this case, the device worked for over 48 hours. These results indicate that using a pump that defines a gap, as described, between axial shaft 180 and bearing 182, and/or in which the distal end of axial shaft 180 is frustoconically shaped may reduce the likelihood of clot formation, relative to a pump that is not so configured.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

In general, in the specification and in the claims of the present application, the term "downstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is downstream, with respect to the direction of antegrade blood flow through the blood vessel, relative to a different location within the blood vessel. The term "upstream" and related terms, when used with reference to a blood vessel, or with reference to a portion of a device that is configured to be placed inside a blood vessel, should be interpreted to mean a location within the blood vessel, or a portion of the device that is intended for placement at a location within the blood vessel, that is upstream with respect to the direction of antegrade blood flow through the blood vessel, relative to a different location within the blood vessel.

It is noted that blood pumps 24U and 24D, the catheters upon which the blood pumps are disposed (e.g., blood-pump catheter 20, catheter 66, and catheter 68), and the occlusion elements described with reference to FIGS. 5A-B, and other devices described herein, are generally described as being placed within the subject's vena cava, such that the upstream pump or the occlusion element is disposed upstream of junctions of the vena cava with the subject's renal veins, and the downstream pump is disposed downstream of the junctions of the vena cava with the subject's renal veins. However, it is noted that the scope of the present invention includes placing upstream pump 24U or the occlusion element in any main vein upstream of a tributary venous system, and placing downstream pump 24D downstream of said tributary venous system, and configuring the pump(s) (e.g., via the direction of rotation of impellers of the pumps, or the orientation of the pumps) to generate preferential flow from the tributaries into the main vein, mutatis mutandis. For example, the pump(s) could be used to generate flow from the subject's hepatic veins into the subject's vena cava, in order to increase perfusion of the subject's liver, mutatis mutandis. For some applications, the upstream pump or the occlusion element is placed within a main vein upstream of two or more tributary venous systems into the main vein (e.g., within the vena cava upstream of the renal venous system and the hepatic venous system). The downstream pump is placed downstream of the two or more tributary venous systems. The pump(s) are configured to generate preferential flow from both of the tributary venous systems into the main vein by pumping blood through the main vein, in the manner described herein.

For some applications, upstream pump 24U or the occlusion element is placed in a main vein upstream of a tributary venous system, and downstream pump 24D is placed downstream of said tributary venous system, and the pump(s) are configured (e.g., via the direction of rotation of impellers of the pumps, or the orientation of the pumps) to reduce flow from the tributaries into the main vein. For some such applications, the blades of the downstream impeller are oriented such that, as the downstream impeller is rotated, the downstream impeller pumps in the upstream direction (toward the junction between the tributary system and the main vein). The blades of the upstream impeller are oriented such that, as the upstream impeller is rotated, the upstream impeller pumps in the downstream direction (toward the junction between the tributary system and the main vein).

For some applications, the upstream and downstream pumps 24U and 24D, the catheter(s) upon which the blood pumps are disposed (e.g., blood-pump catheter 20, catheter 66, and catheter 68), and/or the occlusion elements described with reference to FIGS. 5A-B, and other devices described herein, are placed within a main artery upstream and downstream of bifurcations of the artery with one or more branching arterial systems that branch from the main artery and supply a given organ, mutatis mutandis. For such applications, the upstream pump is typically configured to pump in the downstream direction (toward the bifurcations) and the downstream pump is configured to pump in the upstream direction (toward the bifurcations), such that blood flow into the branching arterial system is increased, thereby increasing perfusion of the organ. Alternatively or additionally, the occlusion element is placed downstream of the bifurcations of the artery with the one or more arterial systems and is configured to partially occlude the artery downstream of the bifurcations. For example, the upstream pump may be placed in the subject's aorta upstream of the subject's renal arteries and the downstream pump may be placed in the subject's aorta downstream of the subject's renal arteries, the pumps acting to pump blood into the renal arteries and toward the subject's kidneys. For some applications, upstream and downstream pumps, and/or occlusion elements are placed on both the arterial and venous sides of the subject's body in order to increase perfusion of a given organ or set of organs, in the manner described herein.

Although some applications of the present invention are described with reference to blood pumps 24D and 24U, according to which the blood pumps include impellers, the scope of the present invention includes using any other type of pump for pumping blood in the manner described herein, mutatis mutandis. For example, a roller pump, an Archimedes screw pump, a centrifugal pump, a pneumatic pump, and/or a compression pump may be used.

The scope of the present invention includes combining any of the apparatus and methods described herein with any of the apparatus and methods described in one or more of the following applications, all of which are incorporated herein by reference:

International Patent Application PCT/IL2015/050532 to Schwammenthal (published as WO 15/177793), filed May 19, 2015, entitled "Blood pump," which claims priority from U.S. Provisional Patent Application 62/000,192 to Schwammenthal, filed May 19, 2014, entitled "Blood pump;"

International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump;"

U.S. patent application Ser. No. 14/567,439 to Tuval (published as US 2015/0157777), filed Dec. 11, 2014, entitled "Curved catheter," which claims priority from U.S. Provisional Patent Application 61/914,470 to Tuval, filed Dec. 11, 2013, entitled "Curved catheter;" and International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. Apparatus comprising:
a blood pump comprising:
   a motor configured to be disposed outside a body of a subject;
   a catheter;
   a proximal impeller disposed on the catheter and being configured to pump blood by rotating;
   a distal impeller disposed on the catheter, the distal impeller being configured to pump blood by rotating and being disposed on the catheter distally to the proximal impeller such that longitudinal centers of the proximal and distal impellers are separated from each other by at least 3 cm;
   a shaft extending from the motor to the proximal impeller and the distal impeller, wherein the motor is configured to rotate the proximal and distal impellers by imparting rotational motion to the proximal and distal impellers via the shaft; and
   a tubular element disposed between the proximal impeller and the distal impeller.

2. The apparatus according to claim 1, wherein when the proximal and distal impellers are in non-radially-constrained configurations, the proximal and distal impellers are of opposing handedness with respect to one another, with one of the impellers being a left-handed impeller, and the other one of the impellers being a right-handed impeller.

3. The apparatus according to claim 1, wherein the motor is configured to rotate the proximal and distal impellers in opposite directions from one another.

4. The apparatus according to claim 1, wherein the motor is configured to rotate the proximal and distal impellers in the same direction as one another.

5. The apparatus according to claim 1, wherein the motor is configured to rotate the proximal and distal impellers at respective rotation rates that are different from one another.

6. The apparatus according to claim 1, wherein, when the proximal and distal impellers are in non-radially-constrained configurations, the proximal and distal impellers are sized differently from one another, such that, when the impellers are rotated at the same rotation rate as each other, flow rates at which blood is pumped by each of the impellers are different from each other.

7. The apparatus according to claim 1, wherein, when the proximal and distal impellers are in non-radially-constrained configurations, the proximal and distal impellers are shaped differently from one another, such that, when the impellers are rotated at the same rotation rate as each other, flow rates at which blood is pumped by each of the impellers are different from each other.

8. The apparatus according to claim 1, wherein, when the proximal and distal impellers are in non-radially-constrained configurations, the proximal and distal impellers are oriented differently from one another such that, when the impellers are rotated at the same rotation rate as each other, flow rates at which blood is pumped by each of the impellers are different from each other.

9. The apparatus according to claim 1, wherein the proximal and distal impellers are configured to pump the subject's blood in the same direction as each other, by rotating.

10. The apparatus according to claim 1, wherein the proximal and distal impellers are configured to pump the subject's blood in opposite directions from one another, by rotating.

11. The apparatus according to claim 1, wherein the tubular element is radially collapsible.

12. The apparatus according to claim 1, wherein the blood pump comprises a proximal impeller housing that houses the proximal impeller, and a distal impeller housing that houses the distal impeller and that is separate from the proximal impeller housing, and wherein the tubular element is disposed between the proximal impeller housing and the distal impeller housing.

13. The apparatus according to claim 12, wherein the proximal impeller housing encases the proximal impeller and the distal impeller housing encases the distal impeller.

14. A method comprising:
placing a blood pump inside vasculature of a subject, the blood pump including:
   a motor configured to be disposed outside a body of a subject;
   a catheter;
   a proximal impeller disposed on the catheter and being configured to pump blood by rotating;
   a distal impeller disposed on the catheter, the distal impeller being configured to pump blood by rotating and being disposed on the catheter distally to the proximal impeller such that longitudinal centers of the proximal and distal impellers are separated from each other by at least 3 cm;
   a shaft extending from the motor to the proximal impeller and the distal impeller; and
   a tubular element disposed between the proximal impeller and the distal impeller; and
pumping blood through the subject's body, by driving the proximal and distal impellers to rotate by the motor imparting rotational motion to the proximal and distal impellers via the shaft.

15. The method according to claim 14, wherein when the proximal and distal impellers are in non-radially-constrained configurations, the proximal and distal impellers are of opposing handedness with respect to one another, with one of the impellers being a left-handed impeller, and the other one of the impellers being a right-handed impeller.

16. The method according to claim 14, wherein driving the proximal and distal impellers to rotate comprises driving the proximal and distal impellers to rotate in the same direction as one another.

17. The method according to claim 14, wherein driving the proximal and distal impellers to rotate comprises driving the proximal and distal impellers to rotate in opposite directions from one another.

18. The method according to claim 14, wherein driving the proximal and distal impellers to rotate comprises driving the proximal and distal impellers to rotate at respective rotation rates that are different from one another.

19. The method according to claim 14, wherein driving the proximal and distal impellers to rotate comprises driving the proximal and distal impellers to rotate at the same rotation rate as each other, and wherein the proximal and distal impellers are sized differently from one another when the proximal and distal impellers are in non-radially-constrained configurations, such that, when the impellers are rotated at the same rotation rate as each other, flow rates at which blood is pumped by each of the impellers are different from each other.

20. The method according to claim 14, wherein driving the proximal and distal impellers to rotate comprises driving the proximal and distal impellers to rotate at the same rotation rate as each other, and wherein the proximal and distal impellers are shaped differently from one another when the proximal and distal impellers are in non-radially-constrained configurations, such that, when the impellers are rotated at the same rotation rate as each other, flow rates at which blood is pumped by each of the impellers are different from each other.

21. The method according to claim 14, wherein driving the proximal and distal to rotate comprises driving the proximal and distal impellers to rotate at the same rotation rate as each other, and wherein the proximal and distal impellers are oriented differently from one another when the proximal and distal impellers are in non-radially-constrained configurations, such that, when the impellers are rotated at the same rotation rate as each other, flow rates at which blood is pumped by each of the impellers are different from each other.

22. The method according to claim 14, wherein pumping blood through the subject's body by driving the proximal and distal impellers to rotate comprises driving the proximal and distal impellers to pump the subject's blood in the same direction as each other, by driving the proximal and distal impellers to rotate.

23. The method according to claim 14, wherein pumping blood through the subject's body by driving the proximal and distal impellers to rotate comprises driving the proximal and distal impellers to pump the subject's blood in opposite directions from one another, by driving the proximal and distal impellers to rotate.

24. The method according to claim 14, wherein the tubular element is radially collapsible.

25. The method according to claim 14, wherein the blood pump comprises a proximal impeller housing that houses the proximal impeller, and a distal impeller housing that houses the distal impeller and that is separate from the proximal impeller housing, and wherein the tubular element is disposed between the proximal impeller housing and the distal impeller housing.

26. The method according to claim 25, wherein the proximal impeller housing encases the proximal impeller and the distal impeller housing encases the distal impeller.

* * * * *